(12) United States Patent
Shelton, IV et al.

(10) Patent No.: US 12,121,305 B2
(45) Date of Patent: Oct. 22, 2024

(54) METHODS AND SYSTEMS FOR CONTROLLING COOPERATIVE SURGICAL INSTRUMENTS WITH VARIABLE SURGICAL SITE ACCESS TRAJECTORIES

(71) Applicant: Cilag GmbH International, Zug (CH)

(72) Inventors: Frederick E. Shelton, IV, Hillsboro, OH (US); Charles J. Scheib, Loveland, OH (US); Jason L. Harris, Lebanon, OH (US)

(73) Assignee: Cilag GmbH International, Zug (CH)

( * ) Notice: Subject to any disclaimer, the term of this patent is extended or adjusted under 35 U.S.C. 154(b) by 553 days.

(21) Appl. No.: 17/451,951

(22) Filed: Oct. 22, 2021

(65) Prior Publication Data

US 2023/0110718 A1    Apr. 13, 2023

Related U.S. Application Data

(60) Provisional application No. 63/249,881, filed on Sep. 29, 2021.

(51) Int. Cl.
*A61B 1/05* (2006.01)
*A61B 1/00* (2006.01)
(Continued)

(52) U.S. Cl.
CPC ........ *A61B 34/20* (2016.02); *A61B 1/000094* (2022.02); *A61B 1/000095* (2022.02);
(Continued)

(58) Field of Classification Search
CPC .............. A61B 1/0016; A61B 1/00009; A61B 17/3423; A61B 1/00194; A61B 1/313;
(Continued)

(56) References Cited

U.S. PATENT DOCUMENTS 5,188,104 A    2/1993 Wernicke et al.
5,231,988 A    8/1993 Wernicke et al.
(Continued)

FOREIGN PATENT DOCUMENTS

EP          1886711 B1    4/2018
WO    WO-2012007052 A1   1/2012
(Continued)

OTHER PUBLICATIONS

Shi et al., Three-Dimensional Intravascular Reconstruction Techniques Based on Intravascular Ultrasound: A Technical Review, 2017, IEEE, p. 806-817 (Year: 2017).*

(Continued)

*Primary Examiner* — Marc McDieunel
(74) *Attorney, Agent, or Firm* — Mintz, Levin, Cohn, Ferris, Glovsky and Popeo, P.C.

(57) ABSTRACT

Systems, devices, and methods for controlling cooperative surgical instruments with variable surgical site access trajectories are provided. Various aspects of the present disclosure provide for coordinated operation of surgical instruments accessing a common surgical site from different approach and/or separate body cavities to achieve a common surgical purpose. For example, various methods, devices, and systems disclosed herein can enable the coordinated treatment of tissue by disparate minimally invasive surgical systems that approach the tissue from varying anatomical spaces and must operate differently, but in concert with one another, to effect a desired surgical treatment.

9 Claims, 21 Drawing Sheets

(51) Int. Cl.
    *A61B 1/005* (2006.01)
    *A61B 1/04* (2006.01)
    *A61B 1/31* (2006.01)
    *A61B 1/313* (2006.01)
    *A61B 17/32* (2006.01)
    *A61B 17/34* (2006.01)
    *A61B 34/20* (2016.01)
    *G16H 20/40* (2018.01)
    *G16H 30/20* (2018.01)
    *G16H 40/63* (2018.01)
    *A61B 17/068* (2006.01)
    *A61B 17/115* (2006.01)
    *A61B 34/10* (2016.01)
    *A61B 34/30* (2016.01)

(52) U.S. Cl.
    CPC .............. *A61B 1/005* (2013.01); *A61B 1/044* (2022.02); *A61B 1/05* (2013.01); *A61B 1/31* (2013.01); *A61B 1/313* (2013.01); *A61B 17/320016* (2013.01); *A61B 17/3423* (2013.01); *G16H 20/40* (2018.01); *G16H 30/20* (2018.01); *G16H 40/63* (2018.01); *A61B 1/3132* (2013.01); *A61B 17/068* (2013.01); *A61B 17/115* (2013.01); *A61B 2034/107* (2016.02); *A61B 2034/2055* (2016.02); *A61B 2034/2065* (2016.02); *A61B 34/30* (2016.02); *A61B 2034/302* (2016.02)

(58) Field of Classification Search
    CPC ................ A61B 17/00491; A61B 1/31; A61B 17/0057; A61B 34/20; A61B 5/0036; A61B 5/0075; A61B 1/00149; A61B 90/03; A61B 1/053; A61B 1/005; A61B 90/37; A61B 1/0605; A61B 1/044; A61B 5/061; A61B 1/018; A61B 1/046; A61B 1/009; A61B 1/00126; A61B 1/0676; A61B 1/000094; A61B 1/00154; A61B 1/043; A61B 1/00087; A61B 34/37; A61B 17/320016; A61B 1/00055; A61B 90/36; A61B 1/00193; A61B 1/0638; A61B 1/000095; A61B 90/361; A61B 1/07; A61B 5/4887; A61B 1/05; A61B 1/0005; A61B 2090/365; A61B 2017/00628; A61B 2034/302; A61B 2090/373; A61B 2017/00893; A61B 17/068; A61B 2090/364; A61B 2090/031; A61B 2018/00702; A61B 2017/00606; A61B 2090/371; A61B 2017/00575; A61B 2090/0807; A61B 2017/00004; A61B 2034/2055; A61B 2090/08021; A61B 2034/2061; A61B 2034/107; A61B 2034/2065; A61B 17/115; A61B 34/30; A61B 2034/2051; A61B 18/14; A61B 2017/00818; A61B 2017/00951; A61B 1/3132; B25J 9/1697; B25J 9/1689; G16H 30/40; G16H 40/63; G16H 20/40; G16H 30/20; G05B 2219/45119; A61F 2/04
    See application file for complete search history.

(56) References Cited

U.S. PATENT DOCUMENTS

| | | |
|---|---|---|
| 5,256,149 A | 10/1993 | Banik et al. |
| 5,263,480 A | 11/1993 | Wernicke et al. |
| 5,540,730 A | 7/1996 | Terry, Jr. et al. |
| 5,558,671 A | 9/1996 | Yates |
| 6,086,528 A | 7/2000 | Adair |
| 7,143,925 B2 | 12/2006 | Shelton, IV et al. |
| 7,585,290 B2 | 9/2009 | Kathrani et al. |
| 7,601,118 B2 | 10/2009 | Smith et al. |
| 8,068,649 B2 | 11/2011 | Green |
| 8,317,070 B2 | 11/2012 | Hueil et al. |
| 8,352,026 B2 | 1/2013 | DiUbaldi |
| 8,393,514 B2 | 3/2013 | Shelton, IV et al. |
| 8,517,933 B2 | 8/2013 | Mohr |
| 8,545,515 B2 | 10/2013 | Prisco et al. |
| 8,551,115 B2 | 10/2013 | Steger et al. |
| 8,623,028 B2 | 1/2014 | Rogers et al. |
| 8,632,462 B2 | 1/2014 | Yoo et al. |
| 8,636,751 B2 | 1/2014 | Albrecht et al. |
| 8,734,478 B2 | 5/2014 | Widenhouse et al. |
| 8,753,338 B2 | 6/2014 | Widenhouse et al. |
| 8,771,180 B2 | 7/2014 | Mohr |
| 8,812,100 B2 | 8/2014 | Voegele et al. |
| 8,831,782 B2 | 9/2014 | Itkowitz |
| 8,888,789 B2 | 11/2014 | Prisco et al. |
| 8,919,348 B2 | 12/2014 | Williams et al. |
| 8,961,406 B2 | 2/2015 | Ortiz et al. |
| 9,044,606 B2 | 6/2015 | Harris et al. |
| 9,072,535 B2 | 7/2015 | Shelton, IV et al. |
| 9,072,536 B2 | 7/2015 | Shelton, IV et al. |
| 9,204,879 B2 | 12/2015 | Shelton, IV |
| 9,216,062 B2 | 12/2015 | Duque et al. |
| 9,254,178 B2 | 2/2016 | Prisco et al. |
| 9,274,047 B2 | 3/2016 | Velten et al. |
| 9,283,050 B2 | 3/2016 | Prisco et al. |
| 9,320,416 B2 | 4/2016 | Cooper et al. |
| 9,339,341 B2 | 5/2016 | Cooper |
| 9,358,074 B2 | 6/2016 | Schena et al. |
| 9,393,017 B2 | 7/2016 | Flanagan et al. |
| 9,561,038 B2 | 2/2017 | Shelton, IV et al. |
| 9,572,481 B2 | 2/2017 | Duindam et al. |
| 9,636,186 B2 | 5/2017 | Kumar et al. |
| 9,757,128 B2 | 9/2017 | Baber et al. |
| 9,832,848 B2 * | 11/2017 | Hidaka .............. H05B 47/115 |
| 9,962,161 B2 | 5/2018 | Scheib et al. |
| 10,092,738 B2 | 10/2018 | Harris et al. |
| 10,179,024 B2 | 1/2019 | Yeung |
| 10,206,682 B2 | 2/2019 | Bakos et al. |
| 10,245,069 B2 | 4/2019 | Rogers et al. |
| 10,492,788 B2 | 12/2019 | Swayze et al. |
| 10,517,600 B2 | 12/2019 | Beisel et al. |
| 10,569,071 B2 | 2/2020 | Harris et al. |
| 10,716,564 B2 | 7/2020 | Shelton, IV et al. |
| 10,751,117 B2 | 8/2020 | Witt et al. |
| 10,779,831 B2 | 9/2020 | Lukin et al. |
| 10,792,034 B2 | 10/2020 | Scheib et al. |
| 10,856,928 B2 | 12/2020 | Shelton, IV et al. |
| 10,925,598 B2 | 2/2021 | Scheib et al. |
| 11,033,272 B2 | 6/2021 | Fegelman et al. |
| 11,051,876 B2 | 7/2021 | Shelton, IV et al. |
| 11,344,374 B2 * | 5/2022 | Tekiela .................. A61B 34/25 |
| 11,357,582 B1 * | 6/2022 | Roh ........................ G10L 13/02 |
| 11,446,104 B2 | 9/2022 | Adams |
| 2002/0065455 A1 | 5/2002 | Ben-Haim et al. |
| 2003/0135091 A1 | 7/2003 | Nakazawa et al. |
| 2005/0277998 A1 | 12/2005 | Tracey et al. |
| 2006/0195146 A1 | 8/2006 | Tracey et al. |
| 2006/0195153 A1 | 8/2006 | DiUbaldi et al. |
| 2006/0258938 A1 | 11/2006 | Hoffman et al. |
| 2007/0185541 A1 | 8/2007 | DiUbaldi et al. |
| 2008/0004603 A1 | 1/2008 | Larkin et al. |
| 2008/0065110 A1 | 3/2008 | Duval et al. |
| 2008/0132962 A1 | 6/2008 | DiUbaldi et al. |
| 2008/0147146 A1 | 6/2008 | Wahlgren et al. |
| 2009/0062792 A1 | 3/2009 | Vakharia et al. |
| 2009/0093809 A1 | 4/2009 | Anderson et al. |
| 2009/0132018 A1 | 5/2009 | DiUbaldi et al. |
| 2009/0149918 A1 | 6/2009 | Krulevitch et al. |
| 2009/0157149 A1 | 6/2009 | Wahlgren et al. |
| 2010/0056863 A1 | 3/2010 | Dejima et al. |
| 2010/0161001 A1 | 6/2010 | DiUbaldi et al. |
| 2010/0161005 A1 | 6/2010 | Wahlgren et al. |
| 2010/0191267 A1 | 7/2010 | Fox |

(56) References Cited

U.S. PATENT DOCUMENTS

| | | |
|---|---|---|
| 2010/0239648 A1 | 9/2010 | Smith et al. |
| 2011/0094773 A1 | 4/2011 | Bare et al. |
| 2011/0118708 A1 | 5/2011 | Burbank et al. |
| 2012/0150192 A1 | 6/2012 | Dachs, II et al. |
| 2012/0209314 A1 | 8/2012 | Weir et al. |
| 2013/0105545 A1 | 5/2013 | Burbank |
| 2013/0105552 A1 | 5/2013 | Weir et al. |
| 2013/0146643 A1 | 6/2013 | Schmid et al. |
| 2013/0221065 A1 | 8/2013 | Aronhalt et al. |
| 2013/0253550 A1 | 9/2013 | Beisel et al. |
| 2013/0256377 A1 | 10/2013 | Schmid et al. |
| 2014/0066717 A1 | 3/2014 | Rogers et al. |
| 2014/0121678 A1 | 5/2014 | Trusty et al. |
| 2015/0129634 A1 | 5/2015 | Shelton, IV et al. |
| 2015/0133995 A1 | 5/2015 | Shelton, IV et al. |
| 2015/0133996 A1 | 5/2015 | Shelton, IV et al. |
| 2015/0134076 A1 | 5/2015 | Shelton, IV et al. |
| 2015/0134077 A1 | 5/2015 | Shelton, IV et al. |
| 2015/0238268 A1 | 8/2015 | Weir et al. |
| 2015/0238276 A1 | 8/2015 | Atarot et al. |
| 2015/0257841 A1 | 9/2015 | Dachs, II |
| 2015/0257842 A1 | 9/2015 | Dachs, II |
| 2015/0272575 A1 | 10/2015 | Leimbach et al. |
| 2015/0351758 A1 | 12/2015 | Shelton, IV et al. |
| 2016/0256071 A1 | 9/2016 | Shelton, IV et al. |
| 2016/0262761 A1 | 9/2016 | Beisel et al. |
| 2016/0303743 A1 | 10/2016 | Rockrohr |
| 2016/0346930 A1 | 12/2016 | Hares |
| 2017/0035425 A1 | 2/2017 | Fegelman et al. |
| 2017/0055819 A1 | 3/2017 | Hansen et al. |
| 2017/0071693 A1 | 3/2017 | Taylor et al. |
| 2017/0086927 A1 | 3/2017 | Auld et al. |
| 2017/0128041 A1 | 5/2017 | Hasser et al. |
| 2017/0128144 A1 | 5/2017 | Hasser et al. |
| 2017/0128145 A1 | 5/2017 | Hasser et al. |
| 2017/0181808 A1 | 6/2017 | Panescu et al. |
| 2017/0189131 A1 | 7/2017 | Weir |
| 2017/0202591 A1 | 7/2017 | Shelton, IV et al. |
| 2017/0212723 A1 | 7/2017 | Atarot et al. |
| 2017/0231477 A1 | 8/2017 | del Nido et al. |
| 2017/0251900 A1 | 9/2017 | Hansen et al. |
| 2017/0265866 A1 | 9/2017 | Ryou et al. |
| 2018/0049820 A1 | 2/2018 | Widenhouse et al. |
| 2018/0177556 A1 | 6/2018 | Noonan |
| 2018/0289432 A1 | 10/2018 | Kostrzewski et al. |
| 2018/0296280 A1 | 10/2018 | Kurihara et al. |
| 2018/0325604 A1 | 11/2018 | Atarot et al. |
| 2018/0353174 A1 | 12/2018 | Widenhouse et al. |
| 2019/0025040 A1 | 1/2019 | Andreason et al. |
| 2019/0099209 A1 | 4/2019 | Witt et al. |
| 2019/0125431 A1 | 5/2019 | Shelton, IV et al. |
| 2019/0200844 A1 | 7/2019 | Shelton, IV et al. |
| 2019/0200905 A1 | 7/2019 | Shelton, IV et al. |
| 2019/0200981 A1 | 7/2019 | Harris et al. |
| 2019/0201046 A1 | 7/2019 | Shelton, IV et al. |
| 2019/0201088 A1 | 7/2019 | Shelton, IV et al. |
| 2019/0201114 A1 | 7/2019 | Shelton, IV et al. |
| 2019/0201136 A1 | 7/2019 | Shelton, IV et al. |
| 2019/0201140 A1 | 7/2019 | Yates et al. |
| 2019/0204201 A1 | 7/2019 | Shelton, IV et al. |
| 2019/0206004 A1 | 7/2019 | Shelton, IV et al. |
| 2019/0206050 A1 | 7/2019 | Yates et al. |
| 2019/0206555 A1 | 7/2019 | Morgan et al. |
| 2019/0207857 A1 | 7/2019 | Shelton, IV et al. |
| 2020/0000530 A1 | 1/2020 | DeFonzo et al. |
| 2020/0015668 A1 | 1/2020 | Scheib |
| 2020/0015897 A1 | 1/2020 | Scheib et al. |
| 2020/0015898 A1 | 1/2020 | Scheib et al. |
| 2020/0015899 A1 | 1/2020 | Scheib et al. |
| 2020/0015900 A1 | 1/2020 | Scheib et al. |
| 2020/0015901 A1 | 1/2020 | Scheib et al. |
| 2020/0015902 A1 | 1/2020 | Scheib et al. |
| 2020/0015903 A1 | 1/2020 | Scheib et al. |
| 2020/0015906 A1 | 1/2020 | Scheib et al. |
| 2020/0015907 A1 | 1/2020 | Scheib |
| 2020/0015914 A1 | 1/2020 | Scheib et al. |
| 2020/0015923 A1 | 1/2020 | Scheib et al. |
| 2020/0015924 A1 | 1/2020 | Scheib et al. |
| 2020/0015925 A1 | 1/2020 | Scheib |
| 2020/0046404 A1 | 2/2020 | Page et al. |
| 2020/0078109 A1 | 3/2020 | Steger et al. |
| 2020/0085516 A1 | 3/2020 | DeFonzo et al. |
| 2020/0170718 A1 | 6/2020 | Peine |
| 2020/0170720 A1 | 6/2020 | Ummalaneni |
| 2020/0188043 A1 | 6/2020 | Yu et al. |
| 2020/0188046 A1 | 6/2020 | Overmyer et al. |
| 2020/0214709 A1 | 7/2020 | Motai |
| 2020/0315723 A1 | 10/2020 | Hassan et al. |
| 2020/0315724 A1 | 10/2020 | Takikawa et al. |
| 2020/0405417 A1 | 12/2020 | Shelton, IV et al. |
| 2021/0085410 A1 | 3/2021 | Hassan |
| 2021/0153724 A1 | 5/2021 | Ries et al. |
| 2021/0196108 A1 | 7/2021 | Shelton, IV |
| 2021/0196109 A1 | 7/2021 | Shelton, IV et al. |
| 2021/0196381 A1 | 7/2021 | Eckert et al. |
| 2021/0196383 A1 | 7/2021 | Shelton, IV et al. |
| 2021/0196384 A1 | 7/2021 | Shelton, IV et al. |
| 2021/0196385 A1 | 7/2021 | Shelton, IV et al. |
| 2021/0196386 A1 | 7/2021 | Shelton, IV et al. |
| 2021/0196399 A1 | 7/2021 | Ayvali et al. |
| 2021/0196423 A1 | 7/2021 | Shelton, IV et al. |
| 2021/0196424 A1 | 7/2021 | Shelton, IV et al. |
| 2021/0196425 A1 | 7/2021 | Shelton, IV et al. |
| 2021/0199557 A1 | 7/2021 | Shelton, IV et al. |
| 2021/0212784 A1 | 7/2021 | Ramadorai |
| 2021/0290317 A1 | 9/2021 | Sen et al. |
| 2021/0393338 A1 | 12/2021 | Graetzel et al. |
| 2021/0393344 A1 | 12/2021 | Graetzel et al. |
| 2022/0096172 A1* | 3/2022 | Strobl .................. G01J 5/0022 |
| 2022/0101745 A1* | 3/2022 | Yu ....................... G06F 3/04815 |
| 2022/0133420 A1* | 5/2022 | Fuerst ................... A61B 90/50 606/130 |
| 2022/0183779 A1* | 6/2022 | Shuh ................ A61B 17/00234 |
| 2022/0202427 A1* | 6/2022 | Overmyer ........ A61B 17/00234 |
| 2023/0096268 A1 | 3/2023 | Shelton, IV et al. |
| 2023/0096691 A1 | 3/2023 | Shelton, IV et al. |
| 2023/0099189 A1 | 3/2023 | Shelton, IV et al. |
| 2023/0101192 A1 | 3/2023 | Shelton, IV et al. |

FOREIGN PATENT DOCUMENTS

| | | |
|---|---|---|
| WO | WO-2014151621 A1 | 9/2014 |
| WO | WO-2015142814 A1 | 9/2015 |
| WO | WO-2015153636 A1 | 10/2015 |
| WO | WO-2015153642 A1 | 10/2015 |
| WO | WO-2016144937 A1 | 9/2016 |
| WO | WO-2016144998 A1 | 9/2016 |
| WO | WO-2016183054 A1 | 11/2016 |
| WO | WO-2016205266 A1 | 12/2016 |
| WO | WO-2016205452 A1 | 12/2016 |
| WO | WO-2016209769 A1 | 12/2016 |
| WO | WO-2017044406 A1 | 3/2017 |
| WO | WO-2017053358 A1 | 3/2017 |
| WO | WO-2017053363 A1 | 3/2017 |
| WO | WO-2017053507 A1 | 3/2017 |
| WO | WO-2017053698 A1 | 3/2017 |
| WO | WO-2017075121 A1 | 5/2017 |
| WO | WO-2017116793 A1 | 7/2017 |
| WO | WO-2020260999 A1 | 12/2020 |

OTHER PUBLICATIONS

Hussain et al., Contribution of Augmented Reality to Minimally Invasive Computer-Assisted Cranial Base Surgery, 2106, IEEE, p. 2093-2106 (Year: 2106).*

Sun et al., Virtually transparent epidermal imagery for laparo-endoscopic single-site surgery, 2011, IEEE, p. 2107-2110 (Year: 2011).*

Linte et al., Virtual and Augmented Medical Imaging Environments: Enabling Technology for Minimally Invasive Cardiac Interventional Guidance, 2010, IEEE, p. 25-47 (Year: 2010).*

U.S. Appl. No. 17/450,025, filed Oct. 5, 2021, Frederick E. Shelton, IV et al.

(56) References Cited

OTHER PUBLICATIONS

U.S. Appl. No. 17/451,953, filed Oct. 22, 2021, Frederick E. Shelton, IV et al.
U.S. Appl. No. 17/451,954, filed Oct. 22, 2021, Frederick E. Shelton, IV et al.
International Search Report and Written Opinion for International Application No. PCT/IB2022/059094, mailed on Dec. 23, 2022, 13 pages.
International Search Report and Written Opinion for International Application No. PCT/IB2022/059100, mailed on Jan. 2, 2023, 17 pages.
International Search Report and Written Opinion for International Application No. PCT/IB2022/059086, mailed on Feb. 1, 14, 2023, 18 pages.
"Fiber Bragg Gatings," RP Photonics Encyclopedia, available at <https://www.rp-photonics.com/fiber_bragg_gratings.html>, dated no later than Apr. 5, 2021 (12 pages).
"Ion by Intuitive," available at <https://www.intuitive.com/en-us/products-and-services/ion>, dated no later than Apr. 5, 2021 (5 pages).
Aisu et al., Laparoscopic and endoscopic cooperative surgery for gastric tumors: Perspective for actual practice and oncological benefits,: World J Gastrointest Oncol, Nov. 15, 2018, 10(11): 381-397.
Akirov, "Duodenal Mucosal Resurfacing May Safely Improve Glycemic Control in T2D," Aug. 19, 2019, Haymarket Media, Inc., 14 pages.
Brace et al., "Thermal Tumor Ablation in Clinical Use," IEEE Pulse, 2011, 2(5):28-38.
Carlota V., "4D printing reconfigurable materials for use in aerospace, medical and robotics fields," Apr. 3, 2019, available at <https://www.3dnatices.com/en/4d-printing-materials-030420195/> (7 pages).
Chauhan etal, "Enteroscopy," Gastrointestinal Endoscopy, 2015, vol. 82, No. 6, 975-990.
Conway et al., "Endoscopic hemostatic devices," Gastrointestinal Endoscopy, 2009, vol. 69, No. 6, 987-996.
Dunkin et al., "Thin-layer ablation of human esophagael epithelium using a bipolar radiofrequency balloon device," Surg Endosc (2006) 20: 125-130.
Ethicon, "Laparoscopic Sizing Tool: LINX® Reflux Management System," 2019 (6 pages).
Fried et al., "A novel approach to glycemic control in type 2 diabetes mellius, partial jejunal diversion: pre-clinical to clinical pathway," BMJ Open Diab Res Care 2017; 5:e000431.doi:10.1136*BMJdrc-2017000431.
Garvey, "Ablation of the Duodenal Mucosa as a Strategy for Glycemic Control in Diabetes: Role of Nutrient Signaling or Simple Weight Loss," Diabetes Care 2016; 39:2108-2110.
Gioux et al., "Image-Guided Surgery using Invisible Near-Infrared Light: Fundamental of Clinical Translation," Mol Imaging, Oct. 9, 2010,)5): 237-255.
Gupta, "Understanding Image Recognition and Its Uses," eInfochips, available at <http://www.einfochips.com/blog/understanding-image-recognition-and-its-uses/>, Dec. 11, 2019.
Hiki et al., "Laparoscopic and endoscopic cooperative surgery for gastrointestinal stromal tumor dissection," Surg Endosc (2008) 22:1729-1735.
Intuitive Surgical, "Da Vinci Xi Single-Site Technology: Solutions For Single-Incision Surgery," 2016 (10 pages).
Kurata et al., "Time-Of-Flight Near-Infrared Spectroscopy For Nondestructive Measurement Of Internal Quality In Grapefruit," Journal of the American Society for Horticultural Science, May 2013 vol. 138 No. 3 225-228.
Machytka et al., "Partial jejunal diversion using an incisionless magnetic anastomosis system: 1-year interim results in patients with obesity and diabetes," Gastrointestinal Endoscopy, 2017, vol. 86, No. 5, 904-912.
Matsuda et al., "Laparoscopic endoscopic cooperative surgery (LECS) for the upper gastrointestinal tract," Transl Gastroenterol Hepatol 2017, 2:40 (6 pages).
Miklavčič et al., "Electric Properties of Tissues," Wiley Encyclopedia of Biomedical Engineering, 2006, 1-12.
Sculpteo, "4D Printing: A technology coming from the future," 3D Learning Hub, dated no later than Aug. 26, 2021 (12 pages).
Seeley et al., "The Role of Gut Adaptation in the Potent Effects of Multiple Bariatric Surgeries on Obesity and Diabetes," Cell Metabolism 21, Mar. 3, 2015, 369-378.
Tamegai et al., "Laparoscopic and endoscopic cooperative surgery (LECS) to overcome the limitations of endoscopic resection for colorectal tumors," Endosc Int Open, Dec. 2018, 6(12): E1477-E1485.
Tokar et al., "Electrosurgical generators," Gastrointestinal Endoscopy, 2013, vol. 78, No. 2, 197-208.
Tomie et al., "Blue Laser Imaging—Bright Improves Endoscopic Recognition of Superficial Esophagael Squamous Cell Carcinoma," Gastroenterology Research and Practice, vol. 2016, Article ID 6140854, 7 pages.
Toposens, "Advanced Ultrasonic Sensors: What Makes Them Different?" available at <https://toposens.com/technology/>, 2020.
Toposens, "Beacon Based 3D Tracking System," available at <https://toposens.com/beacon-based-3d-ttracking-system/>, 2020.
U.S. Appl. No. 17/449,765 entitled "Cooperative Access Hybrid Procedures" filed Oct. 1, 2021.
U.S. Appl. No. 17/493,904 entitled "Surgical Methods Using Multi-Source Imaging" filed Oct. 5, 2021.
U.S. Appl. No. 17/450,020 entitled "Methods for Controlling Cooperative Surgical Instruments" filed Oct. 5, 2021.
U.S. Appl. No. 17/450,027 entitled "Methods for Controlling Cooperative Surgical Instruments" filed Oct. 5, 2021.
U.S. Appl. No. 17/493,913 entitled "Surgical Methods Using Fiducial Identification and Tracking" filed Oct. 5, 2021.
U.S. Appl. No. 17/494,364 entitled "Surgical Methods for Control of One Visualization With Another" filed Oct. 5, 2021.
U.S. Appl. No. 17/068,857 entitled "Adaptive Responses From Smart Packaging Of Drug Delivery Absorbable Adjuncts" filed Oct. 13, 2020.
U.S. Appl. No. 17/068,858 entitled "Drug Administration Devices That Communicate With Surgical Hubs" filed Oct. 13, 2020.
U.S. Appl. No. 17/068,859 entitled "Controlling Operation Of Drug Administration Devices Using Surgical Hubs" filed Oct. 13, 2020.
U.S. Appl. No. 17/068,863 entitled "Patient Monitoring Using Drug Administration Devices" filed Oct. 13, 2020.
U.S. Appl. No. 17/068,865 entitled "Monitoring And Communicating Information Using Drug Administration Devices" filed Oct. 13, 2020.
U.S. Appl. No. 17/068,867 entitled "Aggregating And Analyzing Drug Administration Data" filed Oct. 13, 2020.
Van Baar et al., "Endoscopic duodenal mucosal resurfacing for the treatment of type 2 diabetes mellitus: one year results from the first international, open label, prospective, multicentre study," Gut 2020, 69:295-303.
Yang et al., "4d printing reconfigurable, deployable and mechanically tunable materials," Material Science, 2019 (33 pages).
Zuo et al., "Pulmonary Intersegmental Places: Imaging Appearance and Possible Reasons Leading to Their Visualization," Radiology, vol. 267, No. 1, Apr. 2013, 267-275.

\* cited by examiner

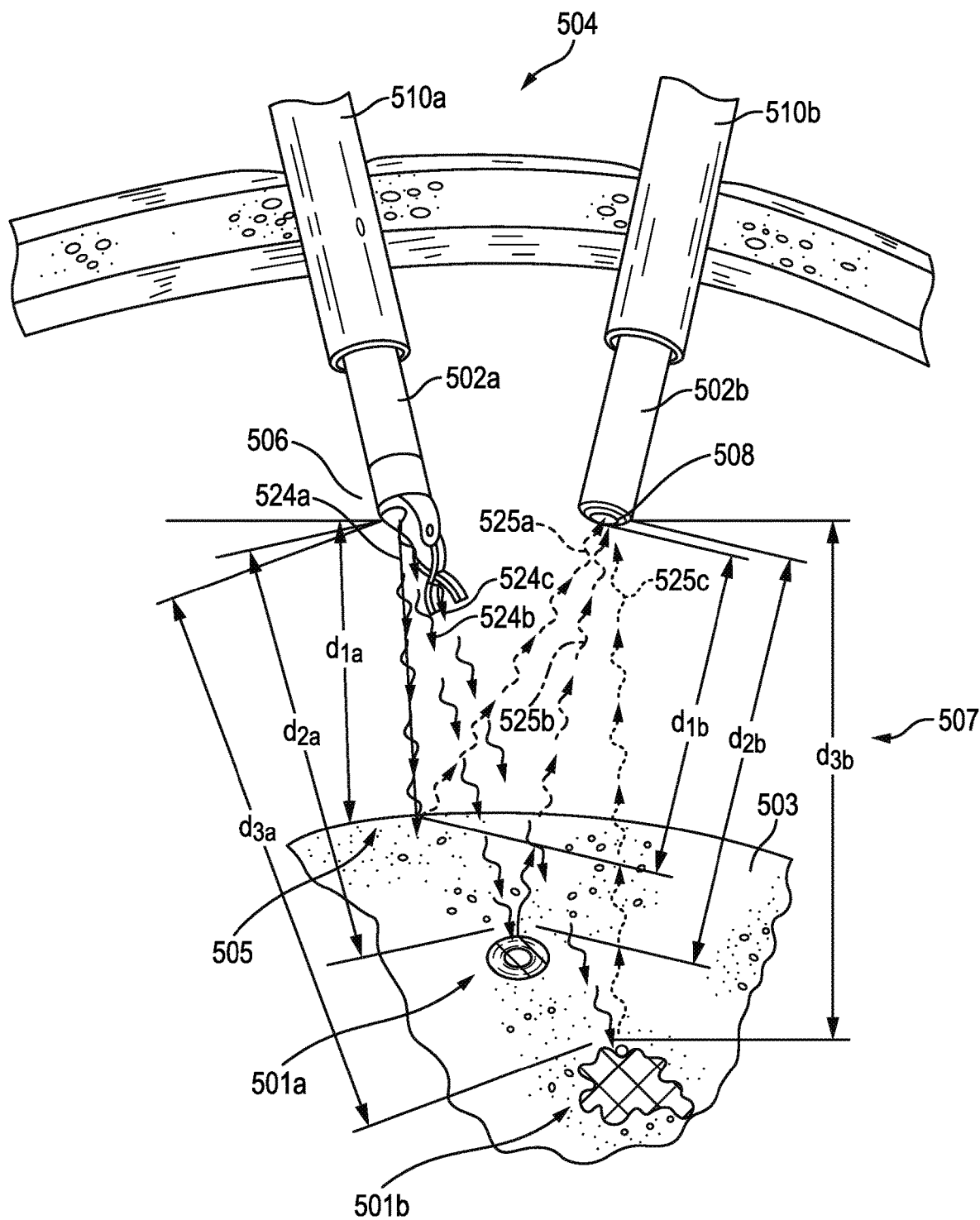

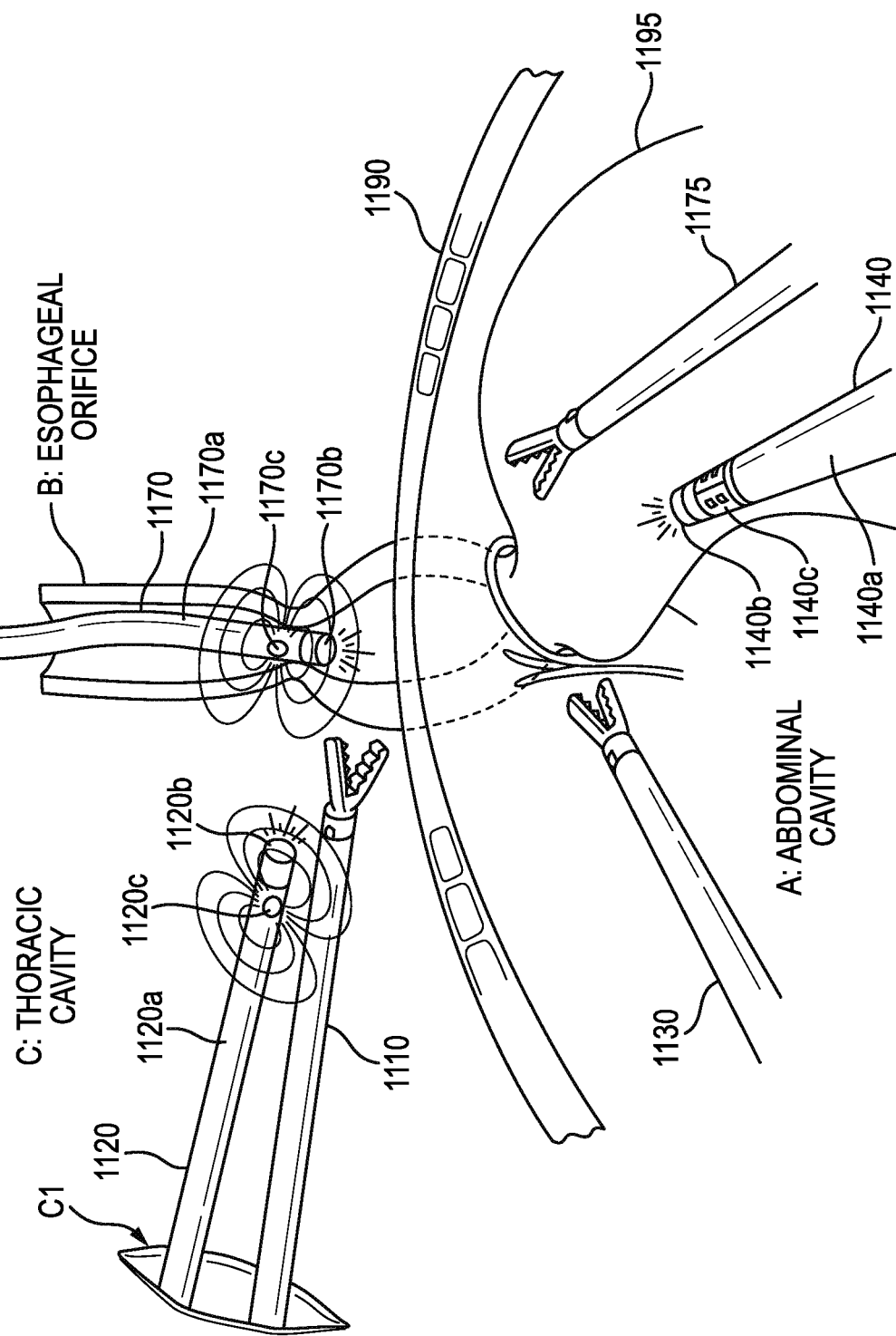

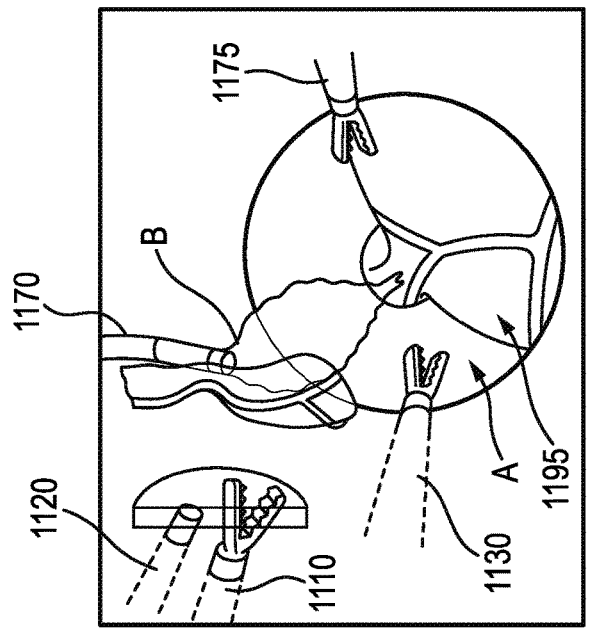
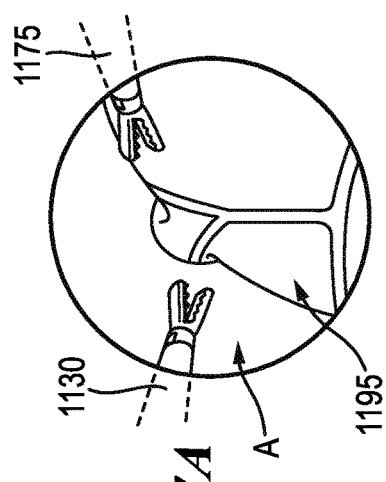
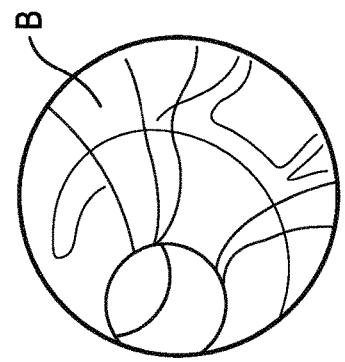
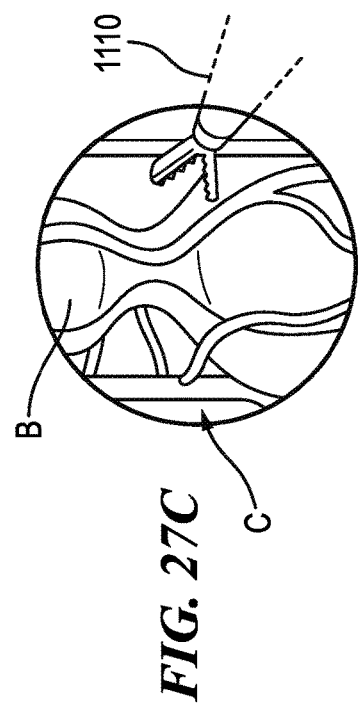
FIG. 27A
FIG. 27B
FIG. 27C
FIG. 27D

METHODS AND SYSTEMS FOR CONTROLLING COOPERATIVE SURGICAL INSTRUMENTS WITH VARIABLE SURGICAL SITE ACCESS TRAJECTORIES

CROSS-REFERENCE TO RELATED APPLICATIONS

This application claims priority to U.S. Provisional Patent Application No. 63/249,881, filed Sep. 29, 2021, and entitled "Methods and Systems for Controlling Cooperative Surgical Instruments with Variable Surgical Site Access Trajectories," the disclosure of which is incorporated herein by reference in its entirety.

BACKGROUND

Some surgical procedures require the use of a plurality of surgical instruments operating on a region or portion of tissue at the same time to successfully execute the procedure. In some situations, due to anatomical limitations and/or the nature of the procedure, it is not possible for the plurality of surgical instruments to be located in the same anatomic spaces. For example, during a procedure in which a region of an enclosed tissue structure (e.g., a wall of an esophagus) is operated on, to successfully execute the procedure, one of the plurality of surgical instruments may be required to be located within the enclosed tissue structure and an other of the plurality of surgical instruments may be required to be located outside of the enclosed tissue structure.

However, in some implementations, a first surgical instrument for operating on a region of tissue that approaches the region of tissue from a first anatomic space may be operated independently from a second surgical instrument for operating on the region of tissue that approaches the region of tissue from a second, unrelated anatomic space. In such a scenario, it may be difficult or impossible for the first and second surgical instruments to be manipulated together to achieve a successful surgical outcome in situations where coordinated operation of the first and second surgical instruments is required to successfully execute a procedure.

In addition, surgical systems often incorporate an imaging system, which can allow medical practitioners to view a surgical site and/or one or more portions thereof on one or more displays, e.g., a monitor, a computer tablet screen, etc. The display(s) can be local and/or remote to a surgical theater. The imaging system can include a scope with a camera that views the surgical site and transmits the view to the one or more displays viewable by medical practitioner(s).

Imaging systems can be limited by the information that they are able to recognize and/or convey to the medical practitioner(s). For example, certain concealed structures, physical contours, and/or dimensions within a three-dimensional space may be unrecognizable intraoperatively by certain imaging systems. For another example, certain imaging systems may be incapable of communicating and/or conveying certain information to the medical practitioner(s) intraoperatively.

Accordingly, there remains a need for improved methods and systems for controlling cooperative surgical instruments with variable surgical site access trajectories and for improved surgical imaging. There also remains a need for improved methods and systems for controlling cooperative surgical instruments with variable surgical site access trajectories.

SUMMARY

In an aspect, a system is provided and can include a first surgical instrument configured to be inserted into a first body cavity of a patient, the first body cavity located outside of a lumen structure of the patient, a second surgical instrument configured to be inserted into the lumen structure, a first endoscope having a first image sensor configured to acquire a first image of the first surgical instrument within the first body cavity and positioned such that the second surgical instrument is not within a field of view of the first image sensor, a second endoscope having a second image sensor configured to acquire a second image of the second surgical instrument within the lumen structure and positioned such that the first surgical instrument is not within a field of view of the second image sensor, and a controller configured to receive the first and second images, to determine a first location of the first surgical instrument and a second location of the second surgical instrument relative to one another based on the received first and second images, and to coordinate cooperative movement of the first and second surgical instruments based on the determined first and second locations. The first surgical instrument can be configured to deliver an adjunct to a target area located at the lumen structure, and the second surgical instrument can be configured to deliver a cooperative fixating implant to the surgical site from within the lumen structure such that the cooperative fixating implant helps maintain the adjunct in place at the target area.

In some embodiments, the adjunct can be configured to require interaction from each of the first and second surgical instruments for implantation of the adjunct. In some embodiments, the adjunct can be configured to require interaction from within the first body cavity located outside of the lumen structure of the patient and from within the lumen structure for implantation of the adjunct.

In another aspect, a system is provided and can include a data processor and memory storing instructions configured to cause the data processor to perform operations. The operations can include receiving, in real time, from a first image sensor of a first endoscope, first image data characterizing a first image of a first surgical instrument disposed within a first body cavity of a patient and located outside of a lumen structure of the patient, the first surgical instrument configured to deliver an adjunct to a target area located at the lumen structure; receiving, in real time, from a second image sensor of a second endoscope, second image data characterizing a second image of a second surgical instrument disposed within the lumen structure, the second surgical instrument configured to deliver a cooperative fixating implant to the target area from within the lumen structure such that the cooperative fixating implant helps maintain in place at the target area, the second surgical instrument outside of a field of view of the first endoscope and the first surgical instrument outside of a field of view of the second endoscope; determining, based on the received first image data, a first location of the first surgical instrument; determining, based on the received second image data, a second location of the second surgical instrument; and coordinating cooperative movement between the first and second surgical instruments based on the determined first and second locations.

In some embodiments, the adjunct can be configured to require interaction from each of the first and second surgical instruments for implantation of the adjunct. In some embodiments, the adjunct can be configured to require interaction from within the first body cavity located outside of the lumen structure of the patient and from within the lumen structure for implantation of the adjunct.

In another aspect, a method is provided and can include receiving, by a controller, in real time, from a first image sensor of a first endoscope, first image data characterizing a first image of a first surgical instrument disposed within a first body cavity of a patient and located outside of a lumen structure of the patient, the first surgical instrument configured to deliver an adjunct to a target area located at the lumen structure; receiving, by the controller, in real time, from a second image sensor of a second endoscope, second image data characterizing a second image of a second surgical instrument disposed within the lumen structure, the second surgical instrument configured to deliver a cooperative fixating implant to the target area from within the lumen structure such that the adjunct is maintained in place at the target area by the cooperative fixating implant, the second surgical instrument outside of a field of view of the first endoscope and the first surgical instrument outside of a field of view of the second endoscope; determining, by the controller, based on the received first image data, a first location of the first surgical instrument; determining, by the controller, based on the received second image data, a second location of the second surgical instrument relative to the first location of the first surgical instrument; and coordinating, by the controller, cooperative movement between the first and second surgical instruments based on the determined first and second locations.

In some embodiments, the adjunct can require interaction from each of the first and second surgical instruments for implantation of the adjunct at the target area. In some embodiments, the adjunct can require interaction from within the first body cavity located outside of the lumen structure of the patient and from within the lumen structure for implantation of the adjunct at the target area.

In another aspect, a system is provided and can include a first surgical instrument configured to be inserted into a thoracic body cavity of a patient and to operate on a first surface of a tissue located within the patient, a second surgical instrument configured to be inserted into an abdominal body cavity of the patient and to operate on a second surface of the tissue, the second surface oriented differently from the first surface, a first endoscope having a first image sensor configured to acquire a first image of the first surgical instrument within the thoracic body cavity and positioned such that the second surgical instrument is not within a field of view of the first image sensor, a second endoscope having a second image sensor configured to acquire a second image of the second surgical instrument within the abdominal body cavity and positioned such that the first surgical instrument is not within a field of view of the second image sensor, and a controller configured to receive the first and second images, to determine a first location of the first surgical instrument and a second location of the second surgical instrument relative to one another, and to coordinate cooperative treatment between the first and second surgical instruments by applying interrelated limits on actuators of the first and second surgical instruments in different directions from each other based on the determined first and second locations.

In some embodiments, the controller can be configured to control motions for cooperative forces and motions between the first and second surgical instruments. In some embodiments, the tissue can be at least partially anchored to adjacent anatomical structures such that a proportionate amount of the cooperative force are transmitted into tissue connections to the adjacent anatomical structures. In some embodiments, the tissue can be anchored to surrounding anatomic structures. In some embodiments, the tissue can be a common tissue wall separating the first thoracic body cavity and the second abdominal body cavity. In some embodiments, the controller can be configured to limit applied forces and motions from the first surgical instrument on the common tissue based on applied forces and motions from the second surgical instrument on the common tissue.

In another aspect, a system is provided and can include a data processor and memory storing instructions configured to cause the data processor to perform operations. The operations can include receiving, in real time, from a first image sensor of a first endoscope, first image data characterizing a first image of a first surgical instrument disposed within a thoracic body cavity of a patient and configured to operate on a first surface of a tissue located within the patient; receiving, in real time, from a second image sensor of a second endoscope, second image data characterizing a second image of a second surgical instrument disposed within an abdominal body cavity of the patient, and to operate on a second surface of the tissue, the second surface oriented differently from the first surface, the second surgical instrument outside of a field of view of the first endoscope and the first surgical instrument outside of a field of view of the second endoscope; determining, based on the received first image data, a first location of the first surgical instrument; determining, based on the received second image data, a second location of the second surgical instrument relative to the first location of the first surgical instrument; and coordinating cooperative treatment between the first and second surgical instruments to achieve a common surgical purpose on the tissue, wherein cooperative treatment of the tissue includes applying interrelated limits on actuators of the first and second surgical instruments in different directions from each other based on the determined first and second locations.

In some embodiments, the operations can further include controlling motions for cooperative forces and motions between the first and second surgical instruments. In some embodiments, the tissue can be at least partially anchored to adjacent anatomical structures such that a proportionate amount of the cooperative force are transmitted into tissue connections to the adjacent anatomical structures. In some embodiments, the tissue can be anchored to surrounding anatomic structures. In some embodiments, the tissue can be a common tissue wall separating the first thoracic body cavity and the second abdominal body cavity. In some embodiments, the at least one data processor can be configured to limit applied forces and motions from the first surgical instrument on the common tissue based on applied forces and motions from the second surgical instrument on the common tissue.

In another aspect, a method is provided and can include receiving, by a controller, in real time, from a first image sensor of a first endoscope, first image data characterizing a first image of a first surgical instrument disposed within a first thoracic body cavity of a patient and configured to operate on a first surface of a tissue located within the patient; receiving, by the controller, in real time, from a second image sensor of a second endoscope, second image data characterizing a second image of a second surgical instrument disposed within a second abdominal body cavity of the patient, and to operate on a second surface of the tissue, the second surface oriented differently from the first surface, the second surgical instrument outside of a field of view of the first endoscope and the first surgical instrument outside of a field of view of the second endoscope, the second abdominal body cavity being distinct from the first thoracic body cavity; determining, by the controller, based on the received first image data, a first location of the first surgical instrument; determining, by the controller, based on the received second image data, a second location of the second surgical instrument relative to the first location of the first surgical instrument; and coordinating, by the controller, cooperative treatment between the first and second surgical instruments to achieve a common surgical purpose on the tissue, wherein cooperative treatment of the tissue includes applying interrelated limits on actuators of the first and second surgical instruments in different directions from each other based on the determined first and second locations.

In some embodiments, motions for cooperative forces and motions between the first and second surgical instruments can be controlled. In some embodiments, the tissue can be at least partially anchored to adjacent anatomical structures such that a proportionate amount of the cooperative force is transmitted into tissue connections to the adjacent anatomical structures. In some embodiments, the tissue can be anchored to surrounding anatomic structures. In some embodiments, the tissue can be a common tissue wall separating the thoracic body cavity and the abdominal body cavity. In some embodiments, applied forces and motions from the first surgical instrument on the common tissue can be limited based on applied forces and motions from the second surgical instrument on the common tissue.

In another aspect, a system is provided and can include a first surgical instrument configured to be inserted into a first body cavity of a patient and to operate on a first surface of a tissue located within the patient, a second surgical instrument configured to be inserted into a second body cavity of the patient and to operate on a second surface of the tissue, the second surface oriented differently from the first surface, a first endoscope having a first image sensor configured to acquire a first image of the first surgical instrument within the first body cavity and positioned such that the second surgical instrument is not within a field of view of the first image sensor, a second endoscope having a second image sensor configured to acquire a second image of the second surgical instrument within the second body cavity and positioned such that the first surgical instrument is not within a field of view of the second image sensor, the second body cavity being distinct from the first body cavity, and a controller configured to receive the first and second images, to determine a first location of the first surgical instrument based on the received first image, to determine a second location of the second surgical instrument from the second image, and to coordinate cooperative treatment between the first and second surgical instruments based on the determined first and second locations by manipulation of the common tissue by either the first surgical instrument or the second surgical instrument in a first direction such that the other of the first surgical instrument or the second surgical instrument treats the tissue when the tissue is manipulated in the first direction.

In some embodiments, forces between the first and second surgical instruments can be controlled to produce at least one of a predefined motion or force therebetween. In some embodiments, the first body cavity can be within a first hollow organ within the patient, the first surgical instrument can be configured to manipulate the common tissue in the first direction within the hollow organ, and the second body cavity can be outside of the hollow organ. In some embodiments, the first surgical instrument can be configured to provide at least one of tissue deflection, retraction, or movement of the common tissue such that the second surgical instrument has access to dissect a portion of the common tissue. In some embodiments, visualization of the common tissue by the first image sensor of the first endoscope can be configured to allow dissection of at least a part of the common tissue by the second surgical instrument.

In another aspect, a system is provided and can include a data processor and memory storing instructions configured to cause the data processor to perform operations. The operations can include receiving, in real time, from a first image sensor of a first endoscope, first image data characterizing a first image of a first surgical instrument disposed within a first body cavity of a patient and configured to operate on a first surface of a tissue located within the patient; receiving, in real time, from a second image sensor of a second endoscope, second image data characterizing a second image of a second surgical instrument disposed within a second body cavity of the patient, and to operate on a second surface of the tissue, the second surface oriented differently from the first surface, the second surgical instrument outside of a field of view of the first endoscope and the first surgical instrument outside of a field of view of the second endoscope, the second body cavity being distinct from the first body cavity; determining, based on the received first image data, a first location of the first surgical instrument; determining, based on the received second image data, a second location of the second surgical instrument; and coordinating cooperative treatment between the first and second surgical instruments to achieve a common surgical purpose on the tissue based on the determined first and second locations, wherein cooperative treatment of the tissue includes manipulation of the common tissue by either the first surgical instrument or the second surgical instrument in a first direction such that the other of the first surgical instrument or the second surgical instrument treats the common tissue when the common tissue is manipulated in the first direction.

In some embodiments, forces between the first and second surgical instruments can be controlled to produce at least one of a predefined motion or force therebetween. In some embodiments, the first body cavity can be within a first hollow organ within the patient, the first surgical instrument can be configured to manipulate the common tissue in the first direction within the hollow organ, and the second body cavity can be outside of the hollow organ. In some embodiments, the first surgical instrument can be configured to provide at least one of tissue deflection, retraction, or movement of the common tissue such that the second surgical instrument has access to dissect a portion of the common tissue. In some embodiments, visualization of the common tissue by the first image sensor of the first endoscope can be configured to allow dissection of at least a part of the common tissue by the second surgical instrument.

In another aspect, a method is provided and can include receiving, by a controller, in real time, from a first image sensor of a first endoscope, first image data characterizing a first image of a first surgical instrument disposed within a first body cavity of a patient and configured to operate on a first surface of a tissue located within the patient; receiving, by the controller, in real time, from a second image sensor of a second endoscope, second image data characterizing a second image of a second surgical instrument disposed within a second body cavity of the patient, and to operate on a second surface of the tissue, the second surface oriented differently from the first surface, the second surgical instrument outside of a field of view of the first endoscope and the first surgical instrument outside of a field of view of the second endoscope, the second body cavity being distinct from the first body cavity; determining, by the controller, based on the received first image data, a first location of the first surgical instrument; determining, by the controller, based on the received second image data, a second location of the second surgical instrument; and coordinating, by the controller, cooperative treatment between the first and second surgical instruments based on the determined first and second locations to achieve a common surgical purpose on the tissue, including manipulating the common tissue by either first surgical instrument or the second surgical instrument in a first direction such that the other of first surgical instrument or the second surgical instrument treats the common tissue when the common tissue is manipulated in the first direction.

In some embodiments, forces between the first and second surgical instruments can be controlled to produce at least one of a predefined motion or force therebetween. In some embodiments, the first body cavity can be within a first hollow organ within the patient, the first surgical instrument can manipulate the common tissue in the first direction within the hollow organ, and the second body cavity can be outside of the hollow organ. In some embodiments, the first surgical instrument can provide at least one of tissue deflection, retraction, or movement of the common tissue such that the second surgical instrument has access to dissect a portion of the common tissue. In some embodiments, visualization of the common tissue by the first image sensor of the first endoscope can be configured to allow dissection of at least a part of the common tissue by the second surgical instrument.

BRIEF DESCRIPTION OF DRAWINGS

The present invention is described by way of reference to the accompanying figures which are as follows:

FIG. 17 is a schematic view of another embodiment of a near infrared (NIR) time-of-flight measurement system being utilized intraoperatively;

FIG. 26 is an illustrative view of an example embodiment of a system for providing a common field of view by augmenting multiple points of view into the common field of view via the use/tracking of sensors placed on a plurality of endoscopes placed in a surgical field;

FIG. 27A is an illustrative view of the field of view of the second endoscope of FIG. 25 and FIG. 26;

FIG. 27B is an illustrative view of the field of view of the third endoscope of FIG. 25 and FIG. 26;

FIG. 27C is an illustrative view of the field of view of the first endoscope of FIG. 25 and FIG. 26;

FIG. 27D is an augmented composite image created based on the fields of view of the first, second, and third endoscopes of FIG. 25 and FIG. 26;

DETAILED DESCRIPTION

Figure 1:
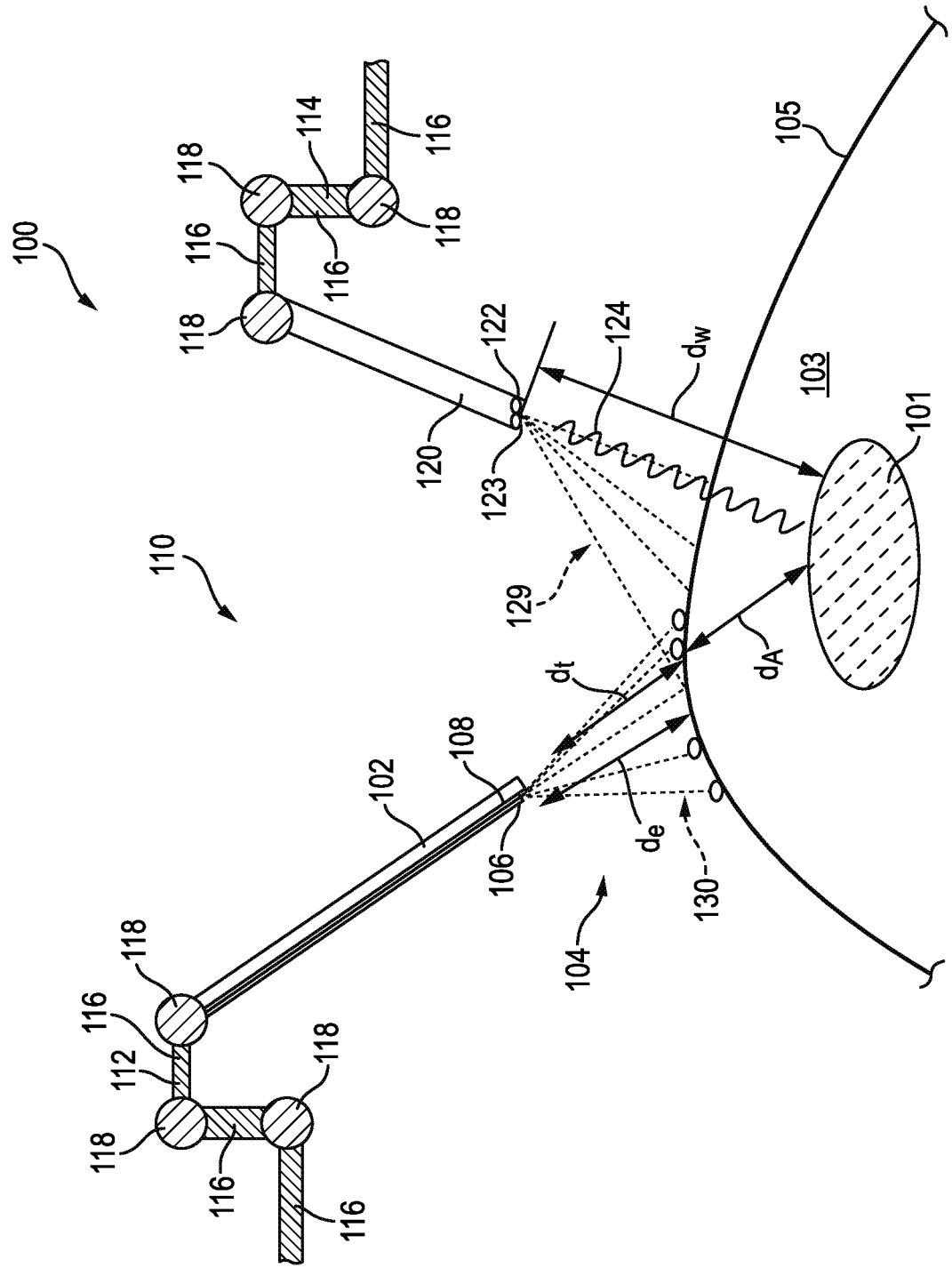
FIG. 1 is a schematic view of one embodiment of a surgical visualization system.

Certain exemplary embodiments will now be described to provide an overall understanding of the principles of the structure, function, manufacture, and use of the devices, systems, and methods disclosed herein. One or more examples of these embodiments are illustrated in the accompanying drawings. A person skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. A person skilled in the art will appreciate that a dimension may not be a precise value but nevertheless be considered to be at about that value due to any number of factors such as manufacturing tolerances and sensitivity of measurement equipment. Sizes and shapes of the systems and devices, and the components thereof, can depend at least on the size and shape of components with which the systems and devices will be used.

Surgical Visualization

In general, a surgical visualization system is configured to leverage "digital surgery" to obtain additional information about a patient's anatomy and/or a surgical procedure. The surgical visualization system is further configured to convey data to one or more medical practitioners in a helpful manner. Various aspects of the present disclosure provide improved visualization of the patient's anatomy and/or the surgical procedure, and/or use visualization to provide improved control of a surgical tool (also referred to herein as a "surgical device" or a "surgical instrument").

"Digital surgery" can embrace robotic systems, advanced imaging, advanced instrumentation, artificial intelligence, machine learning, data analytics for performance tracking and benchmarking, connectivity both inside and outside of the operating room (OR), and more. Although various surgical visualization systems described herein can be used in combination with a robotic surgical system, surgical visualization systems are not limited to use with a robotic surgical system. In certain instances, surgical visualization using a surgical visualization system can occur without robotics and/or with limited and/or optional robotic assistance. Similarly, digital surgery can occur without robotics and/or with limited and/or optional robotic assistance.

In certain instances, a surgical system that incorporates a surgical visualization system may enable smart dissection in order to identify and avoid critical structures. Critical structures include anatomical structures such as a ureter, an artery such as a superior mesenteric artery, a vein such as a portal vein, a nerve such as a phrenic nerve, and/or a tumor, among other anatomical structures. In other instances, a critical structure can be a foreign structure in the anatomical field, such as a surgical device, a surgical fastener, a clip, a tack, a bougie, a band, a plate, and other foreign structures. Critical structures can be determined on a patient-by-patient and/or a procedure-by-procedure basis. Smart dissection technology may provide, for example, improved intraoperative guidance for dissection and/or may enable smarter decisions with critical anatomy detection and avoidance technology.

A surgical system incorporating a surgical visualization system may enable smart anastomosis technologies that provide more consistent anastomoses at optimal location(s) with improved workflow. Cancer localization technologies may be improved with a surgical visualization platform. For example, cancer localization technologies can identify and track a cancer location, orientation, and its margins. In certain instances, the cancer localization technologies may compensate for movement of a surgical instrument, a patient, and/or the patient's anatomy during a surgical procedure in order to provide guidance back to the point of interest for medical practitioner(s).

A surgical visualization system may provide improved tissue characterization and/or lymph node diagnostics and mapping. For example, tissue characterization technologies may characterize tissue type and health without the need for physical haptics, especially when dissecting and/or placing stapling devices within the tissue. Certain tissue characterization technologies may be utilized without ionizing radiation and/or contrast agents. With respect to lymph node diagnostics and mapping, a surgical visualization platform may, for example, preoperatively locate, map, and ideally diagnose the lymph system and/or lymph nodes involved in cancerous diagnosis and staging.

During a surgical procedure, information available to a medical practitioner via the "naked eye" and/or an imaging system may provide an incomplete view of the surgical site. For example, certain structures, such as structures embedded or buried within an organ, can be at least partially concealed or hidden from view. Additionally, certain dimensions and/or relative distances can be difficult to ascertain with existing sensor systems and/or difficult for the "naked eye" to perceive. Moreover, certain structures can move pre-operatively (e.g., before a surgical procedure but after a preoperative scan) and/or intraoperatively. In such instances, the medical practitioner can be unable to accurately determine the location of a critical structure intraoperatively.

When the position of a critical structure is uncertain and/or when the proximity between the critical structure and a surgical tool is unknown, a medical practitioner's decision-making process can be inhibited. For example, a medical practitioner may avoid certain areas in order to avoid inadvertent dissection of a critical structure; however, the avoided area may be unnecessarily large and/or at least partially misplaced. Due to uncertainty and/or overly/excessive exercises in caution, the medical practitioner may not access certain desired regions. For example, excess caution may cause a medical practitioner to leave a portion of a tumor and/or other undesirable tissue in an effort to avoid a critical structure even if the critical structure is not in the particular area and/or would not be negatively impacted by the medical practitioner working in that particular area. In certain instances, surgical results can be improved with increased knowledge and/or certainty, which can allow a surgeon to be more accurate and, in certain instances, less conservative/more aggressive with respect to particular anatomical areas.

A surgical visualization system can allow for intraoperative identification and avoidance of critical structures. The surgical visualization system may thus enable enhanced intraoperative decision making and improved surgical outcomes. The surgical visualization system can provide advanced visualization capabilities beyond what a medical practitioner sees with the "naked eye" and/or beyond what an imaging system can recognize and/or convey to the medical practitioner. The surgical visualization system can augment and enhance what a medical practitioner is able to know prior to tissue treatment (e.g., dissection, etc.) and, thus, may improve outcomes in various instances. As a result, the medical practitioner can confidently maintain momentum throughout the surgical procedure knowing that the surgical visualization system is tracking a critical structure, which may be approached during dissection, for example. The surgical visualization system can provide an indication to the medical practitioner in sufficient time for the medical practitioner to pause and/or slow down the surgical procedure and evaluate the proximity to the critical structure to prevent inadvertent damage thereto. The surgical visualization system can provide an ideal, optimized, and/or customizable amount of information to the medical practitioner to allow the medical practitioner to move confidently and/or quickly through tissue while avoiding inadvertent damage to healthy tissue and/or critical structure(s) and, thus, to minimize the risk of harm resulting from the surgical procedure.

Surgical visualization systems are described in detail below. In general, a surgical visualization system can include a first light emitter configured to emit a plurality of spectral waves, a second light emitter configured to emit a light pattern, and a receiver, or sensor, configured to detect visible light, molecular responses to the spectral waves (spectral imaging), and/or the light pattern. The surgical visualization system can also include an imaging system and a control circuit in signal communication with the receiver and the imaging system. Based on output from the receiver, the control circuit can determine a geometric surface map, e.g., three-dimensional surface topography, of the visible surfaces at the surgical site and a distance with respect to the surgical site, such as a distance to an at least partially concealed structure. The imaging system can convey the geometric surface map and the distance to a medical practitioner. In such instances, an augmented view of the surgical site provided to the medical practitioner can provide a representation of the concealed structure within the relevant context of the surgical site. For example, the imaging system can virtually augment the concealed structure on the geometric surface map of the concealing and/or obstructing tissue similar to a line drawn on the ground to indicate a utility line below the surface. Additionally or alternatively, the imaging system can convey the proximity of a surgical tool to the visible and obstructing tissue and/or to the at least partially concealed structure and/or a depth of the concealed structure below the visible surface of the obstructing tissue. For example, the visualization system can determine a distance with respect to the augmented line on the surface of the visible tissue and convey the distance to the imaging system.

Throughout the present disclosure, any reference to "light," unless specifically in reference to visible light, can include electromagnetic radiation (EMR) or photons in the visible and/or non-visible portions of the EMR wavelength spectrum. The visible spectrum, sometimes referred to as the optical spectrum or luminous spectrum, is that portion of the electromagnetic spectrum that is visible to (e.g., can be detected by) the human eye and may be referred to as "visible light" or simply "light." A typical human eye will respond to wavelengths in air that are from about 380 nm to about 750 nm. The invisible spectrum (e.g., the non-luminous spectrum) is that portion of the electromagnetic spectrum that lies below and above the visible spectrum. The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

FIG. 1 illustrates one embodiment of a surgical visualization system 100. The surgical visualization system 100 is configured to create a visual representation of a critical structure 101 within an anatomical field. The critical structure 101 can include a single critical structure or a plurality of critical structures. As discussed herein, the critical structure 101 can be any of a variety of structures, such as an anatomical structure, e.g., a ureter, an artery such as a superior mesenteric artery, a vein such as a portal vein, a nerve such as a phrenic nerve, a vessel, a tumor, or other anatomical structure, or a foreign structure, e.g., a surgical device, a surgical fastener, a surgical clip, a surgical tack, a bougie, a surgical band, a surgical plate, or other foreign structure. As discussed herein, the critical structure 101 can be identified on a patient-by-patient and/or a procedure-by-procedure basis. Embodiments of critical structures and of identifying critical structures using a visualization system are further described in U.S. Pat. No. 10,792,034 entitled "Visualization Of Surgical Devices" issued Oct. 6, 2020, which is hereby incorporated by reference in its entirety.

In some instances, the critical structure 101 can be embedded in tissue 103. The tissue 103 can be any of a variety of tissues, such as fat, connective tissue, adhesions, and/or organs. Stated differently, the critical structure 101 may be positioned below a surface 105 of the tissue 103. In such instances, the tissue 103 conceals the critical structure 101 from the medical practitioner's "naked eye" view. The tissue 103 also obscures the critical structure 101 from the view of an imaging device 120 of the surgical visualization system 100. Instead of being fully obscured, the critical structure 101 can be partially obscured from the view of the medical practitioner and/or the imaging device 120.

The surgical visualization system 100 can be used for clinical analysis and/or medical intervention. In certain instances, the surgical visualization system 100 can be used intraoperatively to provide real-time information to the medical practitioner during a surgical procedure, such as real-time information regarding proximity data, dimensions, and/or distances. A person skilled in the art will appreciate that information may not be precisely real time but nevertheless be considered to be real time for any of a variety of reasons, such as time delay induced by data transmission, time delay induced by data processing, and/or sensitivity of measurement equipment. The surgical visualization system 100 is configured for intraoperative identification of critical structure(s) and/or to facilitate the avoidance of the critical structure(s) 101 by a surgical device. For example, by identifying the critical structure 101, a medical practitioner can avoid maneuvering a surgical device around the critical structure 101 and/or a region in a predefined proximity of the critical structure 101 during a surgical procedure. For another example, by identifying the critical structure 101, a medical practitioner can avoid dissection of and/or near the critical structure 101, thereby helping to prevent damage to the critical structure 101 and/or helping to prevent a surgical device being used by the medical practitioner from being damaged by the critical structure 101.

The surgical visualization system 100 is configured to incorporate tissue identification and geometric surface mapping in combination with the surgical visualization system's distance sensor system 104. In combination, these features of the surgical visualization system 100 can determine a position of a critical structure 101 within the anatomical field and/or the proximity of a surgical device 102 to the surface 105 of visible tissue 103 and/or to the critical structure 101. Moreover, the surgical visualization system 100 includes an imaging system that includes the imaging device 120 configured to provide real-time views of the surgical site. The imaging device 120 can include, for example, a spectral camera (e.g., a hyperspectral camera, multispectral camera, or selective spectral camera), which is configured to detect reflected spectral waveforms and generate a spectral cube of images based on the molecular response to the different wavelengths. Views from the imaging device 120 can be provided in real time to a medical practitioner, such as on a display (e.g., a monitor, a computer tablet screen, etc.). The displayed views can be augmented with additional information based on the tissue identification, landscape mapping, and the distance sensor system 104. In such instances, the surgical visualization system 100 includes a plurality of subsystems—an imaging subsystem, a surface mapping subsystem, a tissue identification subsystem, and/or a distance determining subsystem. These subsystems can cooperate to intra-operatively provide advanced data synthesis and integrated information to the medical practitioner.

The imaging device 120 can be configured to detect visible light, spectral light waves (visible or invisible), and a structured light pattern (visible or invisible). Examples of the imaging device 120 includes scopes, e.g., an endoscope, an arthroscope, an angioscope, a bronchoscope, a choledochoscope, a colonoscope, a cytoscope, a duodenoscope, an enteroscope, an esophagogastro-duodenoscope (gastroscope), a laryngoscope, a nasopharyngo-neproscope, a sigmoidoscope, a thoracoscope, an ureteroscope, or an exoscope. Scopes can be particularly useful in minimally invasive surgical procedures. In open surgery applications, the imaging device 120 may not include a scope.

The tissue identification subsystem can be achieved with a spectral imaging system. The spectral imaging system can rely on imaging such as hyperspectral imaging, multispectral imaging, or selective spectral imaging. Embodiments of hyperspectral imaging of tissue are further described in U.S. Pat. No. 9,274,047 entitled "System And Method For Gross Anatomic Pathology Using Hyperspectral Imaging" issued Mar. 1, 2016, which is hereby incorporated by reference in its entirety.

The surface mapping subsystem can be achieved with a light pattern system. Various surface mapping techniques using a light pattern (or structured light) for surface mapping can be utilized in the surgical visualization systems described herein. Structured light is the process of projecting a known pattern (often a grid or horizontal bars) on to a surface. In certain instances, invisible (or imperceptible) structured light can be utilized, in which the structured light is used without interfering with other computer vision tasks for which the projected pattern may be confusing. For example, infrared light or extremely fast frame rates of visible light that alternate between two exact opposite patterns can be utilized to prevent interference. Embodiments of surface mapping and a surgical system including a light source and a projector for projecting a light pattern are further described in U.S. Pat. Pub. No. 2017/0055819 entitled "Set Comprising A Surgical Instrument" published Mar. 2, 2017, U.S. Pat. Pub. No. 2017/0251900 entitled "Depiction System" published Sep. 7, 2017, and U.S. patent application Ser. No. 16/729,751 entitled "Surgical Systems For Generating Three Dimensional Constructs Of Anatomical Organs And Coupling Identified Anatomical Structures Thereto" filed Dec. 30, 2019, which are hereby incorporated by reference in their entireties.

The distance determining system can be incorporated into the surface mapping system. For example, structured light can be utilized to generate a three-dimensional (3D) virtual model of the visible surface 105 and determine various distances with respect to the visible surface 105. Additionally or alternatively, the distance determining system can rely on time-of-flight measurements to determine one or more distances to the identified tissue (or other structures) at the surgical site.

The surgical visualization system 100 also includes a surgical device 102. The surgical device 102 can be any suitable surgical device. Examples of the surgical device 102 includes a surgical dissector, a surgical stapler, a surgical grasper, a clip applier, a smoke evacuator, a surgical energy device (e.g., mono-polar probes, bi-polar probes, ablation probes, an ultrasound device, an ultrasonic end effector, etc.), etc. In some embodiments, the surgical device 102 includes an end effector having opposing jaws that extend from a distal end of a shaft of the surgical device 102 and that are configured to engage tissue therebetween.

The surgical visualization system 100 can be configured to identify the critical structure 101 and a proximity of the surgical device 102 to the critical structure 101. The imaging device 120 of the surgical visualization system 100 is configured to detect light at various wavelengths, such as visible light, spectral light waves (visible or invisible), and a structured light pattern (visible or invisible). The imaging device 120 can include a plurality of lenses, sensors, and/or receivers for detecting the different signals. For example, the imaging device 120 can be a hyperspectral, multispectral, or selective spectral camera, as described herein. The imaging device 120 can include a waveform sensor 122 (such as a spectral image sensor, detector, and/or three-dimensional camera lens). For example, the imaging device 120 can include a right-side lens and a left-side lens used together to record two two-dimensional images at the same time and, thus, generate a three-dimensional (3D) image of the surgical site, render a three-dimensional image of the surgical site, and/or determine one or more distances at the surgical site. Additionally or alternatively, the imaging device 120 can be configured to receive images indicative of the topography of the visible tissue and the identification and position of hidden critical structures, as further described herein. For example, a field of view of the imaging device 120 can overlap with a pattern of light (structured light) on the surface 105 of the tissue 103, as shown in FIG. 1.

As in this illustrated embodiment, the surgical visualization system 100 can be incorporated into a robotic surgical system 110. The robotic surgical system 110 can have a variety of configurations, as discussed herein. In this illustrated embodiment, the robotic surgical system 110 includes a first robotic arm 112 and a second robotic arm 114. The robotic arms 112, 114 each include rigid structural members 116 and joints 118, which can include servomotor controls. The first robotic arm 112 is configured to maneuver the surgical device 102, and the second robotic arm 114 is configured to maneuver the imaging device 120. A robotic control unit of the robotic surgical system 110 is configured to issue control motions to the first and second robotic arms 112, 114, which can affect the surgical device 102 and the imaging device 120, respectively.

In some embodiments, one or more of the robotic arms 112, 114 can be separate from the main robotic system 110 used in the surgical procedure. For example, at least one of the robotic arms 112, 114 can be positioned and registered to a particular coordinate system without a servomotor control. For example, a closed-loop control system and/or a plurality of sensors for the robotic arms 112, 114 can control and/or register the position of the robotic arm(s) 112, 114 relative to the particular coordinate system. Similarly, the position of the surgical device 102 and the imaging device 120 can be registered relative to a particular coordinate system.

Examples of robotic surgical systems include the Ottava™ robotic-assisted surgery system (Johnson & Johnson of New Brunswick, NJ), da Vinci® surgical systems (Intuitive Surgical, Inc. of Sunnyvale, CA), the Hugo™ robotic-assisted surgery system (Medtronic PLC of Minneapolis, MN), the Versius® surgical robotic system (CMR Surgical Ltd of Cambridge, UK), and the Monarch platform (Auris Health, Inc. of Redwood City, CA). Embodiments of various robotic surgical systems and using robotic surgical systems are further described in U.S. Pat. Pub. No. 2018/0177556 entitled "Flexible Instrument Insertion Using An Adaptive Force Threshold" filed Dec. 28, 2016, U.S. Pat. Pub. No. 2020/0000530 entitled "Systems And Techniques For Providing Multiple Perspectives During Medical Procedures" filed Apr. 16, 2019, U.S. Pat. Pub. No. 2020/0170720 entitled "Image-Based Branch Detection And Mapping For Navigation" filed Feb. 7, 2020, U.S. Pat. Pub. No. 2020/0188043 entitled "Surgical Robotics System" filed Dec. 9, 2019, U.S. Pat. Pub. No. 2020/0085516 entitled "Systems And Methods For Concomitant Medical Procedures" filed Sep. 3, 2019, U.S. Pat. No. 8,831,782 entitled "Patient-Side Surgeon Interface For A Teleoperated Surgical Instrument" filed Jul. 15, 2013, and Intl. Pat. Pub. No. WO 2014151621 entitled "Hyperdexterous Surgical System" filed Mar. 13, 2014, which are hereby incorporated by reference in their entireties.

The surgical visualization system 100 also includes an emitter 106. The emitter 106 is configured to emit a pattern of light, such as stripes, grid lines, and/or dots, to enable the determination of the topography or landscape of the surface 105. For example, projected light arrays 130 can be used for three-dimensional scanning and registration on the surface 105. The projected light arrays 130 can be emitted from the emitter 106 located on the surgical device 102 and/or one of the robotic arms 112, 114 and/or the imaging device 120. In one aspect, the projected light array 130 is employed by the surgical visualization system 100 to determine the shape defined by the surface 105 of the tissue 103 and/or motion of the surface 105 intraoperatively. The imaging device 120 is configured to detect the projected light arrays 130 reflected from the surface 105 to determine the topography of the surface 105 and various distances with respect to the surface 105.

As in this illustrated embodiment, the imaging device 120 can include an optical waveform emitter 123, such as by being mounted on or otherwise attached on the imaging device 120. The optical waveform emitter 123 is configured to emit electromagnetic radiation 124 (near-infrared (NIR) photons) that can penetrate the surface 105 of the tissue 103 and reach the critical structure 101. The imaging device 120 and the optical waveform emitter 123 can be positionable by the robotic arm 114. The optical waveform emitter 123 is mounted on or otherwise on the imaging device 122 but in other embodiments can be positioned on a separate surgical device from the imaging device 120. A corresponding waveform sensor 122 (e.g., an image sensor, spectrometer, or vibrational sensor) of the imaging device 120 is configured to detect the effect of the electromagnetic radiation received by the waveform sensor 122. The wavelengths of the electromagnetic radiation 124 emitted by the optical waveform emitter 123 are configured to enable the identification of the type of anatomical and/or physical structure, such as the critical structure 101. The identification of the critical structure 101 can be accomplished through spectral analysis, photo-acoustics, and/or ultrasound, for example. In one aspect, the wavelengths of the electromagnetic radiation 124 can be variable. The waveform sensor 122 and optical waveform emitter 123 can be inclusive of a multispectral imaging system and/or a selective spectral imaging system, for example. In other instances, the waveform sensor 122 and optical waveform emitter 123 can be inclusive of a photoacoustic imaging system, for example.

The distance sensor system 104 of the surgical visualization system 100 is configured to determine one or more distances at the surgical site. The distance sensor system 104 can be a time-of-flight distance sensor system that includes an emitter, such as the emitter 106 as in this illustrated embodiment, and that includes a receiver 108. In other instances, the time-of-flight emitter can be separate from the structured light emitter. The emitter 106 can include a very tiny laser source, and the receiver 108 can include a matching sensor. The distance sensor system 104 is configured to detect the "time of flight," or how long the laser light emitted by the emitter 106 has taken to bounce back to the sensor portion of the receiver 108. Use of a very narrow light source in the emitter 106 enables the distance sensor system 104 to determining the distance to the surface 105 of the tissue 103 directly in front of the distance sensor system 104.

The receiver 108 of the distance sensor system 104 is positioned on the surgical device 102 in this illustrated embodiment, but in other embodiments the receiver 108 can be mounted on a separate surgical device instead of the surgical device 102. For example, the receiver 108 can be mounted on a cannula or trocar through which the surgical device 102 extends to reach the surgical site. In still other embodiments, the receiver 108 for the distance sensor system 104 can be mounted on a separate robotically-controlled arm of the robotic system 110 (e.g., on the second robotic arm 114) than the first robotic arm 112 to which the surgical device 102 is coupled, can be mounted on a movable arm that is operated by another robot, or be mounted to an operating room (OR) table or fixture. In some embodiments, the imaging device 120 includes the receiver 108 to allow for determining the distance from the emitter 106 to the surface 105 of the tissue 103 using a line between the emitter 106 on the surgical device 102 and the imaging device 120. For example, the distance $d_e$ can be triangulated based on known positions of the emitter 106 (on the surgical device 102) and the receiver 108 (on the imaging device 120) of the distance sensor system 104. The three-dimensional position of the receiver 108 can be known and/or registered to the robot coordinate plane intraoperatively.

As in this illustrated embodiment, the position of the emitter 106 of the distance sensor system 104 can be controlled by the first robotic arm 112, and the position of the receiver 108 of the distance sensor system 104 can be controlled by the second robotic arm 114. In other embodiments, the surgical visualization system 100 can be utilized apart from a robotic system. In such instances, the distance sensor system 104 can be independent of the robotic system.

In FIG. 1, $d_e$ is emitter-to-tissue distance from the emitter 106 to the surface 105 of the tissue 103, and $d_t$ is device-to-tissue distance from a distal end of the surgical device 102 to the surface 105 of the tissue 103. The distance sensor system 104 is configured to determine the emitter-to-tissue distance $d_e$. The device-to-tissue distance $d_e$ is obtainable from the known position of the emitter 106 on the surgical device 102, e.g., on a shaft thereof proximal to the surgical device's distal end, relative to the distal end of the surgical device 102. In other words, when the distance between the emitter 106 and the distal end of the surgical device 102 is known, the device-to-tissue distance di can be determined from the emitter-to-tissue distance $d_e$. In some embodiments, the shaft of the surgical device 102 can include one or more articulation joints and can be articulatable with respect to the emitter 106 and jaws at the distal end of the surgical device 102. The articulation configuration can include a multi-joint vertebrae-like structure, for example. In some embodiments, a three-dimensional camera can be utilized to triangulate one or more distances to the surface 105.

In FIG. 1, $d_w$ is camera-to-critical structure distance from the optical waveform emitter 123 located on the imaging device 120 to the surface of the critical structure 101, and $d_A$ is a depth of the critical structure 101 below the surface 105 of the tissue 103 (e.g., the distance between the portion of the surface 105 closest to the surgical device 102 and the critical structure 101). The time-of-flight of the optical waveforms emitted from the optical waveform emitter 123 located on the imaging device 120 are configured to determine the camera-to-critical structure distance $d_w$.

Figure 2:
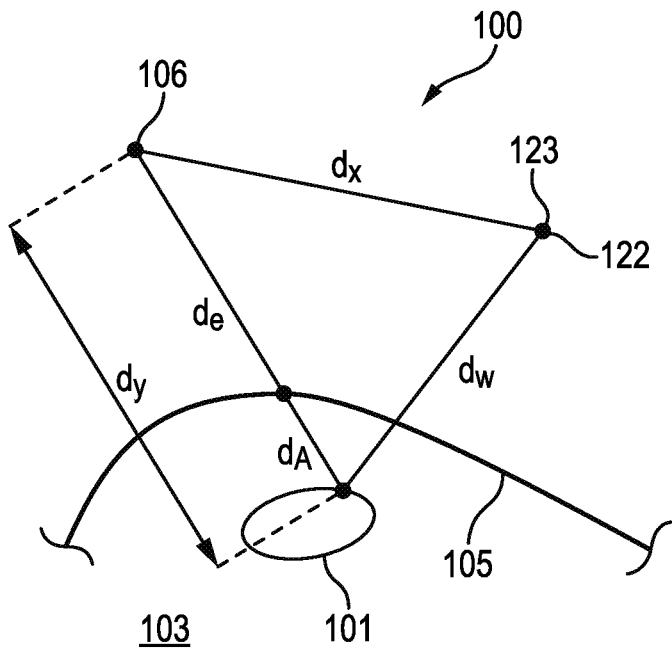
FIG. 2 is a schematic view of triangularization between a surgical device, an imaging device, and a critical structure of FIG. 1.

As shown in FIG. 2, the depth $d_A$ of the critical structure 101 relative to the surface 105 of the tissue 103 can be determined by triangulating from the distance $d_w$ and known positions of the emitter 106 on the surgical device 102 and the optical waveform emitter 123 on the imaging device 120 (and, thus, the known distance $d_x$ therebetween) to determine the distance $d_y$, which is the sum of the distances $d_e$ and $d_A$. Additionally or alternatively, time-of-flight from the optical waveform emitter 123 can be configured to determine the distance from the optical waveform emitter 123 to the surface 105 of the tissue 103. For example, a first waveform (or range of waveforms) can be utilized to determine the camera-to-critical structure distance $d_w$ and a second waveform (or range of waveforms) can be utilized to determine the distance to the surface 105 of the tissue 103. In such instances, the different waveforms can be utilized to determine the depth of the critical structure 101 below the surface 105 of the tissue 103.

Additionally or alternatively, the distance $d_A$ can be determined from an ultrasound, a registered magnetic resonance imaging (MRI), or computerized tomography (CT) scan. In still other instances, the distance $d_A$ can be determined with spectral imaging because the detection signal received by the imaging device 120 can vary based on the type of material, e.g., type of the tissue 103. For example, fat can decrease the detection signal in a first way, or a first amount, and collagen can decrease the detection signal in a different, second way, or a second amount.

Figure 3:
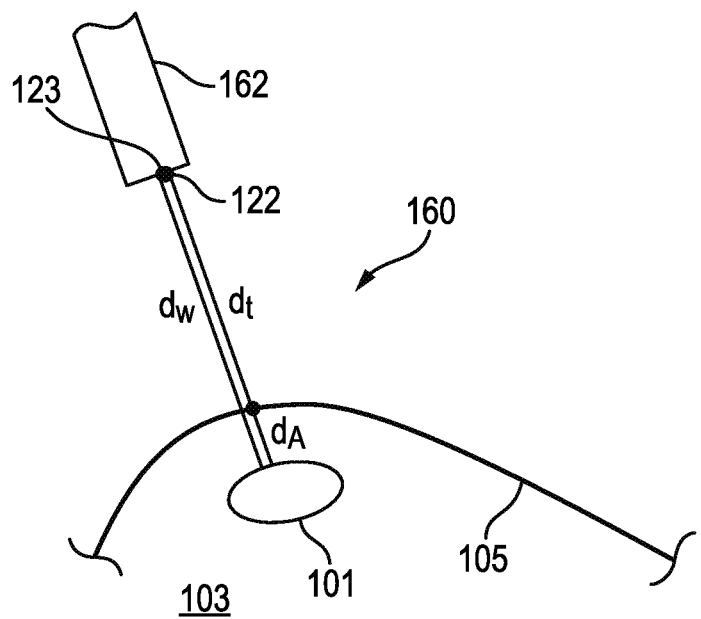
FIG. 3 is a schematic view of another embodiment of a surgical visualization system.

In another embodiment of a surgical visualization system 160 illustrated in FIG. 3, a surgical device 162, and not the imaging device 120, includes the optical waveform emitter 123 and the waveform sensor 122 that is configured to detect the reflected waveforms. The optical waveform emitter 123 is configured to emit waveforms for determining the distances $d_e$ and $d_w$ from a common device, such as the surgical device 162, as described herein. In such instances, the distance $d_A$ from the surface 105 of the tissue 103 to the surface of the critical structure 101 can be determined as follows:

$$d_A = d_w - d_t$$

Figure 4:
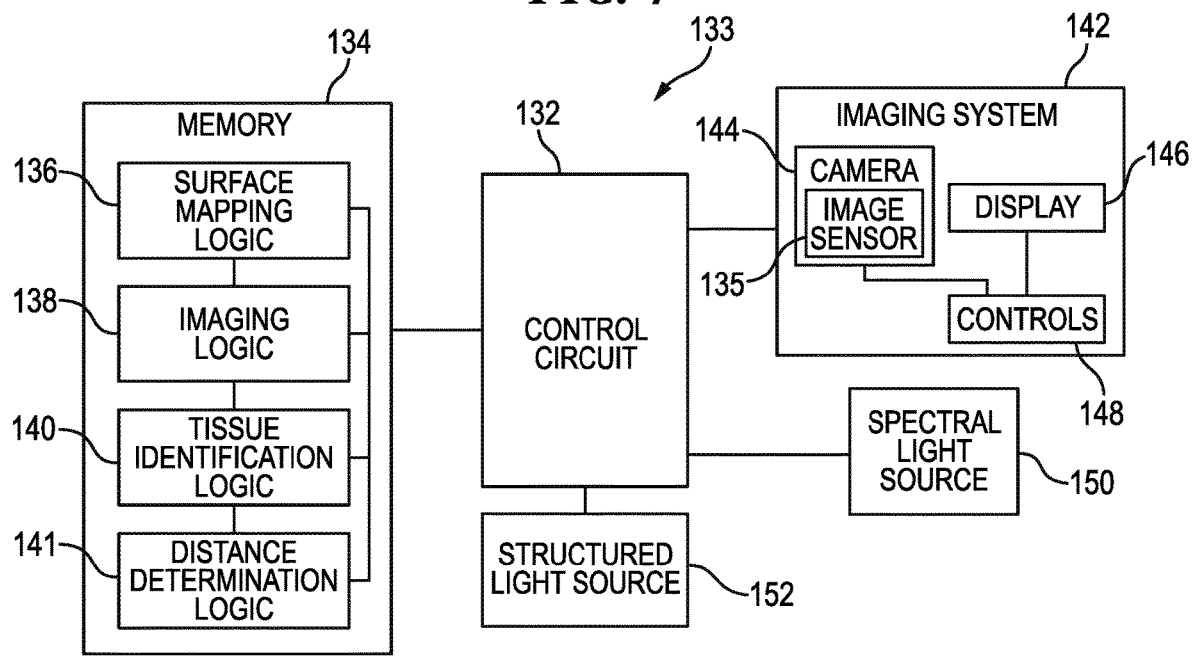
FIG. 4 is a schematic view of one embodiment of a control system for a surgical visualization system.

The surgical visualization system 100 includes a control system configured to control various aspects of the surgical visualization system 100. FIG. 4 illustrates one embodiment of a control system 133 that can be utilized as the control system of the surgical visualization system 100 (or other surgical visualization system described herein). The control system 133 includes a control circuit 132 configured to be in signal communication with a memory 134. The memory 134 is configured to store instructions executable by the control circuit 132, such as instructions to determine and/or recognize critical structures (e.g., the critical structure 101 of FIG. 1), instructions to determine and/or compute one or more distances and/or three-dimensional digital representations, and instructions to communicate information to a medical practitioner. As in this illustrated embodiment, the memory 134 can store surface mapping logic 136, imaging logic 138, tissue identification logic 140, and distance determining logic 141, although the memory 134 can store any combinations of the logics 136, 138, 140, 141 and/or can combine various logics together. The control system 133 also includes an imaging system 142 including a camera 144 (e.g., the imaging system including the imaging device 120 of FIG. 1), a display 146 (e.g., a monitor, a computer tablet screen, etc.), and controls 148 of the camera 144 and the display 146. The camera 144 includes an image sensor 135 (e.g., the waveform sensor 122) configured to receive signals from various light sources emitting light at various visible and invisible spectra (e.g., visible light, spectral imagers, three-dimensional lens, etc.). The display 146 is configured to depict real, virtual, and/or virtually-augmented images and/or information to a medical practitioner.

In an exemplary embodiment, the image sensor 135 is a solid-state electronic device containing up to millions of discrete photodetector sites called pixels. The image sensor 135 technology falls into one of two categories: Charge-Coupled Device (CCD) and Complementary Metal Oxide Semiconductor (CMOS) imagers and more recently, short-wave infrared (SWIR) is an emerging technology in imaging. Another type of the image sensor 135 employs a hybrid CCD/CMOS architecture (sold under the name "sCMOS") and consists of CMOS readout integrated circuits (ROICs) that are bump bonded to a CCD imaging substrate. CCD and CMOS image sensors 135 are sensitive to wavelengths in a range of about 350 nm to about 1050 nm, such as in a range of about 400 nm to about 1000 nm. A person skilled in the art will appreciate that a value may not be precisely at a value but nevertheless considered to be about that value for any of a variety of reasons, such as sensitivity of measurement equipment and manufacturing tolerances. CMOS sensors are, in general, more sensitive to IR wavelengths than CCD sensors. Solid state image sensors 135 are based on the photoelectric effect and, as a result, cannot distinguish between colors. Accordingly, there are two types of color CCD cameras: single chip and three-chip. Single chip color CCD cameras offer a common, low-cost imaging solution and use a mosaic (e.g., Bayer) optical filter to separate incoming light into a series of colors and employ an interpolation algorithm to resolve full color images. Each color is, then, directed to a different set of pixels. Three-chip color CCD cameras provide higher resolution by employing a prism to direct each section of the incident spectrum to a different chip. More accurate color reproduction is possible, as each point in space of the object has separate RGB intensity values, rather than using an algorithm to determine the color. Three-chip cameras offer extremely high resolutions.

The control system 133 also includes an emitter (e.g., the emitter 106) including a spectral light source 150 and a structured light source 152 each operably coupled to the control circuit 133. A single source can be pulsed to emit wavelengths of light in the spectral light source 150 range and wavelengths of light in the structured light source 152 range. Alternatively, a single light source can be pulsed to provide light in the invisible spectrum (e.g., infrared spectral light) and wavelengths of light on the visible spectrum. The spectral light source 150 can be, for example, a hyperspectral light source, a multispectral light source, and/or a selective spectral light source. The tissue identification logic 140 is configured to identify critical structure(s) (e.g., the critical structure 101 of FIG. 1) via data from the spectral light source 150 received by the image sensor 135 of the camera 144. The surface mapping logic 136 is configured to determine the surface contours of the visible tissue (e.g., the tissue 103) based on reflected structured light. With time-of-flight measurements, the distance determining logic 141 is configured to determine one or more distance(s) to the visible tissue and/or the critical structure. Output from each of the surface mapping logic 136, the tissue identification logic 140, and the distance determining logic 141 is configured to be provided to the imaging logic 138, and combined, blended, and/or overlaid by the imaging logic 138 to be conveyed to a medical practitioner via the display 146 of the imaging system 142.

Figure 5:
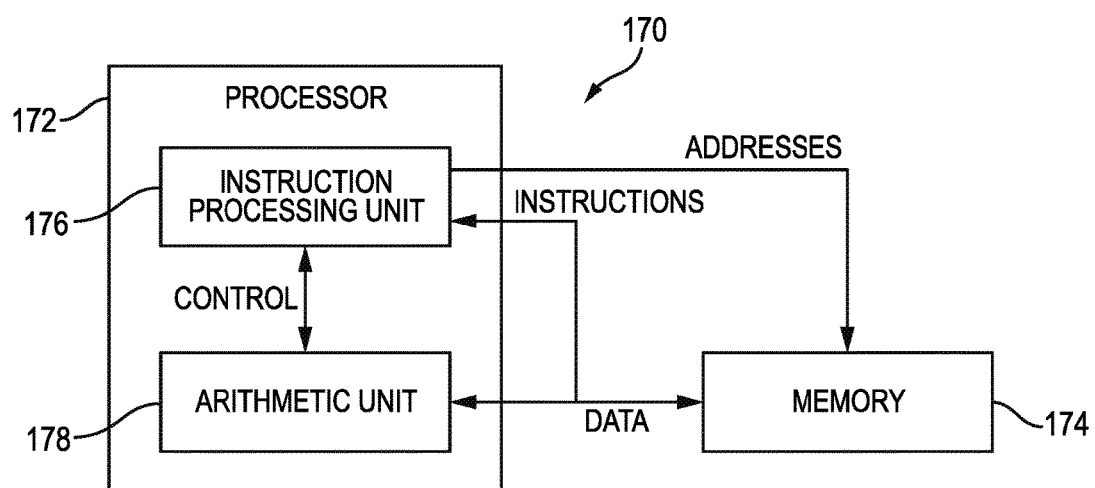
FIG. 5 is a schematic view of one embodiment of a control circuit of a control system for a surgical visualization system.

The control circuit 132 can have a variety of configurations. FIG. 5 illustrates one embodiment of a control circuit 170 that can be used as the control circuit 132 configured to control aspects of the surgical visualization system 100. The control circuit 170 is configured to implement various processes described herein. The control circuit 170 includes a microcontroller that includes a processor 172 (e.g., a microprocessor or microcontroller) operably coupled to a memory 174. The memory 174 is configured to store machine-executable instructions that, when executed by the processor 172, cause the processor 172 to execute machine instructions to implement various processes described herein. The processor 172 can be any one of a number of single-core or multicore processors known in the art. The memory 174 can include volatile and non-volatile storage media. The processor 172 includes an instruction processing unit 176 and an arithmetic unit 178. The instruction processing unit 176 is configured to receive instructions from the memory 174.

Figure 6:
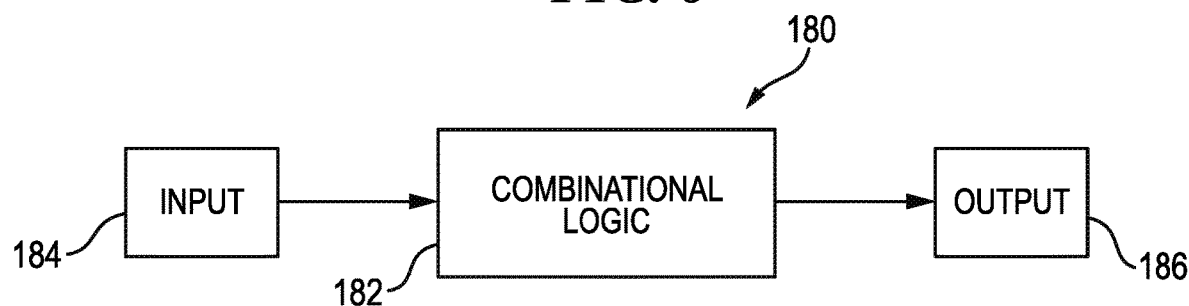
FIG. 6 is a schematic view of one embodiment of a combinational logic circuit of a surgical visualization system.

The surface mapping logic 136, the imaging logic 138, the tissue identification logic 140, and the distance determining logic 141 can have a variety of configurations. FIG. 6 illustrates one embodiment of a combinational logic circuit 180 configured to control aspects of the surgical visualization system 100 using logic such as one or more of the surface mapping logic 136, the imaging logic 138, the tissue identification logic 140, and the distance determining logic 141. The combinational logic circuit 180 includes a finite state machine that includes a combinational logic 182 configured to receive data associated with a surgical device (e.g. the surgical device 102 and/or the imaging device 120) at an input 184, process the data by the combinational logic 182, and provide an output 184 to a control circuit (e.g., the control circuit 132).

Figure 7:
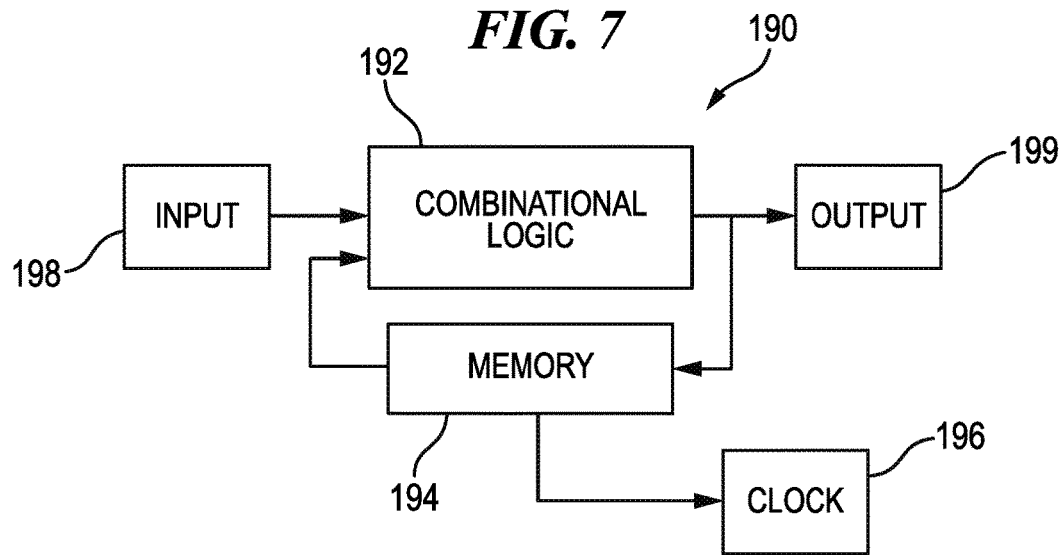
FIG. 7 is a schematic view of one embodiment of a sequential logic circuit of a surgical visualization system.

FIG. 7 illustrates one embodiment of a sequential logic circuit 190 configured to control aspects of the surgical visualization system 100 using logic such as one or more of the surface mapping logic 136, the imaging logic 138, the tissue identification logic 140, and the distance determining logic 141. The sequential logic circuit 190 includes a finite state machine that includes a combinational logic 192, a memory 194, and a clock 196. The memory 194 is configured to store a current state of the finite state machine. The sequential logic circuit 190 can be synchronous or asynchronous. The combinational logic 192 is configured to receive data associated with a surgical device (e.g. the surgical device 102 and/or the imaging device 120) at an input 426, process the data by the combinational logic 192, and provide an output 499 to a control circuit (e.g., the control circuit 132). In some embodiments, the sequential logic circuit 190 can include a combination of a processor (e.g., processor 172 of FIG. 5) and a finite state machine to implement various processes herein. In some embodiments, the finite state machine can include a combination of a combinational logic circuit (e.g., the combinational logic circuit 192 of FIG. 7) and the sequential logic circuit 190.

Figure 8:
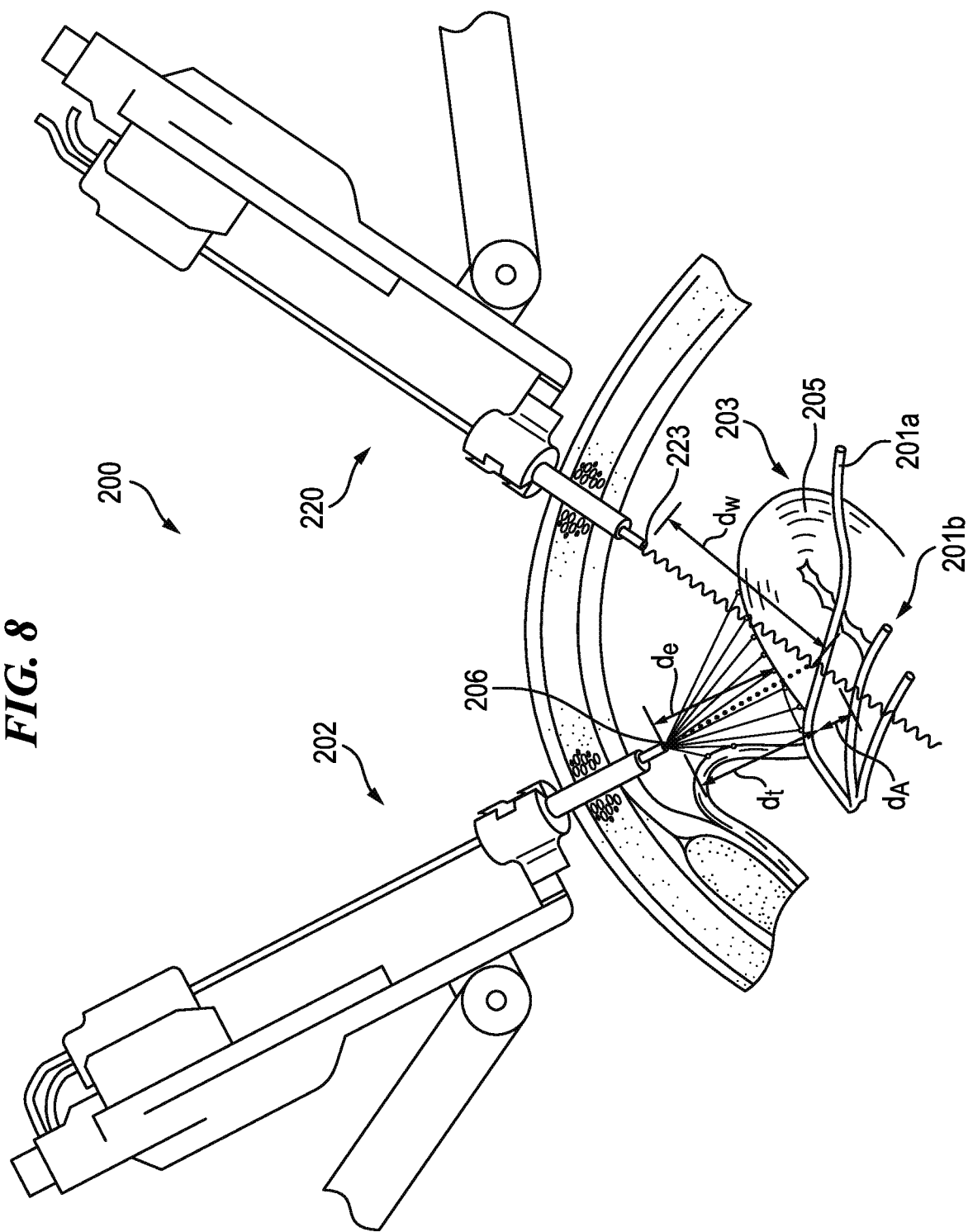
FIG. 8 is a schematic view of yet another embodiment of a surgical visualization system.

FIG. 8 illustrates another embodiment of a surgical visualization system 200. The surgical visualization system 200 is generally configured and used similar to the surgical visualization system 100 of FIG. 1, e.g., includes a surgical device 202 and an imaging device 220. The imaging device 220 includes a spectral light emitter 223 configured to emit spectral light in a plurality of wavelengths to obtain a spectral image of hidden structures, for example. The imaging device 220 can also include a three-dimensional camera and associated electronic processing circuits. The surgical visualization system 200 is shown being utilized intraoperatively to identify and facilitate avoidance of certain critical structures, such as a ureter 201a and vessels 201b, in an organ 203 (a uterus in this embodiment) that are not visible on a surface 205 of the organ 203.

The surgical visualization system 200 is configured to determine an emitter-to-tissue distance $d_e$ from an emitter 206 on the surgical device 202 to the surface 205 of the uterus 203 via structured light. The surgical visualization system 200 is configured to extrapolate a device-to-tissue distance $d_e$ from the surgical device 202 to the surface 205 of the uterus 203 based on the emitter-to-tissue distance $d_e$. The surgical visualization system 200 is also configured to determine a tissue-to-ureter distance $d_A$ from the ureter 201a to the surface 205 and a camera—to ureter distance $d_w$ from the imaging device 220 to the ureter 201a. As described herein, e.g., with respect to the surgical visualization system 100 of FIG. 1, the surgical visualization system 200 is configured to determine the distance $d_w$ with spectral imaging and time-of-flight sensors, for example. In various embodiments, the surgical visualization system 200 can determine (e.g. triangulate) the tissue-to-ureter distance $d_A$ (or depth) based on other distances and/or the surface mapping logic described herein.

Figure 9:
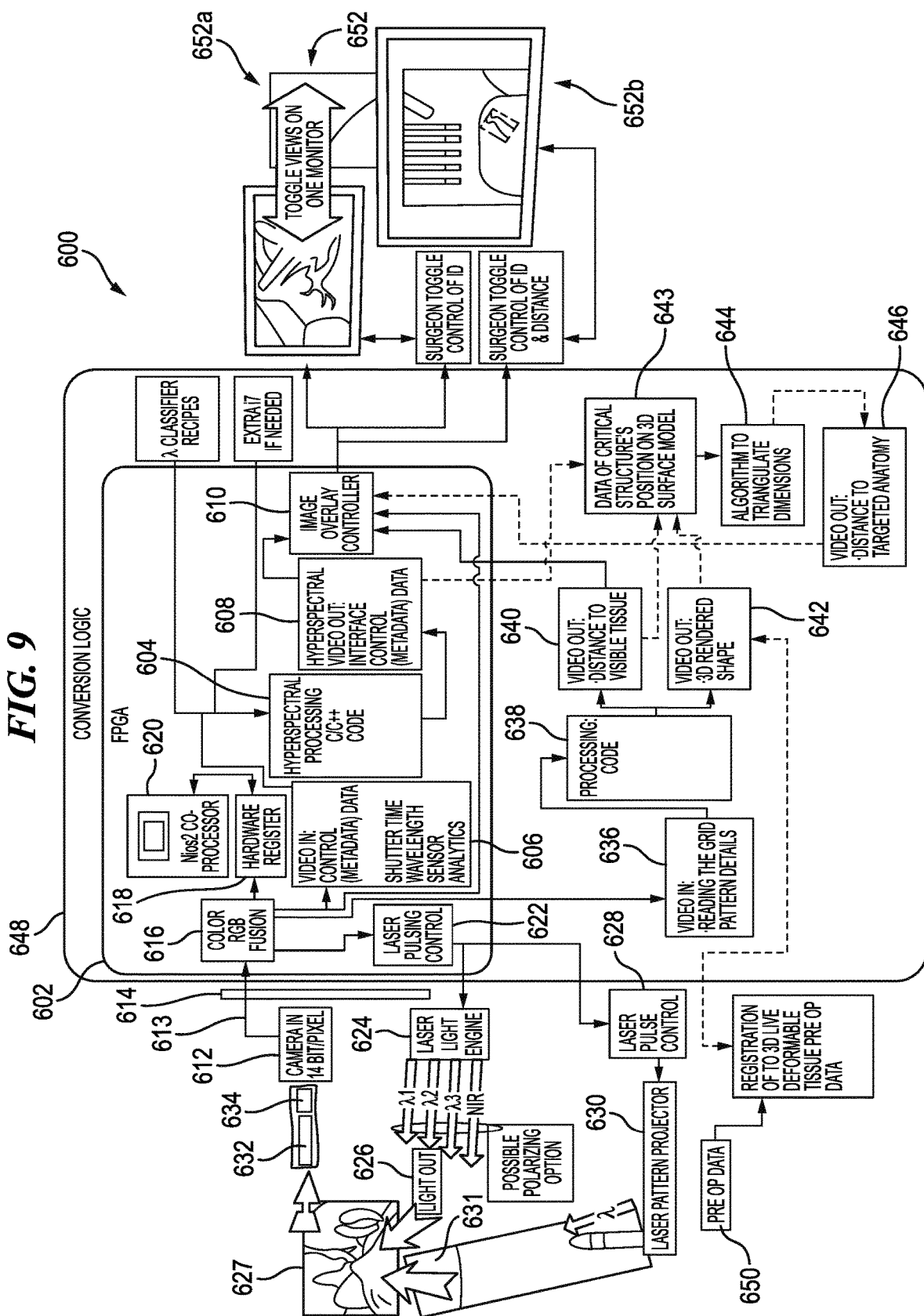
FIG. 9 is a schematic view of another embodiment of a control system for a surgical visualization system.

As mentioned above, a surgical visualization system includes a control system configured to control various aspects of the surgical visualization system. The control system can have a variety of configurations. FIG. 9 illustrates one embodiment of a control system 600 for a surgical visualization system, such as the surgical visualization system 100 of FIG. 1, the surgical visualization system 200 of FIG. 8, or other surgical visualization system described herein. The control system 600 is a conversion system that integrates spectral signature tissue identification and structured light tissue positioning to identify a critical structure, especially when those structure(s) are obscured by tissue, e.g., by fat, connective tissue, blood tissue, and/or organ(s), and/or by blood, and/or to detect tissue variability, such as differentiating tumors and/or non-healthy tissue from healthy tissue within an organ.

The control system 600 is configured for implementing a hyperspectral imaging and visualization system in which a molecular response is utilized to detect and identify anatomy in a surgical field of view. The control system 600 includes a conversion logic circuit 648 configured to convert tissue data to usable information for surgeons and/or other medical practitioners. For example, variable reflectance based on wavelengths with respect to obscuring material can be utilized to identify the critical structure in the anatomy. Moreover, the control system 600 is configured to combine the identified spectral signature and the structural light data in an image. For example, the control system 600 can be employed to create of three-dimensional data set for surgical use in a system with augmentation image overlays. Techniques can be employed both intraoperatively and preoperatively using additional visual information. In various embodiments, the control system 600 is configured to provide warnings to a medical practitioner when in the proximity of one or more critical structures. Various algorithms can be employed to guide robotic automation and semi-automated approaches based on the surgical procedure and proximity to the critical structure(s).

A projected array of lights is employed by the control system 600 to determine tissue shape and motion intraoperatively. Alternatively, flash Lidar may be utilized for surface mapping of the tissue.

The control system 600 is configured to detect the critical structure, which as mentioned above can include one or more critical structures, and provide an image overlay of the critical structure and measure the distance to the surface of the visible tissue and the distance to the embedded/buried critical structure(s). The control system 600 can measure the distance to the surface of the visible tissue or detect the critical structure and provide an image overlay of the critical structure.

The control system 600 includes a spectral control circuit 602. The spectral control circuit 602 can be a field programmable gate array (FPGA) or another suitable circuit configuration, such as the configurations described with respect to FIG. 6, FIG. 7, and FIG. 8. The spectral control circuit 602 includes a processor 604 configured to receive video input signals from a video input processor 606. The processor 604 can be configured for hyperspectral processing and can utilize C/C++ code, for example. The video input processor 606 is configured to receive video-in of control (metadata) data such as shutter time, wave length, and sensor analytics, for example. The processor 604 is configured to process the video input signal from the video input processor 606 and provide a video output signal to a video output processor 608, which includes a hyperspectral video-out of interface control (metadata) data, for example. The video output processor 608 is configured to provides the video output signal to an image overlay controller 610.

The video input processor 606 is operatively coupled to a camera 612 at the patient side via a patient isolation circuit 614. The camera 612 includes a solid state image sensor 634. The patient isolation circuit 614 can include a plurality of transformers so that the patient is isolated from other circuits in the system. The camera 612 is configured to receive intraoperative images through optics 632 and the image sensor 634. The image sensor 634 can include a CMOS image sensor, for example, or can include another image sensor technology, such as those discussed herein in connection with FIG. 4. The camera 612 is configured to output 613 images in 14 bit/pixel signals. A person skilled in the art will appreciate that higher or lower pixel resolutions can be employed. The isolated camera output signal 613 is provided to a color RGB fusion circuit 616, which in this illustrated embodiment employs a hardware register 618 and a Nios2 co-processor 620 configured to process the camera output signal 613. A color RGB fusion output signal is provided to the video input processor 606 and a laser pulsing control circuit 622.

The laser pulsing control circuit 622 is configured to control a laser light engine 624. The laser light engine 624 is configured to output light in a plurality of wavelengths (21, 22, 23 . . . An) including near infrared (NIR). The laser light engine 624 can operate in a plurality of modes. For example, the laser light engine 624 can operate in two modes. In a first mode, e.g., a normal operating mode, the laser light engine 624 is configured to output an illuminating signal. In a second mode, e.g., an identification mode, the laser light engine 624 is configured to output RGBG and NIR light. In various embodiments, the laser light engine 624 can operate in a polarizing mode.

Light output 626 from the laser light engine 624 is configured to illuminate targeted anatomy in an intraoperative surgical site 627. The laser pulsing control circuit 622 is also configured to control a laser pulse controller 628 for a laser pattern projector 630 configured to project a laser light pattern 631, such as a grid or pattern of lines and/or dots, at a predetermined wavelength (22) on an operative tissue or organ at the surgical site 627. The camera 612 is configured to receive the patterned light as well as the reflected light output through the camera optics 632. The image sensor 634 is configured to convert the received light into a digital signal.

The color RGB fusion circuit 616 is also configured to output signals to the image overlay controller 610 and a video input module 636 for reading the laser light pattern 631 projected onto the targeted anatomy at the surgical site 627 by the laser pattern projector 630. A processing module 638 is configured to process the laser light pattern 631 and output a first video output signal 640 representative of the distance to the visible tissue at the surgical site 627. The data is provided to the image overlay controller 610. The processing module 638 is also configured to output a second video signal 642 representative of a three-dimensional rendered shape of the tissue or organ of the targeted anatomy at the surgical site.

The first and second video output signals 640, 642 include data representative of the position of the critical structure on a three-dimensional surface model, which is provided to an integration module 643. In combination with data from the video out processor 608 of the spectral control circuit 602, the integration module 643 is configured to determine the distance (e.g., distance $d_A$ of FIG. 1) to a buried critical structure (e.g., via triangularization algorithms 644), and the distance to the buried critical structure can be provided to the image overlay controller 610 via a video out processor 646. The foregoing conversion logic can encompass the conversion logic circuit 648 intermediate video monitors 652 and the camera 624/laser pattern projector 630 positioned at the surgical site 627.

Preoperative data 650, such as from a CT or MRI scan, can be employed to register or align certain three-dimensional deformable tissue in various instances. Such preoperative data 650 can be provided to the integration module 643 and ultimately to the image overlay controller 610 so that such information can be overlaid with the views from the camera 612 and provided to the video monitors 652. Embodiments of registration of preoperative data are further described in U.S. Pat. Pub. No. 2020/0015907 entitled "Integration Of Imaging Data" filed Sep. 11, 2018, which is hereby incorporated by reference herein in its entirety.

The video monitors 652 are configured to output the integrated/augmented views from the image overlay controller 610. A medical practitioner can select and/or toggle between different views on one or more displays. On a first display 652a, which is a monitor in this illustrated embodiment, the medical practitioner can toggle between (A) a view in which a three-dimensional rendering of the visible tissue is depicted and (B) an augmented view in which one or more hidden critical structures are depicted over the three-dimensional rendering of the visible tissue. On a second display 652b, which is a monitor in this illustrated embodiment, the medical practitioner can toggle on distance measurements to one or more hidden critical structures and/or the surface of visible tissue, for example.

The various surgical visualization systems described herein can be utilized to visualize various different types of tissues and/or anatomical structures, including tissues and/or anatomical structures that may be obscured from being visualized by EMR in the visible portion of the spectrum. The surgical visualization system can utilize a spectral imaging system, as mentioned above, which can be configured to visualize different types of tissues based upon their varying combinations of constituent materials. In particular, a spectral imaging system can be configured to detect the presence of various constituent materials within a tissue being visualized based on the absorption coefficient of the tissue across various EMR wavelengths. The spectral imaging system can be configured to characterize the tissue type of the tissue being visualized based upon the particular combination of constituent materials.

Figure 10:
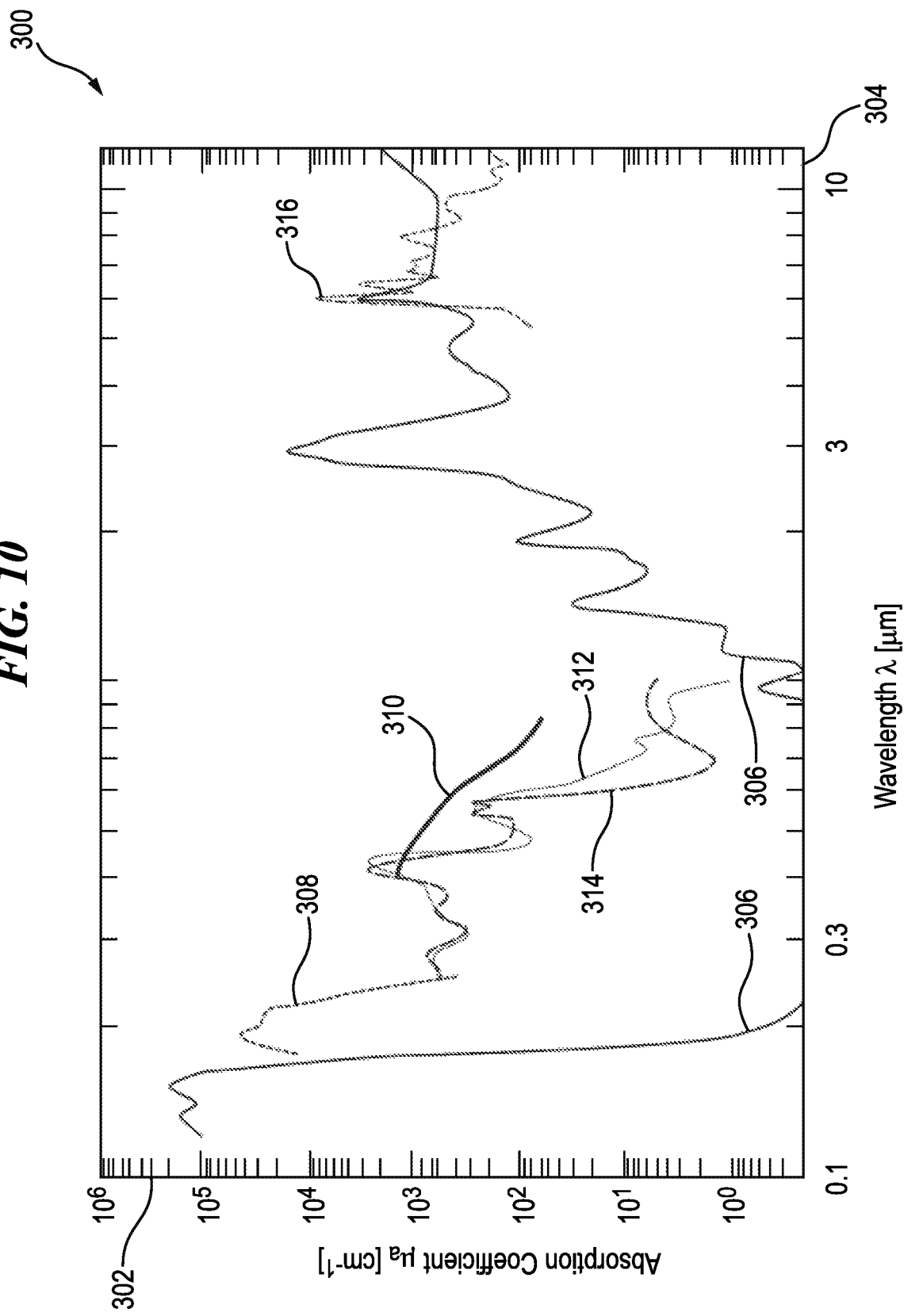
FIG. 10 is a graph showing wavelength versus absorption coefficient for various biological materials.

FIG. 10 shows a graph 300 depicting how the absorption coefficient of various biological materials varies across the EMR wavelength spectrum. In the graph 300, the vertical axis 302 represents absorption coefficient of the biological material in $cm^{-1}$, and the horizontal axis 304 represents EMR wavelength in µm. A first line 306 in the graph 300 represents the absorption coefficient of water at various EMR wavelengths, a second line 308 represents the absorption coefficient of protein at various EMR wavelengths, a third line 310 represents the absorption coefficient of melanin at various EMR wavelengths, a fourth line 312 represents the absorption coefficient of deoxygenated hemoglobin at various EMR wavelengths, a fifth line 314 represents the absorption coefficient of oxygenated hemoglobin at various EMR wavelengths, and a sixth line 316 represents the absorption coefficient of collagen at various EMR wavelengths. Different tissue types have different combinations of constituent materials and, therefore, the tissue type(s) being visualized by a surgical visualization system can be identified and differentiated between according to the particular combination of detected constituent materials. Accordingly, a spectral imaging system of a surgical visualization system can be configured to emit EMR at a number of different wavelengths, determine the constituent materials of the tissue based on the detected absorption EMR absorption response at the different wavelengths, and then characterize the tissue type based on the particular detected combination of constituent materials.

Figure 11:
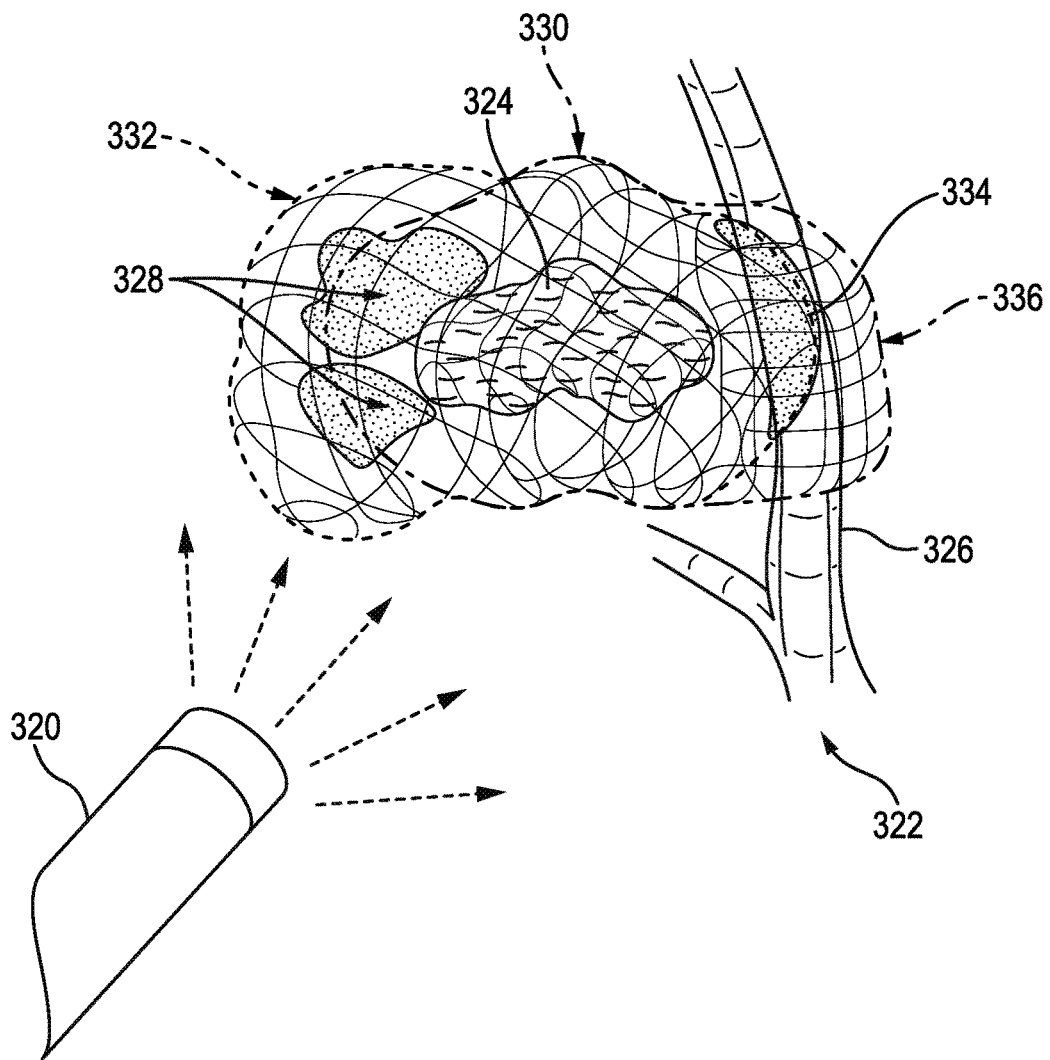
FIG. 11 is a schematic view of one embodiment of a spectral emitter visualizing a surgical site.

FIG. 11 shows an embodiment of the utilization of spectral imaging techniques to visualize different tissue types and/or anatomical structures. In FIG. 11, a spectral emitter 320 (e.g., the spectral light source 150 of FIG. 4) is being utilized by an imaging system to visualize a surgical site 322. The EMR emitted by the spectral emitter 320 and reflected from the tissues and/or structures at the surgical site 322 is received by an image sensor (e.g., the image sensor 135 of FIG. 4) to visualize the tissues and/or structures, which can be either visible (e.g., be located at a surface of the surgical site 322) or obscured (e.g., underlay other tissue and/or structures at the surgical site 322). In this embodiment, an imaging system (e.g., the imaging system 142 of FIG. 4) visualizes a tumor 324, an artery 326, and various abnormalities 328 (e.g., tissues not confirming to known or expected spectral signatures) based upon the spectral signatures characterized by the differing absorptive characteristics (e.g., absorption coefficient) of the constituent materials for each of the different tissue/structure types. The visualized tissues and structures can be displayed on a display screen associated with or coupled to the imaging system (e.g., the display 146 of the imaging system 142 of FIG. 4), on a primary display (e.g., the primary display 819 of FIG. 19), on a non-sterile display (e.g., the non-sterile displays 807, 809 of FIG. 19), on a display of a surgical hub (e.g., the display of the surgical hub 806 of FIG. 19), on a device/instrument display, and/or on another display.

The imaging system can be configured to tailor or update the displayed surgical site visualization according to the identified tissue and/or structure types. For example, as shown in FIG. 11, the imaging system can display a margin 330 associated with the tumor 324 being visualized on a display screen associated with or coupled to the imaging system, on a primary display, on a non-sterile display, on a display of a surgical hub, on a device/instrument display, and/or on another display. The margin 330 can indicate the area or amount of tissue that should be excised to ensure complete removal of the tumor 324. The surgical visualization system's control system (e.g., the control system 133 of FIG. 4) can be configured to control or update the dimensions of the margin 330 based on the tissues and/or structures identified by the imaging system. In this illustrated embodiment, the imaging system has identified multiple abnormalities 328 within the field of view (FOV). Accordingly, the control system can adjust the displayed margin 330 to a first updated margin 332 having sufficient dimensions to encompass the abnormalities 328. Further, the imaging system has also identified the artery 326 partially overlapping with the initially displayed margin 330 (as indicated by a highlighted region 334 of the artery 326). Accordingly, the control system can adjust the displayed margin to a second updated margin 336 having sufficient dimensions to encompass the relevant portion of the artery 326.

Figure 12:
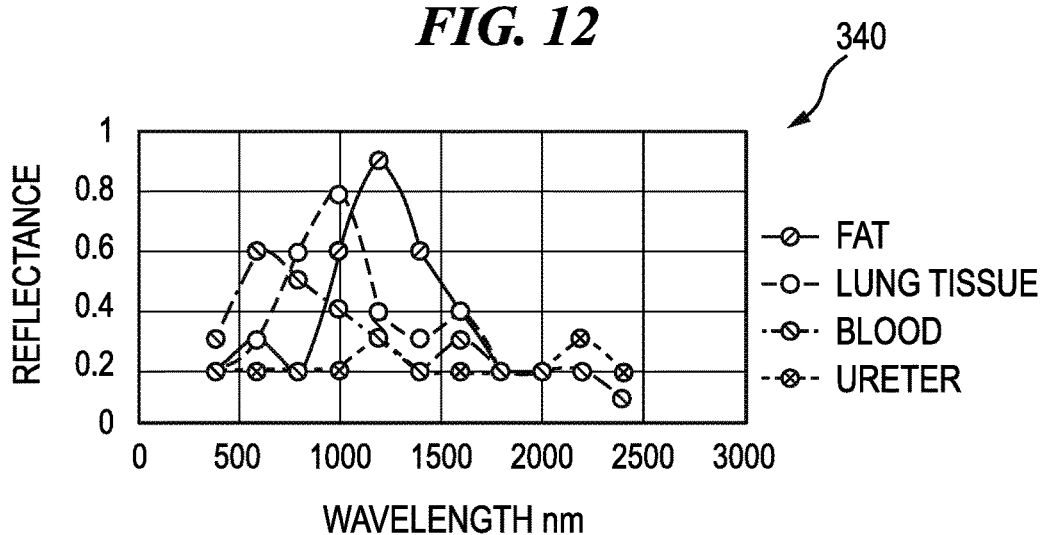
FIG. 12 is a graph depicting illustrative hyperspectral identifying signatures to differentiate a ureter from obscurants.
Figure 13:
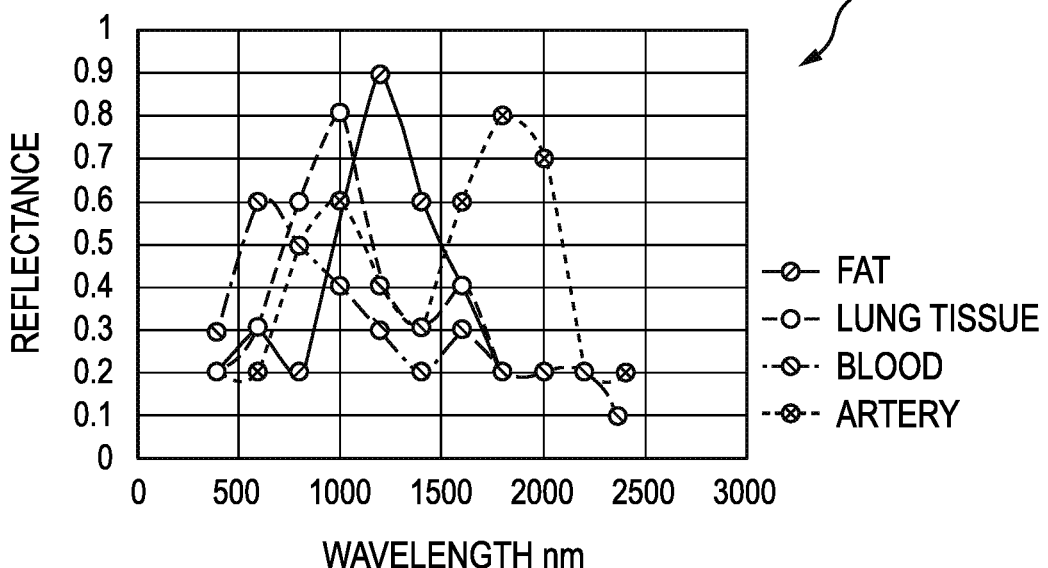
FIG. 13 is a graph depicting illustrative hyperspectral identifying signatures to differentiate an artery from obscurants.
Figure 14:
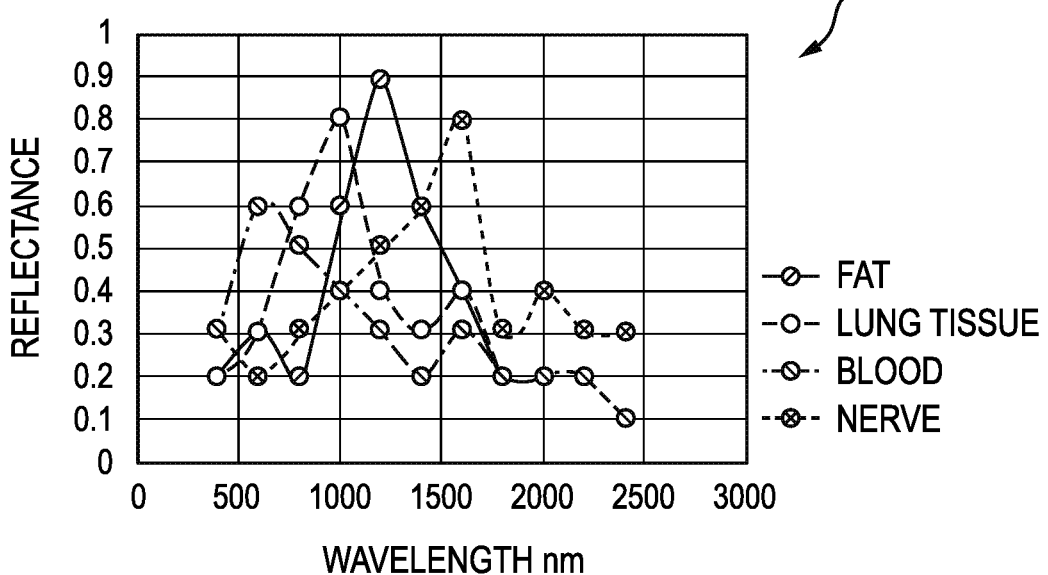
FIG. 14 is a graph depicting illustrative hyperspectral identifying signatures to differentiate a nerve from obscurants.

Tissues and/or structures can also be imaged or characterized according to their reflective characteristics, in addition to or in lieu of their absorptive characteristics described above with respect to FIG. 10 and FIG. 11, across the EMR wavelength spectrum. For example, FIG. 12, FIG. 13, and FIG. 14 illustrate various graphs of reflectance of different types of tissues or structures across different EMR wavelengths. FIG. 12 is a graphical representation 340 of an illustrative ureter signature versus obscurants. FIG. 13 is a graphical representation 342 of an illustrative artery signature versus obscurants. FIG. 14 is a graphical representation 344 of an illustrative nerve signature versus obscurants. The plots in FIG. 12, FIG. 13, and FIG. 14 represent reflectance as a function of wavelength (nm) for the particular structures (ureter, artery, and nerve) relative to the corresponding reflectances of fat, lung tissue, and blood at the corresponding wavelengths. These graphs are simply for illustrative purposes and it should be understood that other tissues and/or structures could have corresponding detectable reflectance signatures that would allow the tissues and/or structures to be identified and visualized.

Select wavelengths for spectral imaging can be identified and utilized based on the anticipated critical structures and/or obscurants at a surgical site (e.g., "selective spectral" imaging). By utilizing selective spectral imaging, the amount of time required to obtain the spectral image can be minimized such that the information can be obtained in real-time and utilized intraoperatively. The wavelengths can be selected by a medical practitioner or by a control circuit based on input by a user, e.g., a medical practitioner. In certain instances, the wavelengths can be selected based on machine learning and/or big data accessible to the control circuit via, e.g., a cloud or surgical hub.

Figure 15:
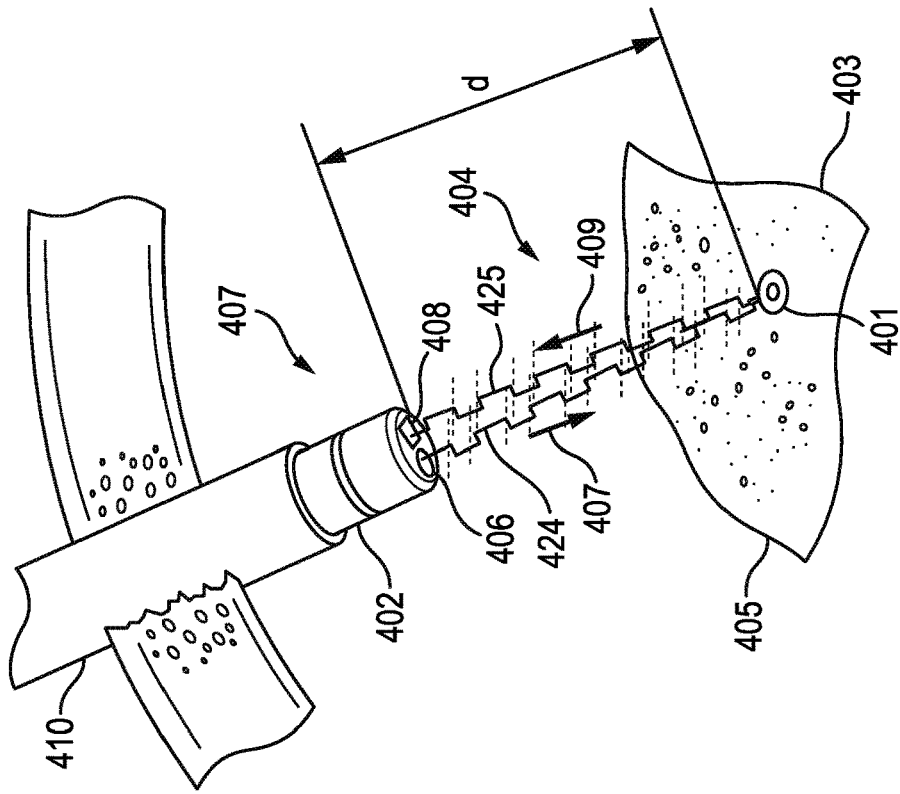
FIG. 15 is a schematic view of one embodiment of a near infrared (NIR) time-of-flight measurement system being utilized intraoperatively.

FIG. 15 illustrates one embodiment of spectral imaging to tissue being utilized intraoperatively to measure a distance between a waveform emitter and a critical structure that is obscured by tissue. FIG. 15 shows an embodiment of a time-of-flight sensor system 404 utilizing waveforms 424, 425. The time-of-flight sensor system 404 can be incorporated into a surgical visualization system, e.g., as the sensor system 104 of the surgical visualization system 100 of FIG. 1. The time-of-flight sensor system 404 includes a waveform emitter 406 and a waveform receiver 408 on the same surgical device 402 (e.g., the emitter 106 and the receiver 108 on the same surgical device 102 of FIG. 1). The emitted wave 400 extends to a critical structure 401 (e.g., the critical structure 101 of FIG. 1) from the emitter 406, and the received wave 425 is reflected back to by the receiver 408 from the critical structure 401. The surgical device 402 in this illustrated embodiment is positioned through a trocar 410 that extends into a cavity 407 in a patient. Although the trocar 410 is used in this in this illustrated embodiment, other trocars or other access devices can be used, or no access device may be used.

Figure 16:
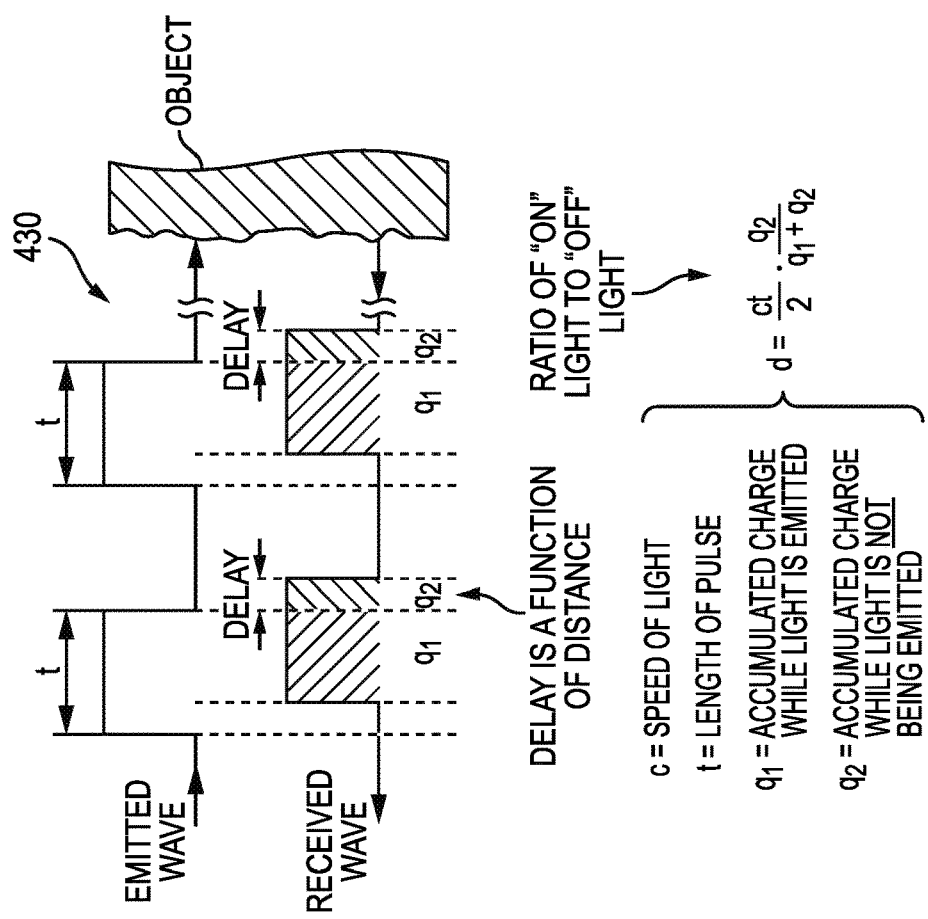
FIG. 16 shows a time-of-flight timing diagram for the system of FIG. 15.

The waveforms 424, 425 are configured to penetrate obscuring tissue 403, such as by having wavelengths in the NIR or SWIR spectrum of wavelengths. A spectral signal (e.g., hyperspectral, multispectral, or selective spectral) or a photoacoustic signal is emitted from the emitter 406, as shown by a first arrow 407 pointing distally, and can penetrate the tissue 403 in which the critical structure 401 is concealed. The emitted waveform 424 is reflected by the critical structure 401, as shown by a second arrow 409 pointing proximally. The received waveform 425 can be delayed due to a distance d between a distal end of the surgical device 402 and the critical structure 401. The waveforms 424, 425 can be selected to target the critical structure 401 within the tissue 403 based on the spectral signature of the critical structure 401, as described herein. The emitter 406 is configured to provide a binary signal on and off, as shown in FIG. 16, for example, which can be measured by the receiver 408.

Based on the delay between the emitted wave 424 and the received wave 425, the time-of-flight sensor system 404 is configured to determine the distance d. A time-of-flight timing diagram 430 for the emitter 406 and the receiver 408 of FIG. 15 is shown in FIG. 16. The delay is a function of the distance d and the distance d is given by:

$$d = \frac{ct}{2} \cdot \frac{q_2}{q_1 + q_2}$$

where c=the speed of light; t=length of pulse; q1=accumulated charge while light is emitted; and q2=accumulated charge while light is not being emitted.

The time-of-flight of the waveforms 424, 425 corresponds to the distance d in FIG. 15. In various instances, additional emitters/receivers and/or pulsing signals from the emitter 406 can be configured to emit a non-penetrating signal. The non-penetrating signal can be configured to determine the distance from the emitter 406 to the surface 405 of the obscuring tissue 403. In various instances, a depth of the critical structure 401 can be determined by:

$$d_A = d_w - d_t$$

where $d_A$=the depth of the critical structure 401; $d_w$=the distance from the emitter 406 to the critical structure 401 (d in FIG. 15); and $d_t$=the distance from the emitter 406 (on the distal end of the surgical device 402) to the surface 405 of the obscuring tissue 403.

FIG. 17 illustrates another embodiment of a time-of-flight sensor system 504 utilizing waves 524a, 524b, 524c, 525a, 525b, 525c is shown. The time-of-flight sensor system 504 can be incorporated into a surgical visualization system, e.g., as the sensor system 104 of the surgical visualization system 100 of FIG. 1. The time-of-flight sensor system 504 includes a waveform emitter 506 and a waveform receiver 508 (e.g., the emitter 106 and the receiver 108 of FIG. 1). The waveform emitter 506 is positioned on a first surgical device 502a (e.g., the surgical device 102 of FIG. 1), and the waveform receiver 508 is positioned on a second surgical device 502b. The surgical devices 502a, 502b are positioned through first and second trocars 510a, 510b, respectively, which extend into a cavity 507 in a patient. Although the trocars 510a, 510b are used in this in this illustrated embodiment, other trocars or other access devices can be used, or no access device may be used. The emitted waves 524a, 524b, 524c extend toward a surgical site from the emitter 506, and the received waves 525a, 525b, 525c are reflected back to the receiver 508 from various structures and/or surfaces at the surgical site.

The different emitted waves 524a, 524b, 524c are configured to target different types of material at the surgical site. For example, the wave 524a targets obscuring tissue 503, the wave 524b targets a first critical structure 501a (e.g., the critical structure 101 of FIG. 1), which is a vessel in this illustrated embodiment, and the wave 524c targets a second critical structure 501b (e.g., the critical structure 101 of FIG. 1), which is a cancerous tumor in this illustrated embodiment. The wavelengths of the waves 524a, 524b, 524c can be in the visible light, NIR, or SWIR spectrum of wavelengths. For example, visible light can be reflected off a surface 505 of the tissue 503, and NIR and/or SWIR waveforms can penetrate the surface 505 of the tissue 503. In various aspects, as described herein, a spectral signal (e.g., hyperspectral, multispectral, or selective spectral) or a photoacoustic signal can be emitted from the emitter 506. The waves 524b, 524c can be selected to target the critical structures 501a, 501b within the tissue 503 based on the spectral signature of the critical structure 501a, 501b, as described herein. Photoacoustic imaging is further described in various U.S. patent applications, which are incorporated by reference herein in the present disclosure.

The emitted waves 524a, 524b, 524c are reflected off the targeted material, namely the surface 505, the first critical structure 501a, and the second structure 501b, respectively. The received waveforms 525a, 525b, 525c can be delayed due to distances $d_{1a}$, $d_{2a}$, $d_{3a}$, $d_{1b}$, $d_{2b}$, $d_{2c}$.

In the time-of-flight sensor system 504, in which the emitter 506 and the receiver 508 are independently positionable (e.g., on separate surgical devices 502a, 502b and/or controlled by separate robotic arms), the various distances $d_{1a}$, $d_{2a}$, $d_{3a}$, $d_{1b}$, $d_{2b}$, $d_{2c}$ can be calculated from the known position of the emitter 506 and the receiver 508. For example, the positions can be known when the surgical devices 502a, 502b are robotically-controlled. Knowledge of the positions of the emitter 506 and the receiver 508, as well as the time of the photon stream to target a certain tissue and the information received by the receiver 508 of that particular response can allow a determination of the distances $d_{1a}$, $d_{2a}$, $d_{3a}$, $d_{1b}$, $d_{2b}$, $d_{2c}$. In one aspect, the distance to the obscured critical structures 501a, 501b can be triangulated using penetrating wavelengths. Because the speed of light is constant for any wavelength of visible or invisible light, the time-of-flight sensor system 504 can determine the various distances.

In a view provided to the medical practitioner, such as on a display, the receiver 508 can be rotated such that a center of mass of the target structure in the resulting images remains constant, e.g., in a plane perpendicular to an axis of a select target structure 503, 501a, or 501b. Such an orientation can quickly communicate one or more relevant distances and/or perspectives with respect to the target structure. For example, as shown in FIG. 17, the surgical site is displayed from a viewpoint in which the critical structure 501a is perpendicular to the viewing plane (e.g., the vessel is oriented in/out of the page). Such an orientation can be default setting; however, the view can be rotated or otherwise adjusted by a medical practitioner. In certain instances, the medical practitioner can toggle between different surfaces and/or target structures that define the viewpoint of the surgical site provided by the imaging system.

As in this illustrated embodiment, the receiver 508 can be mounted on the trocar 510b (or other access device) through which the surgical device 502b is positioned. In other embodiments, the receiver 508 can be mounted on a separate robotic arm for which the three-dimensional position is known. In various instances, the receiver 508 can be mounted on a movable arm that is separate from a robotic surgical system that controls the surgical device 502a or can be mounted to an operating room (OR) table or fixture that is intraoperatively registerable to the robot coordinate plane. In such instances, the position of the emitter 506 and the receiver 508 can be registerable to the same coordinate plane such that the distances can be triangulated from outputs from the time-of-flight sensor system 504.

Combining time-of-flight sensor systems and near-infrared spectroscopy (NIRS), termed TOF-NIRS, which is capable of measuring the time-resolved profiles of NIR light with nanosecond resolution can be found in "Time-Of-Flight Near-Infrared Spectroscopy For Nondestructive Measurement Of Internal Quality In Grapefruit," Journal of the American Society for Horticultural Science, May 2013 vol. 138 no. 3 225-228, which is hereby incorporated by reference in its entirety.

Embodiments of visualization systems and aspects and uses thereof are described further in U.S. Pat. Pub. No. 2020/0015923 entitled "Surgical Visualization Platform" filed Sep. 11, 2018, U.S. Pat. Pub. No. 2020/0015900 entitled "Controlling An Emitter Assembly Pulse Sequence" filed Sep. 11, 2018, U.S. Pat. Pub. No. 2020/0015668 entitled "Singular EMR Source Emitter Assembly" filed Sep. 11, 2018, U.S. Pat. Pub. No. 2020/0015925 entitled "Combination Emitter And Camera Assembly" filed Sep. 11, 2018, U.S. Pat. Pub. No. 2020/00015899 entitled "Surgical Visualization With Proximity Tracking Features" filed Sep. 11, 2018, U.S. Pat. Pub. No. 2020/00015903 entitled "Surgical Visualization Of Multiple Targets" filed Sep. 11, 2018, U.S. Pat. No. 10,792,034 entitled "Visualization Of Surgical Devices" filed Sep. 11, 2018, U.S. Pat. Pub. No. 2020/0015897 entitled "Operative Communication Of Light" filed Sep. 11, 2018, U.S. Pat. Pub. No. 2020/0015924 entitled "Robotic Light Projection Tools" filed Sep. 11, 2018, U.S. Pat. Pub. No. 2020/0015898 entitled "Surgical Visualization Feedback System" filed Sep. 11, 2018, U.S. Pat. Pub. No. 2020/0015906 entitled "Surgical Visualization And Monitoring" filed Sep. 11, 2018, U.S. Pat. Pub. No. 2020/0015907 entitled "Integration Of Imaging Data" filed Sep. 11, 2018, U.S. Pat. No. 10,925,598 entitled "Robotically-Assisted Surgical Suturing Systems" filed Sep. 11, 2018, U.S. Pat. Pub. No. 2020/0015901 entitled "Safety Logic For Surgical Suturing Systems" filed Sep. 11, 2018, U.S. Pat. Pub. No. 2020/0015914 entitled "Robotic Systems With Separate Photoacoustic Receivers" filed Sep. 11, 2018, U.S. Pat. Pub. No. 2020/0015902 entitled "Force Sensor Through Structured Light Deflection" filed Sep. 11, 2018, U.S. Pat. Pub. No. 2019/0201136 entitled "Method Of Hub Communication" filed Dec. 4, 2018, U.S. patent application Ser. No. 16/729,772 entitled "Analyzing Surgical Trends By A Surgical System" filed Dec. 30, 2019, U.S. patent application Ser. No. 16/729,747 entitled "Dynamic Surgical Visualization Systems" filed Dec. 30, 2019, U.S. patent application Ser. No. 16/729,744 entitled "Visualization Systems Using Structured Light" filed Dec. 30, 2019, U.S. patent application Ser. No. 16/729,778 entitled "System And Method For Determining, Adjusting, And Managing Resection Margin About A Subject Tissue" filed Dec. 30, 2019, U.S. patent application Ser. No. 16/729,729 entitled "Surgical Systems For Proposing And Corroborating Organ Portion Removals" filed Dec. 30, 2019, U.S. patent application Ser. No. 16/729,778 entitled "Surgical System For Overlaying Surgical Instrument Data Onto A Virtual Three Dimensional Construct Of An Organ" filed Dec. 30, 2019, U.S. patent application Ser. No. 16/729,751 entitled "Surgical Systems For Generating Three Dimensional Constructs Of Anatomical Organs And Coupling Identified Anatomical Structures Thereto" filed Dec. 30, 2019, U.S. patent application Ser. No. 16/729,740 entitled "Surgical Systems Correlating Visualization Data And Powered Surgical Instrument Data" filed Dec. 30, 2019, U.S. patent application Ser. No. 16/729,737 entitled "Adaptive Surgical System Control According To Surgical Smoke Cloud Characteristics" filed Dec. 30, 2019, U.S. patent application Ser. No. 16/729,796 entitled "Adaptive Surgical System Control According To Surgical Smoke Particulate Characteristics" filed Dec. 30, 2019, U.S. patent application Ser. No. 16/729,803 entitled "Adaptive Visualization By A Surgical System" filed Dec. 30, 2019, U.S. patent application Ser. No. 16/729,807 entitled "Method Of Using Imaging Devices In Surgery" filed Dec. 30, 2019, U.S. Pat. App No. 63/249,644 entitled "Surgical Devices, Systems, And Methods Using Multi-Source Imaging" filed on Sep. 29, 2021, U.S. Pat. App No. 63/249,652 entitled "Surgical Devices, Systems, Methods Using Fiducial Identification And Tracking" filed on Sep. 29, 2021, U.S. Pat. App No. 63/249,658 entitled "Surgical Devices, Systems, And Methods For Control Of One Visualization With Another" filed on Sep. 29, 2021, U.S. Pat. App No. 63/249,870 entitled "Methods And Systems For Controlling Cooperative Surgical Instruments" filed on Sep. 29, 2021, U.S. Pat. App No. 63/249,877 entitled "Methods And Systems For Controlling Cooperative Surgical Instruments" filed on Sep. 29, 2021, and U.S. Pat. App No. 63/249,980 entitled "Cooperative Access" filed on Sep. 29, 2021, which are hereby incorporated by reference in their entireties.

Surgical Hubs

The various visualization or imaging systems described herein can be incorporated into a system that includes a surgical hub. In general, a surgical hub can be a component of a comprehensive digital medical system capable of spanning multiple medical facilities and configured to provide integrated and comprehensive improved medical care to a vast number of patients. The comprehensive digital medical system includes a cloud-based medical analytics system that is configured to interconnect to multiple surgical hubs located across many different medical facilities. The surgical hubs are configured to interconnect with one or more elements, such as one or more surgical instruments that are used to conduct medical procedures on patients and/or one or more visualization systems that are used during performance of medical procedures. The surgical hubs provide a wide array of functionality to improve the outcomes of medical procedures. The data generated by the various surgical devices, visualization systems, and surgical hubs about the patient and the medical procedure may be transmitted to the cloud-based medical analytics system. This data may then be aggregated with similar data gathered from many other surgical hubs, visualization systems, and surgical instruments located at other medical facilities. Various patterns and correlations may be found through the cloud-based analytics system analyzing the collected data. Improvements in the techniques used to generate the data may be generated as a result, and these improvements may then be disseminated to the various surgical hubs, visualization systems, and surgical instruments. Due to the interconnectedness of all of the aforementioned components, improvements in medical procedures and practices may be found that otherwise may not be found if the many components were not so interconnected.

Examples of surgical hubs configured to receive, analyze, and output data, and methods of using such surgical hubs, are further described in U.S. Pat. Pub. No. 2019/0200844 entitled "Method Of Hub Communication, Processing, Storage And Display" filed Dec. 4, 2018, U.S. Pat. Pub. No. 2019/0200981 entitled "Method Of Compressing Tissue Within A Stapling Device And Simultaneously Displaying The Location Of The Tissue Within The Jaws" filed Dec. 4, 2018, U.S. Pat. Pub. No. 2019/0201046 entitled "Method For Controlling Smart Energy Devices" filed Dec. 4, 2018, U.S. Pat. Pub. No. 2019/0201114 entitled "Adaptive Control Program Updates For Surgical Hubs" filed Mar. 29, 2018, U.S. Pat. Pub. No. 2019/0201140 entitled "Surgical Hub Situational Awareness" filed Mar. 29, 2018, U.S. Pat. Pub. No. 2019/0206004 entitled "Interactive Surgical Systems With Condition Handling Of Devices And Data Capabilities" filed Mar. 29, 2018, U.S. Pat. Pub. No. 2019/0206555 entitled "Cloud-based Medical Analytics For Customization And Recommendations To A User" filed Mar. 29, 2018, and U.S. Pat. Pub. No. 2019/0207857 entitled "Surgical Network Determination Of Prioritization Of Communication, Interaction, Or Processing Based On System Or Device Needs" filed Nov. 6, 2018, which are hereby incorporated by reference in their entireties.

Figure 18:
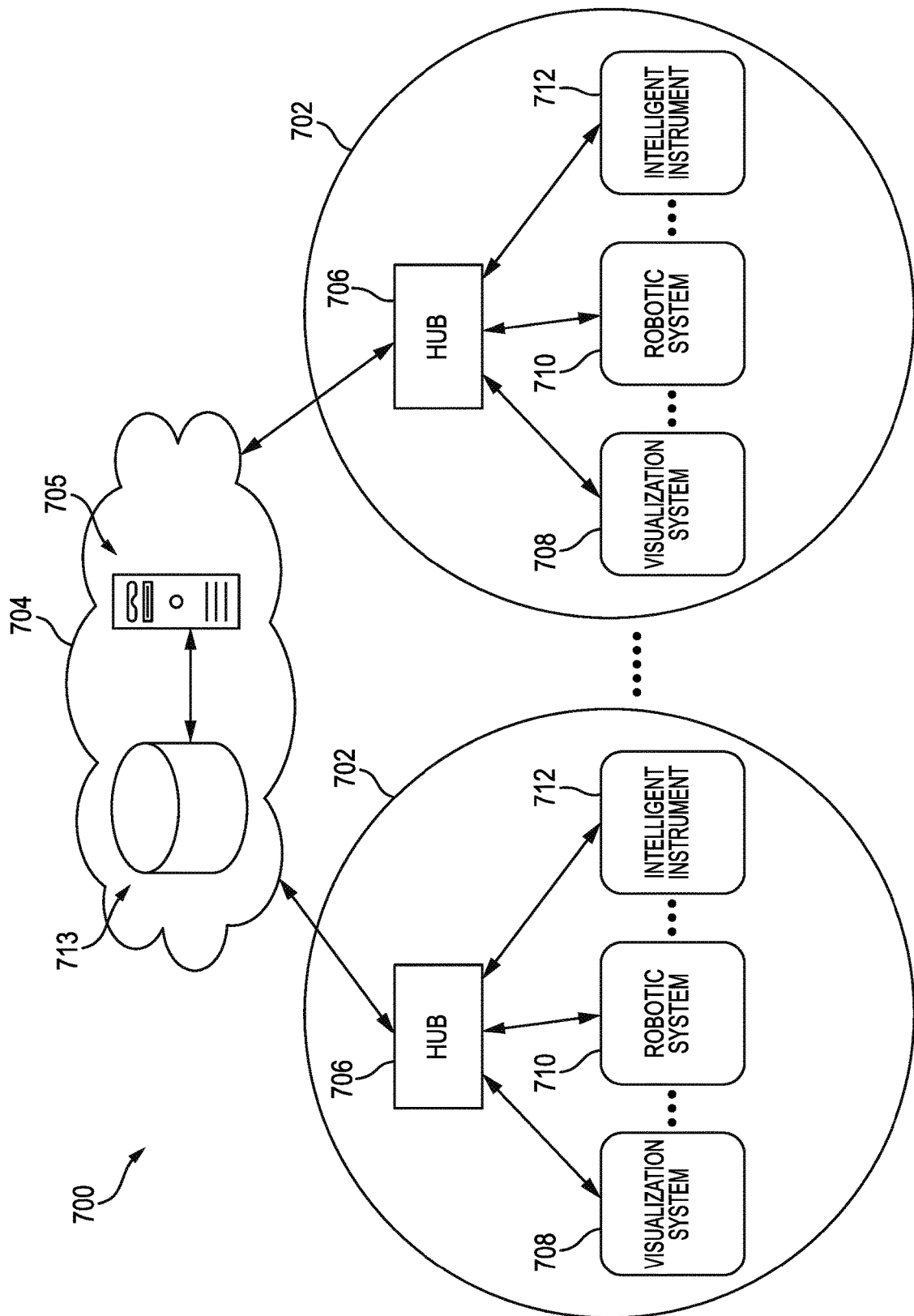
FIG. 18 is a schematic view of one embodiment of a computer-implemented interactive surgical system.

FIG. 18 illustrates one embodiment of a computer-implemented interactive surgical system 700 that includes one or more surgical systems 702 and a cloud-based system (e.g., a cloud 704 that can include a remote server 713 coupled to a storage device 705). Each surgical system 702 includes at least one surgical hub 706 in communication with the cloud 704. In one example, as illustrated in FIG. 18, the surgical system 702 includes a visualization system 708, a robotic system 710, and an intelligent (or "smart") surgical instrument 712, which are configured to communicate with one another and/or the hub 706. The intelligent surgical instrument 712 can include imaging device(s). The surgical system 702 can include an M number of hubs 706, an N number of visualization systems 708, an O number of robotic systems 710, and a P number of intelligent surgical instruments 712, where M, N, O, and P are integers greater than or equal to one that may or may not be equal to any one or more of each other. Various exemplary intelligent surgical instruments and robotic systems are described herein.

Data received by a surgical hub from a surgical visualization system can be used in any of a variety of ways. In an exemplary embodiment, the surgical hub can receive data from a surgical visualization system in use with a patient in a surgical setting, e.g., in use in an operating room during performance of a surgical procedure. The surgical hub can use the received data in any of one or more ways, as discussed herein.

The surgical hub can be configured to analyze received data in real time with use of the surgical visualization system and adjust control one or more of the surgical visualization system and/or one or more intelligent surgical instruments in use with the patient based on the analysis of the received data. Such adjustment can include, for example, adjusting one or operational control parameters of intelligent surgical instrument(s), causing one or more sensors of one or more intelligent surgical instruments to take a measurement to help gain an understanding of the patient's current physiological condition, and/or current operational status of an intelligent surgical instrument, and other adjustments. Controlling and adjusting operation of intelligent surgical instruments is discussed further below. Examples of operational control parameters of an intelligent surgical instrument include motor speed, cutting element speed, time, duration, level of energy application, and light emission. Examples of surgical hubs and of controlling and adjusting intelligent surgical instrument operation are described further in previously mentioned U.S. patent application Ser. No. 16/729,772 entitled "Analyzing Surgical Trends By A Surgical System" filed Dec. 30, 2019, U.S. patent application Ser. No. 16/729,747 entitled "Dynamic Surgical Visualization Systems" filed Dec. 30, 2019, U.S. patent application Ser. No. 16/729,744 entitled "Visualization Systems Using Structured Light" filed Dec. 30, 2019, U.S. patent application Ser. No. 16/729,778 entitled "System And Method For Determining, Adjusting, And Managing Resection Margin About A Subject Tissue" filed Dec. 30, 2019, U.S. patent application Ser. No. 16/729,729 entitled "Surgical Systems For Proposing And Corroborating Organ Portion Removals" filed Dec. 30, 2019, U.S. patent application Ser. No. 16/729,778 entitled "Surgical System For Overlaying Surgical Instrument Data Onto A Virtual Three Dimensional Construct Of An Organ" filed Dec. 30, 2019, U.S. patent application Ser. No. 16/729,751 entitled "Surgical Systems For Generating Three Dimensional Constructs Of Anatomical Organs And Coupling Identified Anatomical Structures Thereto" filed Dec. 30, 2019, U.S. patent application Ser. No. 16/729,740 entitled "Surgical Systems Correlating Visualization Data And Powered Surgical Instrument Data" filed Dec. 30, 2019, U.S. patent application Ser. No. 16/729,737 entitled "Adaptive Surgical System Control According To Surgical Smoke Cloud Characteristics" filed Dec. 30, 2019, U.S. patent application Ser. No. 16/729,796 entitled "Adaptive Surgical System Control According To Surgical Smoke Particulate Characteristics" filed Dec. 30, 2019, U.S. patent application Ser. No. 16/729,803 entitled "Adaptive Visualization By A Surgical System" filed Dec. 30, 2019, and U.S. patent application Ser. No. 16/729,807 entitled "Method Of Using Imaging Devices In Surgery" filed Dec. 30, 2019, and in U.S. patent application Ser. No. 17/068,857 entitled "Adaptive Responses From Smart Packaging Of Drug Delivery Absorbable Adjuncts" filed Oct. 13, 2020, U.S. patent application Ser. No. 17/068,858 entitled "Drug Administration Devices That Communicate With Surgical Hubs" filed Oct. 13, 2020, U.S. patent application Ser. No. 17/068,859 entitled "Controlling Operation Of Drug Administration Devices Using Surgical Hubs" filed Oct. 13, 2020, U.S. patent application Ser. No. 17/068,863 entitled "Patient Monitoring Using Drug Administration Devices" filed Oct. 13, 2020, U.S. patent application Ser. No. 17/068,865 entitled "Monitoring And Communicating Information Using Drug Administration Devices" filed Oct. 13, 2020, and U.S. patent application Ser. No. 17/068,867 entitled "Aggregating And Analyzing Drug Administration Data" filed Oct. 13, 2020, which are hereby incorporated by reference in their entireties.

The surgical hub can be configured to cause visualization of the received data to be provided in the surgical setting on a display so that a medical practitioner in the surgical setting can view the data and thereby receive an understanding of the operation of the imaging device(s) in use in the surgical setting. Such information provided via visualization can include text and/or images.

Figure 19:
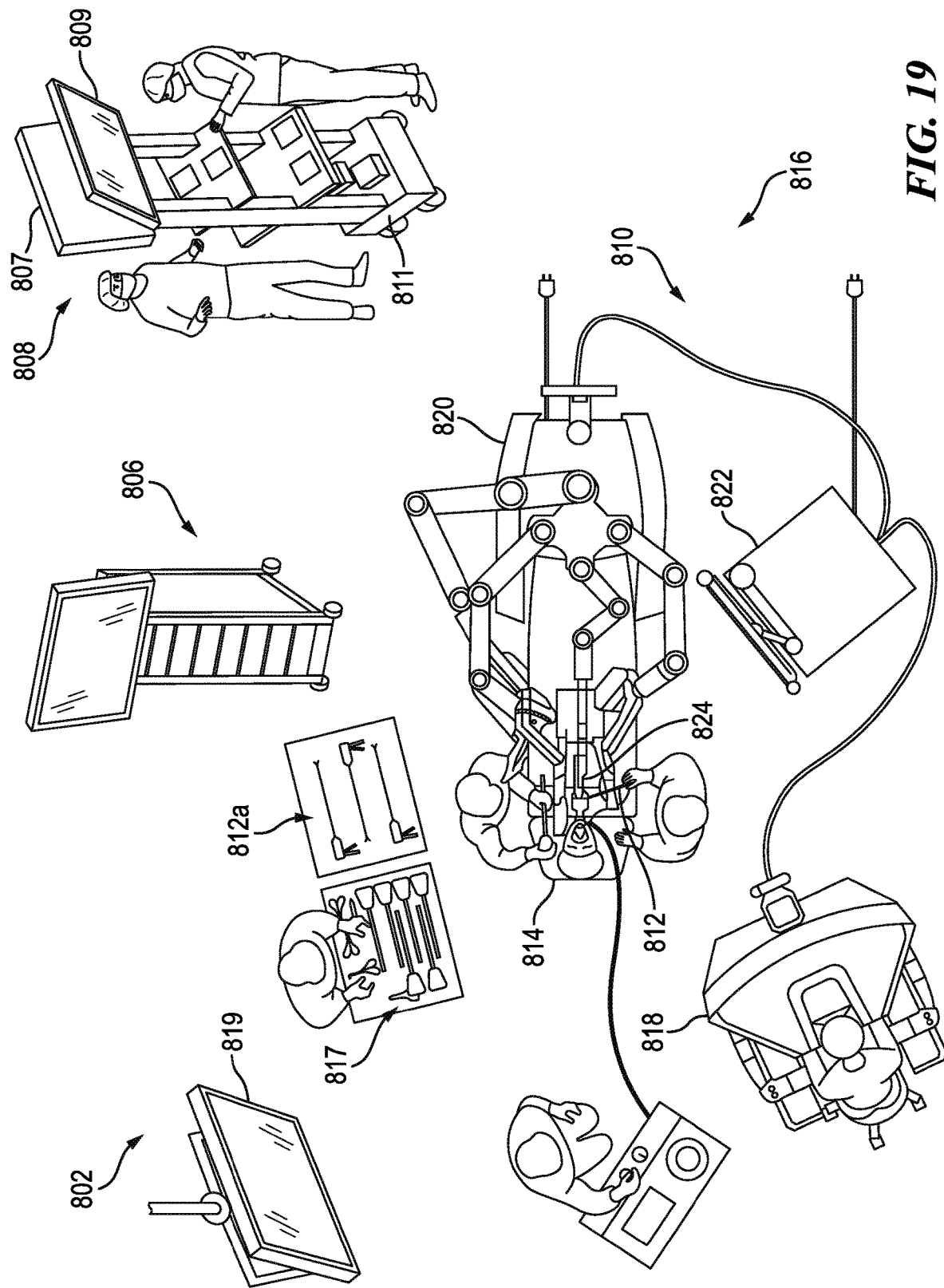
FIG. 19 is a schematic view of one embodiment a surgical system being used to perform a surgical procedure in an operating room.

FIG. 19 illustrates one embodiment of a surgical system 802 including a surgical hub 806 (e.g., the surgical hub 706 of FIG. 18 or other surgical hub described herein), a robotic surgical system 810 (e.g., the robotic surgical system 110 of FIG. 1 or other robotic surgical system herein), and a visualization system 808 (e.g., the visualization system 100 of FIG. 1 or other visualization system described herein). The surgical hub 806 can be in communication with a cloud, as discussed herein. FIG. 19 shows the surgical system 802 being used to perform a surgical procedure on a patient who is lying down on an operating table 814 in a surgical operating room 816. The robotic system 810 includes a surgeon's console 818, a patient side cart 820 (surgical robot), and a robotic system surgical hub 822. The robotic system surgical hub 822 is generally configured similar to the surgical hub 822 and can be in communication with a cloud. In some embodiments, the robotic system surgical hub 822 and the surgical hub 806 can be combined. The patient side cart 820 can manipulate an intelligent surgical tool 812 through a minimally invasive incision in the body of the patient while a medical practitioner, e.g., a surgeon, nurse, and/or other medical practitioner, views the surgical site through the surgeon's console 818. An image of the surgical site can be obtained by an imaging device 824 (e.g., the imaging device 120 of FIG. 1 or other imaging device described herein), which can be manipulated by the patient side cart 820 to orient the imaging device 824. The robotic system surgical hub 822 can be used to process the images of the surgical site for subsequent display to the surgeon through the surgeon's console 818.

A primary display 819 is positioned in the sterile field of the operating room 816 and is configured to be visible to an operator at the operating table 814. In addition, as in this illustrated embodiment, a visualization tower 818 can positioned outside the sterile field. The visualization tower 818 includes a first non-sterile display 807 and a second non-sterile display 809, which face away from each other. The visualization system 808, guided by the surgical hub 806, is configured to utilize the displays 807, 809, 819 to coordinate information flow to medical practitioners inside and outside the sterile field. For example, the surgical hub 806 can cause the visualization system 808 to display a snapshot and/or a video of a surgical site, as obtained by the imaging device 824, on one or both of the non-sterile displays 807, 809, while maintaining a live feed of the surgical site on the primary display 819. The snapshot and/or video on the non-sterile display 807 and/or 809 can permit a non-sterile medical practitioner to perform a diagnostic step relevant to the surgical procedure, for example.

The surgical hub 806 is configured to route a diagnostic input or feedback entered by a non-sterile medical practitioner at the visualization tower 818 to the primary display 819 within the sterile field, where it can be viewed by a sterile medical practitioner at the operating table 814. For example, the input can be in the form of a modification to the snapshot and/or video displayed on the non-sterile display 807 and/or 809, which can be routed to the primary display 819 by the surgical hub 806.

The surgical hub 806 is configured to coordinate information flow to a display of the intelligent surgical instrument 812, as is described in various U.S. Patent Applications that are incorporated by reference herein in the present disclosure. A diagnostic input or feedback entered by a non-sterile operator at the visualization tower 818 can be routed by the surgical hub 806 to the display 819 within the sterile field, where it can be viewed by the operator of the surgical instrument 812 and/or by other medical practitioner(s) in the sterile field.

The intelligent surgical instrument 812 and the imaging device 824, which is also an intelligent surgical tool, is being used with the patient in the surgical procedure as part of the surgical system 802. Other intelligent surgical instruments 812a that can be used in the surgical procedure, e.g., that can be removably coupled to the patient side cart 820 and be in communication with the robotic surgical system 810 and the surgical hub 806, are also shown in FIG. 19 as being available. Non-intelligent (or "dumb") surgical instruments 817, e.g., scissors, trocars, cannulas, scalpels, etc., that cannot be in communication with the robotic surgical system 810 and the surgical hub 806 are also shown in FIG. 19 as being available for use.

Operating Intelligent Surgical Instruments

An intelligent surgical device can have an algorithm stored thereon, e.g., in a memory thereof, configured to be executable on board the intelligent surgical device, e.g., by a processor thereof, to control operation of the intelligent surgical device. In some embodiments, instead of or in addition to being stored on the intelligent surgical device, the algorithm can be stored on a surgical hub, e.g., in a memory thereof, that is configured to communicate with the intelligent surgical device.

The algorithm is stored in the form of one or more sets of pluralities of data points defining and/or representing instructions, notifications, signals, etc. to control functions of the intelligent surgical device. In some embodiments, data gathered by the intelligent surgical device can be used by the intelligent surgical device, e.g., by a processor of the intelligent surgical device, to change at least one variable parameter of the algorithm. As discussed above, a surgical hub can be in communication with an intelligent surgical device, so data gathered by the intelligent surgical device can be communicated to the surgical hub and/or data gathered by another device in communication with the surgical hub can be communicated to the surgical hub, and data can be communicated from the surgical hub to the intelligent surgical device. Thus, instead of or in addition to the intelligent surgical device being configured to change a stored variable parameter, the surgical hub can be configured to communicate the changed at least one variable, alone or as part of the algorithm, to the intelligent surgical device and/or the surgical hub can communicate an instruction to the intelligent surgical device to change the at least one variable as determined by the surgical hub.

The at least one variable parameter is among the algorithm's data points, e.g., are included in instructions for operating the intelligent surgical device, and are thus each able to be changed by changing one or more of the stored pluralities of data points of the algorithm. After the at least one variable parameter has been changed, subsequent execution of the algorithm is according to the changed algorithm. As such, operation of the intelligent surgical device over time can be managed for a patient to increase the beneficial results use of the intelligent surgical device by taking into consideration actual situations of the patient and actual conditions and/or results of the surgical procedure in which the intelligent surgical device is being used. Changing the at least one variable parameter is automated to improve patient outcomes. Thus, the intelligent surgical device can be configured to provide personalized medicine based on the patient and the patient's surrounding conditions to provide a smart system. In a surgical setting in which the intelligent surgical device is being used during performance of a surgical procedure, automated changing of the at least one variable parameter may allow for the intelligent surgical device to be controlled based on data gathered during the performance of the surgical procedure, which may help ensure that the intelligent surgical device is used efficiently and correctly and/or may help reduce chances of patient harm by harming a critical anatomical structure.

The at least one variable parameter can be any of a variety of different operational parameters. Examples of variable parameters include motor speed, motor torque, energy level, energy application duration, tissue compression rate, jaw closure rate, cutting element speed, load threshold, etc.

Figure 20:
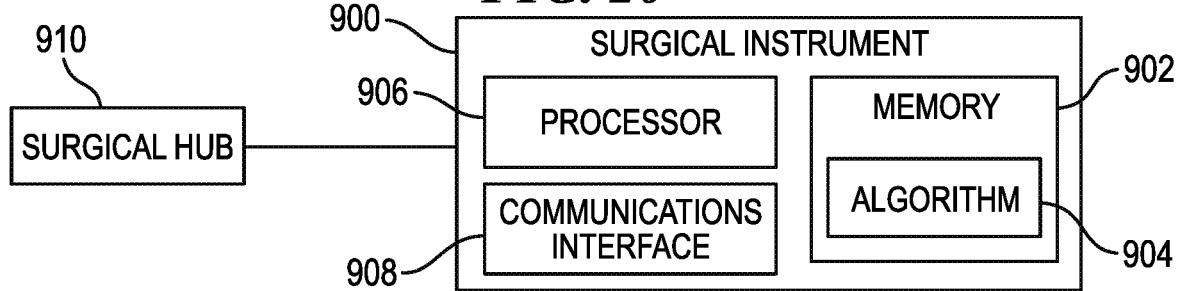
FIG. 20 is a schematic view of one embodiment of a surgical system including a smart surgical instrument and a surgical hub.

FIG. 20 illustrates one embodiment of an intelligent surgical instrument 900 including a memory 902 having an algorithm 904 stored therein that includes at least one variable parameter. The algorithm 904 can be a single algorithm or can include a plurality of algorithms, e.g., separate algorithms for different aspects of the surgical instrument's operation, where each algorithm includes at least one variable parameter. The intelligent surgical instrument 900 can be the surgical device 102 of FIG. 1, the imaging device 120 of FIG. 1, the surgical device 202 of FIG. 8, the imaging device 220 of FIG. 8, the surgical device 402 of FIG. 15, the surgical device 502a of FIG. 17, the surgical device 502b of FIG. 17, the surgical device 712 of FIG. 18, the surgical device 812 of FIG. 19, the imaging device 824 of FIG. 19, or other intelligent surgical instrument. The surgical instrument 900 also includes a processor 906 configured to execute the algorithm 904 to control operation of at least one aspect of the surgical instrument 900. To execute the algorithm 904, the processor 906 is configured to run a program stored in the memory 902 to access a plurality of data points of the algorithm 904 in the memory 902.

The surgical instrument 900 also includes a communications interface 908, e.g., a wireless transceiver or other wired or wireless communications interface, configured to communicate with another device, such as a surgical hub 910. The communications interface 908 can be configured to allow one-way communication, such as providing data to a remote server (e.g., a cloud server or other server) and/or to a local, surgical hub server, and/or receiving instructions or commands from a remote server and/or a local, surgical hub server, or two-way communication, such as providing information, messages, data, etc. regarding the surgical instrument 900 and/or data stored thereon and receiving instructions, such as from a doctor; a remote server regarding updates to software; a local, surgical hub server regarding updates to software; etc.

The surgical instrument 900 is simplified in FIG. 20 and can include additional components, e.g., a bus system, a handle, a elongate shaft having an end effector at a distal end thereof, a power source, etc. The processor 906 can also be configured to execute instructions stored in the memory 902 to control the device 900 generally, including other electrical components thereof such as the communications interface 908, an audio speaker, a user interface, etc.

The processor 906 is configured to change at least one variable parameter of the algorithm 904 such that a subsequent execution of the algorithm 904 will be in accordance with the changed at least one variable parameter. To change the at least one variable parameter of the algorithm 904, the processor 906 is configured to modify or update the data point(s) of the at least one variable parameter in the memory 902. The processor 906 can be configured to change the at least one variable parameter of the algorithm 904 in real time with use of the surgical device 900 during performance of a surgical procedure, which may accommodate real time conditions.

Additionally or alternatively to the processor 906 changing the at least one variable parameter, the processor 906 can be configured to change the algorithm 904 and/or at least one variable parameter of the algorithm 904 in response to an instruction received from the surgical hub 910. In some embodiments, the processor 906 is configured to change the at least one variable parameter only after communicating with the surgical hub 910 and receiving an instruction therefrom, which may help ensure coordinated action of the surgical instrument 900 with other aspects of the surgical procedure in which the surgical instrument 900 is being used.

In an exemplary embodiment, the processor 906 executes the algorithm 904 to control operation of the surgical instrument 900, changes the at least one variable parameter of the algorithm 904 based on real time data, and executes the algorithm 904 after changing the at least one variable parameter to control operation of the surgical instrument 900.

Figure 21:
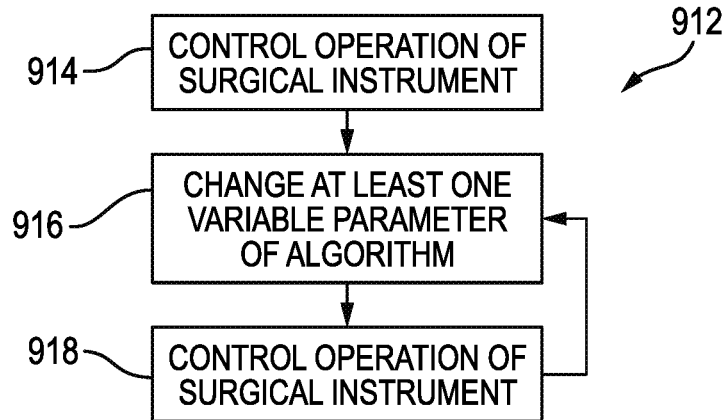
FIG. 21 is a flowchart showing a method of controlling the smart surgical instrument of FIG. 20.

FIG. 21 illustrates one embodiment of a method 912 of using of the surgical instrument 900 including a change of at least one variable parameter of the algorithm 904. The processor 906 controls 914 operation of the surgical instrument 900 by executing the algorithm 904 stored in the memory 902. Based on any of this subsequently known data and/or subsequently gathered data, the processor 904 changes 916 the at least one variable parameter of the algorithm 904 as discussed above. After changing the at least one variable parameter, the processor 906 controls 918 operation of the surgical instrument 900 by executing the algorithm 904, now with the changed at least one variable parameter. The processor 904 can change 916 the at least one variable parameter any number of times during performance of a surgical procedure, e.g., zero, one, two, three, etc. During any part of the method 912, the surgical instrument 900 can communicate with one or more computer systems, e.g., the surgical hub 910, a remote server such as a cloud server, etc., using the communications interface 908 to provide data thereto and/or receive instructions therefrom.

Situational Awareness

Operation of an intelligent surgical instrument can be altered based on situational awareness of the patient. The operation of the intelligent surgical instrument can be altered manually, such as by a user of the intelligent surgical instrument handling the instrument differently, providing a different input to the instrument, ceasing use of the instrument, etc. Additionally or alternatively, the operation of an intelligent surgical instrument can be changed automatically by an algorithm of the instrument being changed, e.g., by changing at least one variable parameter of the algorithm. As mentioned above, the algorithm can be adjusted automatically without user input requesting the change. Automating the adjustment during performance of a surgical procedure may help save time, may allow medical practitioners to focus on other aspects of the surgical procedure, and/or may ease the process of using the surgical instrument for a medical practitioner, which each may improve patient outcomes, such as by avoiding a critical structure, controlling the surgical instrument with consideration of a tissue type the instrument is being used on and/or near, etc.

The visualization systems described herein can be utilized as part of a situational awareness system that can be embodied or executed by a surgical hub, e.g., the surgical hub 706, the surgical hub 806, or other surgical hub described herein. In particular, characterizing, identifying, and/or visualizing surgical instruments (including their positions, orientations, and actions), tissues, structures, users, and/or other things located within the surgical field or the operating theater can provide contextual data that can be utilized by a situational awareness system to infer various information, such as a type of surgical procedure or a step thereof being performed, a type of tissue(s) and/or structure(s) being manipulated by a surgeon or other medical practitioner, and other information. The contextual data can then be utilized by the situational awareness system to provide alerts to a user, suggest subsequent steps or actions for the user to undertake, prepare surgical devices in anticipation for their use (e.g., activate an electrosurgical generator in anticipation of an electrosurgical instrument being utilized in a subsequent step of the surgical procedure, etc.), control operation of intelligent surgical instruments (e.g., customize surgical instrument operational parameters of an algorithm as discussed further below), and so on.

Although an intelligent surgical device including an algorithm that responds to sensed data, e.g., by having at least one variable parameter of the algorithm changed, can be an improvement over a "dumb" device that operates without accounting for sensed data, some sensed data can be incomplete or inconclusive when considered in isolation, e.g., without the context of the type of surgical procedure being performed or the type of tissue that is being operated on. Without knowing the procedural context (e.g., knowing the type of tissue being operated on or the type of procedure being performed), the algorithm may control the surgical device incorrectly or sub-optimally given the particular context-free sensed data. For example, the optimal manner for an algorithm to control a surgical instrument in response to a particular sensed parameter can vary according to the particular tissue type being operated on. This is due to the fact that different tissue types have different properties (e.g., resistance to tearing, ease of being cut, etc.) and thus respond differently to actions taken by surgical instruments. Therefore, it may be desirable for a surgical instrument to take different actions even when the same measurement for a particular parameter is sensed. As one example, the optimal manner in which to control a surgical stapler in response to the surgical stapler sensing an unexpectedly high force to close its end effector will vary depending upon whether the tissue type is susceptible or resistant to tearing. For tissues that are susceptible to tearing, such as lung tissue, the surgical instrument's control algorithm would optimally ramp down the motor in response to an unexpectedly high force to close to avoid tearing the tissue, e.g., change a variable parameter controlling motor speed or torque so the motor is slower. For tissues that are resistant to tearing, such as stomach tissue, the instrument's algorithm would optimally ramp up the motor in response to an unexpectedly high force to close to ensure that the end effector is clamped properly on the tissue, e.g., change a variable parameter controlling motor speed or torque so the motor is faster. Without knowing whether lung or stomach tissue has been clamped, the algorithm may be sub-optimally changed or not changed at all.

A surgical hub can be configured to derive information about a surgical procedure being performed based on data received from various data sources and then control modular devices accordingly. In other words, the surgical hub can be configured to infer information about the surgical procedure from received data and then control the modular devices operably coupled to the surgical hub based upon the inferred context of the surgical procedure. Modular devices can include any surgical device that is controllable by a situational awareness system, such as visualization system devices (e.g., a camera, a display screen, etc.), smart surgical instruments (e.g., an ultrasonic surgical instrument, an electrosurgical instrument, a surgical stapler, smoke evacuators, scopes, etc.). A modular device can include sensor(s)s configured to detect parameters associated with a patient with which the device is being used and/or associated with the modular device itself.

The contextual information derived or inferred from the received data can include, for example, a type of surgical procedure being performed, a particular step of the surgical procedure that the surgeon (or other medical practitioner) is performing, a type of tissue being operated on, or a body cavity that is the subject of the surgical procedure. The situational awareness system of the surgical hub can be configured to derive the contextual information from the data received from the data sources in a variety of different ways. In an exemplary embodiment, the contextual information received by the situational awareness system of the surgical hub is associated with a particular control adjustment or set of control adjustments for one or more modular devices. The control adjustments each correspond to a variable parameter. In one example, the situational awareness system includes a pattern recognition system, or machine learning system (e.g., an artificial neural network), that has been trained on training data to correlate various inputs (e.g., data from databases, patient monitoring devices, and/or modular devices) to corresponding contextual information regarding a surgical procedure. In other words, a machine learning system can be trained to accurately derive contextual information regarding a surgical procedure from the provided inputs. In another example, the situational awareness system can include a lookup table storing pre-characterized contextual information regarding a surgical procedure in association with one or more inputs (or ranges of inputs) corresponding to the contextual information. In response to a query with one or more inputs, the lookup table can return the corresponding contextual information for the situational awareness system for controlling at least one modular device. In another example, the situational awareness system includes a further machine learning system, lookup table, or other such system, which generates or retrieves one or more control adjustments for one or more modular devices when provided the contextual information as input.

A surgical hub including a situational awareness system may provide any number of benefits for a surgical system. One benefit includes improving the interpretation of sensed and collected data, which would in turn improve the processing accuracy and/or the usage of the data during the course of a surgical procedure. Another benefit is that the situational awareness system for the surgical hub may improve surgical procedure outcomes by allowing for adjustment of surgical instruments (and other modular devices) for the particular context of each surgical procedure (such as adjusting to different tissue types) and validating actions during a surgical procedure. Yet another benefit is that the situational awareness system may improve surgeon's and/or other medical practitioners' efficiency in performing surgical procedures by automatically suggesting next steps, providing data, and adjusting displays and other modular devices in the surgical theater according to the specific context of the procedure. Another benefit includes proactively and automatically controlling modular devices according to the particular step of the surgical procedure that is being performed to reduce the number of times that medical practitioners are required to interact with or control the surgical system during the course of a surgical procedure, such as by a situationally aware surgical hub proactively activating a generator to which an RF electrosurgical instrument is connected if it determines that a subsequent step of the procedure requires the use of the instrument. Proactively activating the energy source allows the instrument to be ready for use a soon as the preceding step of the procedure is completed.

For example, a situationally aware surgical hub can be configured to determine what type of tissue is being operated on. Therefore, when an unexpectedly high force to close a surgical instrument's end effector is detected, the situationally aware surgical hub can be configured to correctly ramp up or ramp down a motor of the surgical instrument for the type of tissue, e.g., by changing or causing change of at least one variable parameter of an algorithm for the surgical instrument regarding motor speed or torque.

For another example, a type of tissue being operated can affect adjustments that are made to compression rate and load thresholds of a surgical stapler for a particular tissue gap measurement. A situationally aware surgical hub can be configured to infer whether a surgical procedure being performed is a thoracic or an abdominal procedure, allowing the surgical hub to determine whether the tissue clamped by an end effector of the surgical stapler is lung tissue (for a thoracic procedure) or stomach tissue (for an abdominal procedure). The surgical hub can then be configured to cause adjustment of the compression rate and load thresholds of the surgical stapler appropriately for the type of tissue, e.g., by changing or causing change of at least one variable parameter of an algorithm for the surgical stapler regarding compression rate and load threshold.

As yet another example, a type of body cavity being operated in during an insufflation procedure can affect the function of a smoke evacuator. A situationally aware surgical hub can be configured to determine whether the surgical site is under pressure (by determining that the surgical procedure is utilizing insufflation) and determine the procedure type. As a procedure type is generally performed in a specific body cavity, the surgical hub can be configured to control a motor rate of the smoke evacuator appropriately for the body cavity being operated in, e.g., by changing or causing change of at least one variable parameter of an algorithm for the smoke evacuator regarding motor rate. Thus, a situationally aware surgical hub may provide a consistent amount of smoke evacuation for both thoracic and abdominal procedures.

As yet another example, a type of procedure being performed can affect the optimal energy level for an ultrasonic surgical instrument or radio frequency (RF) electrosurgical instrument to operate at. Arthroscopic procedures, for example, require higher energy levels because an end effector of the ultrasonic surgical instrument or RF electrosurgical instrument is immersed in fluid. A situationally aware surgical hub can be configured to determine whether the surgical procedure is an arthroscopic procedure. The surgical hub can be configured to adjust an RF power level or an ultrasonic amplitude of the generator (e.g., adjust energy level) to compensate for the fluid filled environment, e.g., by changing or causing change of at least one variable parameter of an algorithm for the instrument and/or a generator regarding energy level. Relatedly, a type of tissue being operated on can affect the optimal energy level for an ultrasonic surgical instrument or RF electrosurgical instrument to operate at. A situationally aware surgical hub can be configured to determine what type of surgical procedure is being performed and then customize the energy level for the ultrasonic surgical instrument or RF electrosurgical instrument, respectively, according to the expected tissue profile for the surgical procedure, e.g., by changing or causing change of at least one variable parameter of an algorithm for the instrument and/or a generator regarding energy level. Furthermore, a situationally aware surgical hub can be configured to adjust the energy level for the ultrasonic surgical instrument or RF electrosurgical instrument throughout the course of a surgical procedure, rather than just on a procedure-by-procedure basis. A situationally aware surgical hub can be configured to determine what step of the surgical procedure is being performed or will subsequently be performed and then update the control algorithm(s) for the generator and/or ultrasonic surgical instrument or RF electrosurgical instrument to set the energy level at a value appropriate for the expected tissue type according to the surgical procedure step.

As another example, a situationally aware surgical hub can be configured to determine whether the current or subsequent step of a surgical procedure requires a different view or degree of magnification on a display according to feature(s) at the surgical site that the surgeon and/or other medical practitioner is expected to need to view. The surgical hub can be configured to proactively change the displayed view (supplied by, e.g., an imaging device for a visualization system) accordingly so that the display automatically adjusts throughout the surgical procedure.

As yet another example, a situationally aware surgical hub can be configured to determine which step of a surgical procedure is being performed or will subsequently be performed and whether particular data or comparisons between data will be required for that step of the surgical procedure. The surgical hub can be configured to automatically call up data screens based upon the step of the surgical procedure being performed, without waiting for the surgeon or other medical practitioner to ask for the particular information.

As another example, a situationally aware surgical hub can be configured to determine whether a surgeon and/or other medical practitioner is making an error or otherwise deviating from an expected course of action during the course of a surgical procedure, e.g., as provided in a pre-operative surgical plan. For example, the surgical hub can be configured to determine a type of surgical procedure being performed, retrieve a corresponding list of steps or order of equipment usage (e.g., from a memory), and then compare the steps being performed or the equipment being used during the course of the surgical procedure to the expected steps or equipment for the type of surgical procedure that the surgical hub determined is being performed. The surgical hub can be configured to provide an alert (visual, audible, and/or tactile) indicating that an unexpected action is being performed or an unexpected device is being utilized at the particular step in the surgical procedure.

In certain instances, operation of a robotic surgical system, such as any of the various robotic surgical systems described herein, can be controlled by the surgical hub based on its situational awareness and/or feedback from the components thereof and/or based on information from a cloud (e.g., the cloud 713 of FIG. 18).

Embodiments of situational awareness systems and using situational awareness systems during performance of a surgical procedure are described further in previously mentioned U.S. patent application Ser. No. 16/729,772 entitled "Analyzing Surgical Trends By A Surgical System" filed Dec. 30, 2019, U.S. patent application Ser. No. 16/729,747 entitled "Dynamic Surgical Visualization Systems" filed Dec. 30, 2019, U.S. patent application Ser. No. 16/729,744 entitled "Visualization Systems Using Structured Light" filed Dec. 30, 2019, U.S. patent application Ser. No. 16/729,778 entitled "System And Method For Determining, Adjusting, And Managing Resection Margin About A Subject Tissue" filed Dec. 30, 2019, U.S. patent application Ser. No. 16/729,729 entitled "Surgical Systems For Proposing And Corroborating Organ Portion Removals" filed Dec. 30, 2019, U.S. patent application Ser. No. 16/729,778 entitled "Surgical System For Overlaying Surgical Instrument Data Onto A Virtual Three Dimensional Construct Of An Organ" filed Dec. 30, 2019, U.S. patent application Ser. No. 16/729,751 entitled "Surgical Systems For Generating Three Dimensional Constructs Of Anatomical Organs And Coupling Identified Anatomical Structures Thereto" filed Dec. 30, 2019, U.S. patent application Ser. No. 16/729,740 entitled "Surgical Systems Correlating Visualization Data And Powered Surgical Instrument Data" filed Dec. 30, 2019, U.S. patent application Ser. No. 16/729,737 entitled "Adaptive Surgical System Control According To Surgical Smoke Cloud Characteristics" filed Dec. 30, 2019, U.S. patent application Ser. No. 16/729,796 entitled "Adaptive Surgical System Control According To Surgical Smoke Particulate Characteristics" filed Dec. 30, 2019, U.S. patent application Ser. No. 16/729,803 entitled "Adaptive Visualization By A Surgical System" filed Dec. 30, 2019, and U.S. patent application Ser. No. 16/729,807 entitled "Method Of Using Imaging Devices In Surgery" filed Dec. 30, 2019.

Surgical Procedures of the Lung

Various aspects of the devices, systems, and methods described herein may relate to a surgical procedure performed on a lung. For example, a lung resection, e.g., a lobectomy, is a surgical procedure in which all or part, e.g., one or more lobes, of a lung is removed. The purpose of performing a lung resection is to treat a damaged or diseased lung as a result of, for example, lung cancer, emphysema, or bronchiectasis.

During a lung resection, the lung or lungs are first deflated, and thereafter one or more incisions are made on the patient's side between the patient's ribs to reach the lungs laparoscopically. Surgical instruments, such as graspers and a laparoscope, are inserted through the incision. Once the infected or damaged area of the lung is identified, the area is dissected from the lung and removed from the one or more incisions. The dissected area and the one or more incisions can be closed, for example, with a surgical stapler or stitches.

Since the lung is deflated during surgery, the lung, or certain portions thereof, may need to be mobilized to allow the surgical instruments to reach the surgical site. This mobilization can be carried out by grasping the outer tissue layer of the lung with graspers and applying a force to the lung through the graspers. However, the pleura and parenchyma of the lung are very fragile and therefore can be easily ripped or torn under the applied force. Additionally, during mobilization, the graspers can cut off blood supply to one or more areas of the lung.

Further, a breathing tube is placed into the patient's airway to allow each lung to be separately inflated during surgery. Inflation of the lung can cause the lung to move and match pre-operative imaging and/or allow the surgeon to check for leaks at the dissected area(s). However, by inflating the whole lung, working space is lost around the lung due to the filling of the thoracic cavity. Additionally, inflating a whole lung can take time and does not guarantee easy leak detection if multiple portions of the lung are operated on during the surgical procedure.

Surgical Procedures of the Colon

Figure 21A:
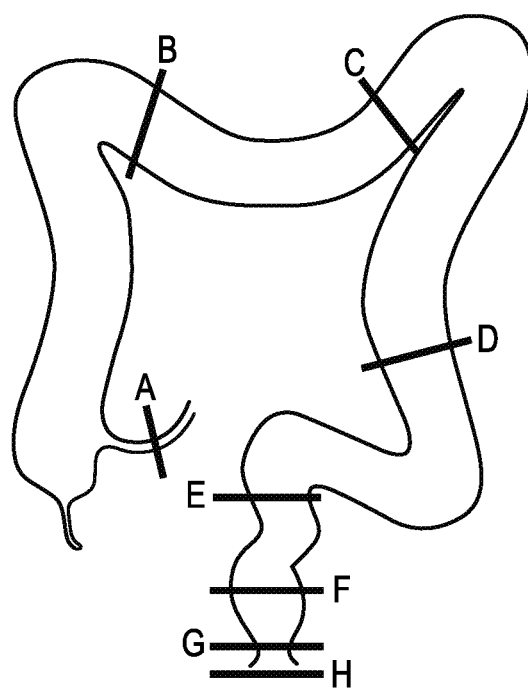
FIG. 21A is a schematic view of a colon illustrating major resections of the colon.

Various aspects of the devices, systems, and methods described herein may relate to a surgical procedure performed on a colon. For example, surgery is often the main treatment for early-stage colon cancers. The type of surgery used depends on the stage (extent) of the cancer, where it is in the colon, and the goal of the surgery. Some early colon cancers (stage 0 and some early stage I tumors) and most polyps can be removed during a colonoscopy. However, if the cancer has progressed, a local excision or colectomy may be required. A colectomy is surgery to remove all or part of the colon. In certain instances, nearby lymph nodes are also removed. If only part of the colon is removed, it's called a hemicolectomy, partial colectomy, or segmental resection in which the surgeon takes out the diseased part of the colon with a small segment of non-diseased colon on either side. Usually, about one-fourth to one-third of the colon is removed, depending on the size and location of the cancer. Major resections of the colon are illustrated in FIG. 21A, in which A-B is a right hemicolectomy, A-C is an extended right hemicolectomy, B-C is a transverse colectomy, C-E is a left hemicolectomy, D-E is a sigmoid colectomy, D-F is an anterior resection, D-G is a (ultra) low anterior resection, D-H is an abdomino-perineal resection, A-D is a subtotal colectomy, A-E is a total colectomy, and A-H is a total procto-colectomy. Once the resection is complete, the remaining intact sections of colon are then reattached.

A colectomy can be performed through an open colectomy, where a single incision through the abdominal wall is used to access the colon for separation and removal of the affected colon tissue, and through a laparoscopic-assisted colectomy. With a laparoscopic-assisted colectomy, the surgery is done through many smaller incisions with surgical instruments and a laparoscope passing through the small incisions to remove the entire colon or a part thereof. At the beginning of the procedure, the abdomen is inflated with gas, e.g., carbon dioxide, to provide a working space for the surgeon. The laparoscope transmits images inside the abdominal cavity, giving the surgeon a magnified view of the patient's internal organs on a monitor or other display. Several other cannulas are inserted to allow the surgeon to work inside and remove part(s) of the colon. Once the diseased parts of the colon are removed, the remaining ends of the colon are attached to each other, e.g., via staplers or stitches. The entire procedure may be completed through the cannulas or by lengthening one of the small cannula incisions.

During a laparoscopic-assisted colectomy procedure, it is often difficult to obtain an adequate operative field. Oftentimes, dissections are made deep in the pelvis which makes it difficult to obtain adequate visualization of the area. As a result, the lower rectum must be lifted and rotated to gain access to the veins and arteries around both sides of the rectum during mobilization. During manipulation of the lower rectum, bunching of tissue and/or overstretching of tissue can occur. Additionally, a tumor within the rectum can cause adhesions in the surrounding pelvis, and as a result, this can require freeing the rectal stump and mobilizing the mesentery and blood supply before transection and removal of the tumor.

Further, multiple graspers are needed to position the tumor for removal from the colon. During dissection of the colon, the tumor should be placed under tension, which requires grasping and stretching the surrounding healthy tissue of the colon. However, the manipulating of the tissue surrounding the tumor can suffer from reduced blood flow and trauma due to the graspers placing a high grip force on the tissue. Additionally, during a colectomy, the transverse colon and upper descending colon may need to be mobilized to allow the healthy, good remaining colon to be brought down to connect to the rectal stump after the section of the colon containing the tumor is transected and removed.

After a colectomy, the remaining healthy portions of the colon must be reattached to one another to create a path for waste to leave the body. However, when using laparoscopic instruments to perform the colectomy, one single entry port may not have a large enough range of motion to move the one end of the colon to a connecting portion of the colon. As such, a second entry port is therefore needed to laparoscopically insert surgical instruments to help mobilize the colon in order to properly position the colon.

Surgical Procedures of the Stomach

Various aspects of the devices, systems, and methods described herein may relate to a surgical procedure performed on a stomach. For example, surgery is the most common treatment for stomach cancer. When surgery is required for stomach cancer, the goal is to remove the entire tumor as well as a good margin of healthy stomach tissue around the tumor. Different procedures can be used to remove stomach cancer. The type of procedure used depends on what part of the stomach the cancer is located and how far it has grown into nearby areas. For example, endoscopic mucosal resection (EMR) and endoscopic submucosal dissection (ESD) are procedures on the stomach can be used to treat some early-stage cancers. These procedures do not require a cut in the skin, but instead the surgeon passes an endoscope down the throat and into the stomach of the patient. Surgical tools (e.g., MEGADYNE™ Tissue Dissector or Electrosurgical Pencils) are then passed through the working channel of the endoscope to remove the tumor and some layers of the normal stomach wall below and around it.

Other surgical procedures performed on a stomach include a subtotal (partial) or a total gastrectomy that can be performed as an open procedure. e.g., surgical instruments are inserted through a large incision in the skin of the abdomen, or as a laparoscopic procedure, e.g., surgical instruments are inserted into the abdomen through several small cuts. For example, a laparoscopic gastrectomy procedure generally involves insufflation of the abdominal cavity with carbon dioxide gas to a pressure of around 15 millimeters of mercury (mm Hg). The abdominal wall is pierced and a straight tubular cannula or trocar, such as a cannula or trocar having a diameter in a range of about 5 mm to about 10 mm, is then inserted into the abdominal cavity. A laparoscope connected to an operating room monitor is used to visualize the operative field and is placed through one of the trocar(s). Laparoscopic surgical instruments are placed through two or more additional cannulas or trocars for manipulation by medical practitioner(s), e.g., surgeon and surgical assistant(s), to remove the desired portion(s) of the stomach.

In certain instances, laparoscopic and endoscopic cooperative surgery can be used to remove gastric tumors. This cooperative surgery typically involves introduction of an endoscope, e.g., a gastroscope, and laparoscopic trocars. A laparoscope and tissue manipulation and dissection surgical instruments are introduced through the trocar. The tumor location can be identified via the endoscope and a cutting element that is inserted into the working channel of the endoscope is then used for submucosal resection around the tumor. A laparoscopic dissection surgical instrument is then used for seromuscular dissection adjacent the tumor margins to create an incision through the stomach wall. The tumor is then pivoted through this incision from the intraluminal space, e.g., inside the stomach, to the extraluminal space, e.g., outside of the stomach. A laparoscopic surgical instrument, e.g., an endocutter, can be used to then complete the transection of the tumor from the stomach wall and seal the incision.

Surgical Procedures of the Intestine

Various aspects of the devices, systems, and methods described herein may relate to a surgical procedure performed on an intestine. For example, a duodenal mucosal resurfacing (DMR) procedure can be performed endoscopically to treat insulin-resistant metabolic diseases such as type 2 diabetes. The DMR procedure can be an effective treatment because it affects detection of food. The DMR procedure inhibits duodenum function such that food tends to be sensed deeper in the intestine than normal, e.g., sensed after passage through the duodenum (which is the first part of the small intestine). The patient's body thus senses sugar deeper in the intestine than is typical and thus reacts to the sugar later than is typical such that glycemic control can be improved. The irregular function of the duodenum changes the body's typical response to the food and, through nervous system and chemical signals, causes the body to adapt its response to the glucose level to increase insulin levels.

In the DMR procedure, the duodenal mucosa is lifted, such as with saline, and then the mucosa is ablated, e.g., using an ablation device advanced into the duodenum through a working channel of an endoscope. Lifting the mucosa before ablation helps protect the duodenum's outer layers from being damaged by the ablation. After the mucosa is ablated, the mucosa later regenerates. Examples of ablation devices are NeuWave™ ablation probes (available from Ethicon US LLC of Cincinnati, OH). Another example of an ablation device is the Hyblate catheter ablation probe (available from Hyblate Medical of Misgav, Israel). Another example of an ablation device is the Barxx™ HaloFlex (available from Medtronic of Minneapolis, MN).

Figure 21B:
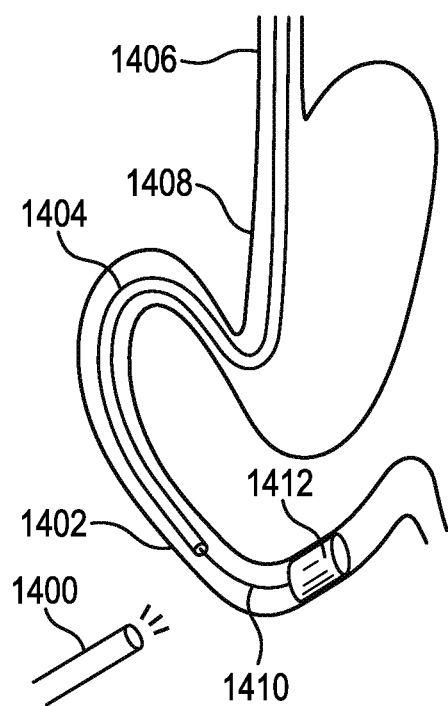
FIG. 21B is a perspective partial cross-sectional view of one embodiment of a duodenal mucosal resurfacing procedure.

FIG. 21B illustrates one embodiment of a DMR procedure. As shown in FIG. 21B, a laparoscope 1400 is positioned external to a duodenum 1402 for external visualization of the duodenum 1402. An endoscope 1404 is advanced transorally through an esophagus 1406, through a stomach 1408, and into the duodenum 1402 for internal visualization of the duodenum 1402. An ablation device 1410 is advanced through a working channel of the endoscope 1404 to extend distally from the endoscope 1404 into the duodenum 1402. A balloon 1412 of the ablation device 1410 is shown expanded or inflated in FIG. 21B. The expanded or inflated balloon 1412 can help center the ablation device's electrode so even circumferential ablating can occur before the ablation device 1410 is advanced and/or retracted to repeat ablation. Before the mucosa is ablated using the ablation device 1410, the duodenal mucosa is lifted, such as with saline. In some embodiments in addition to or instead of including the balloon 1412, the ablation device 1410 can be expandable/collapsible using an electrode array or basket configured to expand and collapse.

The laparoscope's external visualization of the duodenum 1402 can allow for thermal monitoring of the duodenum 1402, which may help ensure that the outer layers of the duodenum 1402 are not damaged by the ablation of the duodenal mucosa, such as by the duodenum being perforated. Various embodiments of thermal monitoring are discussed further, for example, below and in U.S. Pat. App No. 63/249,658 entitled "Surgical Devices, Systems, And Methods For Control Of One Visualization With Another" filed on Sep. 29, 2021. The endoscope 1404 and/or the ablation device 1410 can include a fiducial marker thereon that the laparoscope 1400 can be configured to visualize through the duodenum's tissue, e.g., by using invisible light, to help determine where the laparoscope 1400 should externally visualize the duodenum 1402 at a location where ablation occurs. Various embodiments of fiducial markers are discussed further, for example, in U.S. Pat. App No. 63/249,652 entitled "Surgical Devices, Systems, Methods Using Fiducial Identification And Tracking" filed on Sep. 29, 2021 and in U.S. Pat. App No. 63/249,658 entitled "Surgical Devices, Systems, And Methods For Control Of One Visualization With Another" filed on Sep. 29, 2021.

Control of Cooperative Surgical Instruments

In various aspects, the present disclosure provides methods, devices, and systems for the control of cooperative surgical instruments with variable surgical site access trajectories. In one aspect, such a system can include a first surgical instrument configured to be inserted into a first body cavity of a patient and to operate on a region of tissue from the first body cavity, and the system can include a second surgical instrument configured to be inserted into a second body cavity that differs from the first body cavity and to operate on the region of tissue from the second body cavity. The system can further include a first endoscope having a first image sensor configured to acquire a first image of the first surgical instrument within the first body cavity and positioned such that the second surgical instrument is not within a field of view of the first image sensor, and the system can further include a second endoscope having a second image sensor configured to acquire a second image of the second surgical instrument within the second body cavity and positioned such that the first surgical instrument is not within a field of view of the second image sensor. The system can further include a controller configured to receive the acquired first and second images, to determine a first location of the first surgical instrument and a second location of the surgical instrument, and to coordinate cooperative operation of the first and second surgical instruments relative to each other based on the determined first and second locations.

Figure 22:
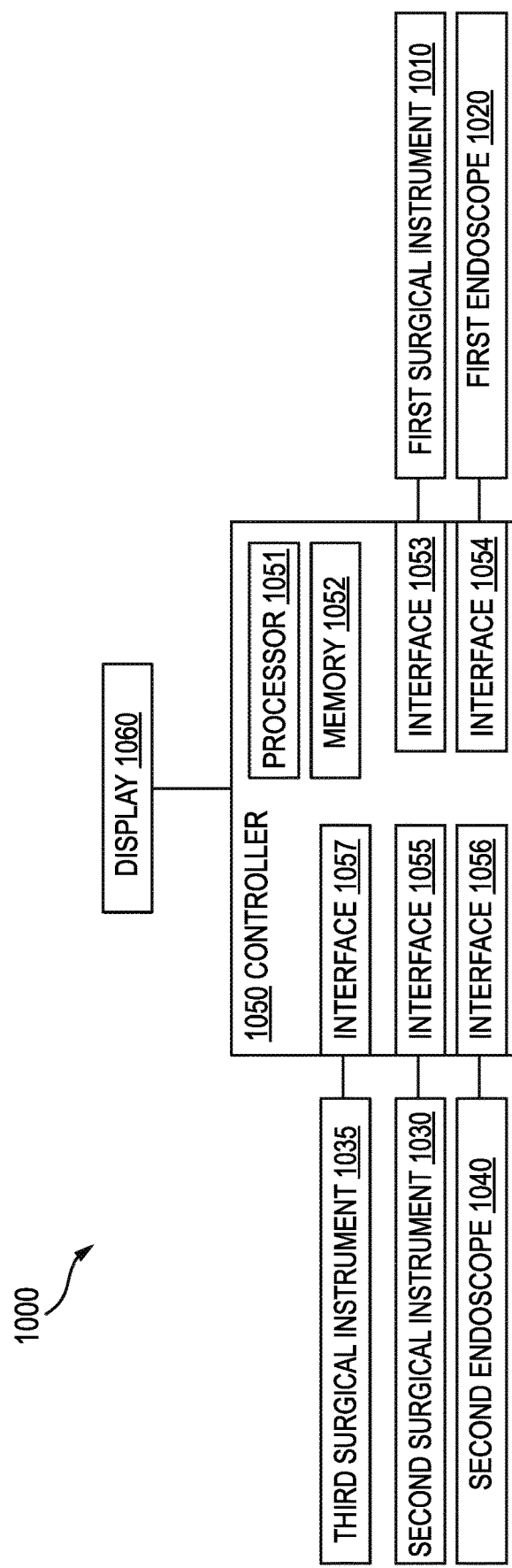
FIG. 22 is a schematic diagram of an exemplary surgical system that can provide for cooperative control of surgical instruments having variable surgical site access trajectories.

FIG. 22 provides a schematic of one exemplary surgical system 1000 that can provide for cooperative control of surgical instruments having variable surgical site access trajectories. As shown, the system 1000 includes a first surgical instrument 1010 configured to be inserted into a first body cavity, a first endoscope 1020 configured to be inserted into the first body cavity and to visualize the first surgical instrument 1010 when inserted into the first body cavity, second and third surgical instruments 1030, 1035 configured to be inserted into a second body cavity, and a second endoscope 1040 configured to be inserted into the second body and to visualize the second and third surgical instruments 1030, 1035. The first surgical instrument 1010, the first endoscope 1020, the second surgical instrument 1040, the second endoscope 1040, and the third surgical instrument 1035 can be in operable communication with a controller 1050 of the system 1000 that is configured to control/coordinate the operation of the first, second, and third surgical instruments based on images received from the first and second endoscopes 1020, 1040, as explained in further detail below.

The first surgical instrument 1010, the second surgical instrument 1030, and the third surgical instrument 1035 can each be any suitable surgical device configured to manipulate and/or treat tissue. The first surgical instrument 1010, the second surgical instrument 1030, and the third surgical instrument 1035 can each be similar to the surgical device 102 of FIG. 1, the surgical device 202 of FIG. 8, or other surgical device described herein. As mentioned above, examples of surgical devices include a surgical dissector, a surgical stapler, a surgical grasper, a clip applier, a smoke evacuator, a surgical energy device (e.g., mono-polar probes, bi-polar probes, ablation probes, an ultrasound device, an ultrasonic end effector, etc.), etc. For example, in some embodiments, the first surgical instrument 1010, the second surgical instrument 1030, and/or the third surgical instrument 1035 can include an end effector having opposing jaws that extend from a distal end of a shaft of the surgical device and that are configured to engage tissue therebetween.

The first endoscope 1020 and the second endoscope 1040 can each include an imaging device configured to acquire an image of a surgical site in a minimally invasive surgical procedure. The first endoscope 1020 and the second endoscope 1040 can each be similar to the imaging device 120 of FIG. 1, the imaging device 220 of FIG. 8, or other imaging device described herein. Although some implementations of the current subject matter are described herein as using one or more endoscopes to acquire images of the surgical site, any type of scope suitable for use in a minimally invasive surgical procedure can be used in conjunction with the systems, methods, and devices described herein. As mentioned above, examples of scopes include an arthroscope, an angioscope, a bronchoscope, a choledochoscope, a colonoscope, a cytoscope, a duodenoscope, an enteroscope, an esophagogastro-duodenoscope (gastroscope), a laryngoscope, a nasopharyngo-neproscope, a sigmoidoscope, a thoracoscope, an ureteroscope, and an exoscope. One or more of these exemplary types of scopes can be used together in a minimally invasive surgical procedure in any feasible combination. In some embodiments, at least one of the first endoscope 1020 and the second endoscope 1040 includes a distal stabilization balloon. Various embodiments of distal stabilization balloons are further described in, for example, previously mentioned U.S. Pat. App No. 63/249,980 entitled "Cooperative Access" filed on Sep. 29, 2021.

The controller 1050 includes a processor 1051 configured to perform one or more of operations, including the operations described herein, and a memory 1052 that is configured to store instructions for causing the processor 1051 to perform the operations. The controller 1050 also includes a first surgical instrument interface 1053, a first endoscope interface 1054, a second surgical instrument interface 1055, a second endoscope interface 1056, and a third surgical instrument interface 1057. As shown in FIG. 22, the first surgical instrument 1010 is coupled to the controller 1050 via the first surgical instrument interface 1053 and as such can receive operating/actuating instructions from the processor 1051. The first endoscope 1020 is coupled to the controller 1050 via the first endoscope interface 1054, and as such can provide data characterizing images acquired by the first endoscope 1020 to the processor 1051, and/or the memory 1052 for later use by the processor 1051 in performing the operations described herein. Similar to the first surgical instrument 1010, the second surgical instrument 1030 is coupled to the controller 1050 via the second surgical instrument interface 1055 and as such can receive operating/actuating instructions from the processor 1051, and the third surgical instrument 1035 is coupled to the controller 1050 via the third surgical instrument interface 1057 and as such can receive operating/actuating instructions from the processor 1051. Similar to the first endoscope 1020, the second endoscope 1040 is coupled to the controller 1050 via the second endoscope interface 1056 and as such can provide data characterizing images acquired by the second endoscope 1040 to the processor 1051 and/or the memory 1052 for later use by the processor 1051 in performing the operations described herein. In some embodiments, each of the first surgical instrument interface 1053, the first endoscope interface 1054, the second surgical instrument interface 1055, the second endoscope interface 1056, and the third surgical instrument interface 1057 may be different from one another so as to accommodate differences between the controller interfaces of various ones of the first surgical instrument 1010, the first endoscope 1020, the second surgical instrument 1030, the second endoscope 1040, and the third surgical instrument 1035.

As shown, the system 1000 can also include a display 1060 that is operably coupled to the controller 1050 and configured to graphically depict the images acquired by one or more of the first endoscope 1020 and the second endoscope 1040. In some embodiments, the controller 1050 can receive a stream of image data from each of the first endoscope 1020 and the second endoscope 1040, determine an image and/or video feed in real-time from the received image data, and provide the image and/or video feed to the display 1060 for depiction thereon and viewing by a user. The system 1000, the controller 1050, and/or the display 1060 can be incorporated into various robotic surgical systems and/or can be part of a surgical hub, as discussed above.

Figure 23:
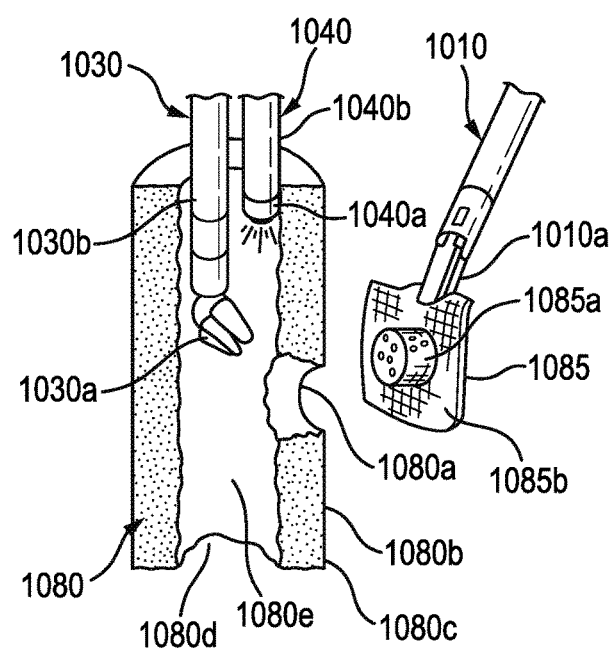
FIG. 23 is an illustrative view of an example embodiment of a system for cooperatively placing an implant at a surgical site of a lumen structure using multiple surgical instruments that approach the surgical site from within and outside of the lumen structure.

FIG. 23 shows one embodiment of a surgical system being utilized to cooperatively place an implant, such as an adjunct, at a lumen structure (e.g., a hollow organ or body lumen such as an esophagus, blood vessel, intestine, etc.) using multiple surgical instruments that approach the lumen structure from within and outside of the lumen structure and when it is not possible to visualize all of the surgical instruments with one endoscope. FIG. 23 is described with respect to the surgical system 1000 of FIG. 22 but another surgical system as described herein can be similarly used.

Figure 24:
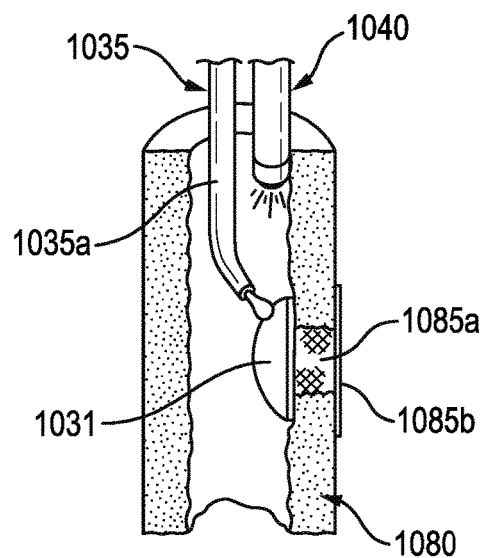
FIG. 24 shows the system of FIG. 23 after the implant has been applied to the surgical site, and an exemplary instrument is in the process of fixing the implant of FIG. 23 in place at the surgical site.

As shown in FIG. 23, the first surgical instrument 1010 is inserted into a first body cavity of a patient, outside of a lumen structure, an esophagus 1080 in this illustrated embodiment, and operates on a target area 1080*a* of the esophagus 1080. The target area 1080*a* in the illustrated embodiment is a hole formed in a sidewall 1080*b* of the esophagus 1080, but other surgical procedures can have another target area. As shown, the first surgical instrument 1010 is a grasper configured to deliver an adjunct 1085 to the target area 1080*a*. The adjunct 1085 in this illustrated embodiment includes a porous plug section 1085*a* that is configured to be inserted laparoscopically into the target area 1080*a*. The porosity of the porous plug section 1085*a* of the adjunct 1085 can be configured to promote tissue ingrowth, and the porous plug section 1085*a* can be bioabsorbable. The adjunct 1085 in this illustrated embodiment also includes an adhesive wrap section 1085*b*, such as a Vicryl® adhesive wrap, that is coupled to, and configured to support, the porous plug section 1085*a*. The adhesive wrap section 1085*b* can be bioabsorbable. The adhesive wrap section 1085*b* is configured to be positioned outside of the esophagus 1080 with the porous plug section 1085*a* inserted into the target area 1080*a*, as shown in FIG. 24. In some embodiments, the porous plug section 1085*a* and the adhesive wrap section 1085*b* can be integrally formed instead of being two separate components fixed together.

As mentioned above, the adjunct 1085 can be bioabsorbable. For a bioabsorbable adjunct, the material(s) forming the adjunct can include bioabsorbable and biocompatible polymers, including homopolymers and copolymers. Examples of homopolymers and copolymers include p-dioxanone (PDO or PDS), polyglycolic acid (PGA), poly (lactic-co-glycolic acid) (PLGA), polycaprolactone (PCL), trimethylene carbonate (TMC), and polylactic acid (PLA), poly(glycolic acid-co-lactic acid) (PLA/PGA) (e.g., PLA/PGA materials used in Vicryl®, Vicryl Rapide™, PolySorb, and Biofix), polyurethanes (such as Elastane, Biospan, Tecoflex, Bionate, and Pellethane fibers), polyorthoesters, polyanhydrides (e.g., Gliadel and Biodel polymers), polyoxaesters, polyesteramides, and tyrosine-based polyesteramides. The copolymers can also include poly (lactic acid-co-polycaprolactone) (PLA/PCL), poly(L-lactic acid-co-polycaprolactone) (PLLA/PCL), poly(glycolic acid-co-trimethylene carbonate) (PGA/TMC) (e.g., Maxon), Poly (glycolic acid-co-caprolactone) (PCL/PGA) (e.g., Monocryl and Capgly), PDS/PGA/TMC (e.g., Biosyn), PDS/PLA, PGA/PCL/TMC/PLA (e.g., Caprosyn), and LPLA/DLPLA (e.g., Optima).

Various embodiments of adjuncts and implanting adjuncts are discussed further in U.S. Pat. Pub. No. 2018/0353174 filed Jun. 13, 2017 and entitled "Surgical Stapler with Controlled Healing," U.S. Pat. No. 10,569,071 entitled "Medicant Eluting Adjuncts And Methods Of Using Medicant Eluting Adjuncts" issued Feb. 25, 2020, U.S. Pat. No. 10,716,564 entitled "Stapling Adjunct Attachment" issued Jul. 21, 2020, U.S. Pat. Pub. No. 2013/0256377 entitled "Layer Comprising Deployable Attachment Members" filed Feb. 8, 2013, U.S. Pat. No. 8,393,514 entitled "Selectively Orientable Implantable Fastener Cartridge" filed Sep. 30, 2010, U.S. Pat. No. 8,317,070 entitled "Surgical Stapling Devices That Produce Formed Staples Having Different Lengths" filed Feb. 28, 2007, U.S. Pat. No. 7,143,925 entitled "Surgical Instrument Incorporating EAP Blocking Lockout Mechanism" filed Jun. 21, 2005, U.S. Pat. Pub. No. 2015/0134077 entitled "Sealing Materials For Use In Surgical Stapling" filed Nov. 8, 2013, U.S. Pat. Pub. No. 2015/0134076, entitled "Hybrid Adjunct Materials for Use in Surgical Stapling" filed on Nov. 8, 2013, U.S. Pat. Pub. No. 2015/0133996 entitled "Positively Charged Implantable Materials and Method of Forming the Same" filed on Nov. 8, 2013, U.S. Pat. Pub. No. 2015/0129634 entitled "Tissue Ingrowth Materials and Method of Using the Same" filed on Nov. 8, 2013, U.S. Pat. Pub. No. 2015/0133995 entitled "Hybrid Adjunct Materials for Use in Surgical Stapling" filed on Nov. 8, 2013, U.S. Pat. Pub. No. 2015/0272575 entitled "Surgical Instrument Comprising a Sensor System" and filed on Mar. 26, 2014, U.S. Pat. Pub. No. 2015/0351758 entitled "Adjunct Materials and Methods of Using Same in Surgical Methods for Tissue Sealing" filed on Jun. 10, 2014, U.S. Pat. Pub. No. 2013/0146643 entitled "Adhesive Film Laminate" filed Feb. 8, 2013, U.S. Pat. No. 7,601,118 entitled "Minimally Invasive Medical Implant And Insertion Device And Method For Using The Same" filed Sep. 12, 2007, and U.S. Pat. Pub. No. 2013/0221065 entitled "Fastener Cartridge Comprising A Releasably Attached Tissue Thickness Compensator" filed Feb. 8, 2013, which are each hereby incorporated by reference herein in their entireties.

As shown in FIG. 23, the second surgical instrument 1030 is inserted into an inner lumen 1080d of the esophagus 1080 to facilitate the positioning of the porous plug portion 1085a of the adjunct 1085 into the target area 1080a from within the esophagus 1080. The adjunct 1085 can thus be cooperatively implanted into the lumen structure 1080 from within the lumen structure 1080 (using the second surgical instrument 1030) and from outside the lumen structure 1080 (using the first surgical instrument 1010). As shown in FIG. 23, the second surgical instrument 1030 includes a grasper portion 1030a that is disposed at a distal end of a shaft 1030b of the second surgical instrument 1030 and that grasps the porous plug portion 1085a of the adjunct 1085, through the target area 1080a, when the adjunct 1085 is maneuvered in proximity to the target area 1080a by the first surgical instrument 1010 from outside the esophagus 1080.

As shown in FIG. 23, the second endoscope 1040 is inserted into the inner lumen 1080d of the esophagus 1080 to visualize the inner lumen 1080d, the second and third surgical instruments 1030, 1035 located in the inner lumen 1080d (not necessarily in the inner lumen 1080d at the same time), and the porous plug section 1085a of the adjunct 1085 when inserted into the target area 1080a. The second endoscope 1040 includes a second image sensor 1040a and a shaft 1040b. As shown, the second image sensor 1040a is located at a distal end of the shaft 1040b. The second image sensor 1040a can be a camera or another type of image sensor as described herein and is configured to acquire an image of the inner lumen 1080d, the second and third surgical instruments 1030, 1035 (not necessarily in the inner lumen 1080d at the same time), and the porous plug section 1085a of the adjunct 1085, and to provide data characterizing the acquired image to the controller 1050 for visualization and analysis as described below.

The first surgical instrument 1010 is visualized by the first endoscope 1020 (not shown in FIG. 23 or FIG. 24), which can be inserted into a same body cavity as the first surgical instrument 1010 and be located outside of the esophagus 1080 such that the first surgical instrument 1010, an outer surface 1080c of the sidewall 1080b, the target area 1080a, and the adjunct 1085 being held by the first surgical instrument 1010 and subsequently implanted at the esophagus 1080 are within a field of view of an image sensor of the first endoscope 1020. As explained above, each of first surgical instrument 1010 and first endoscope 1020 are in operable communication with the controller 1050.

The second endoscope 1040 positioned within the esophagus 1080 is unable to visualize (at least using visible light) the first surgical instrument 1010 and the first endoscope 1020 positioned outside the esophagus 1080, as the sidewall 1080b of the esophagus 1080 obstructs the view of the first surgical instrument 1010 and the first endoscope 1020 by the second endoscope 1040. The second endoscope 1040 may, depending on its location within the esophagus 1080, have visualization of the first surgical instrument 1010 and/or the first endoscope 1020 through the hole 1080a, but such visualization if present at all will be limited due to the hole's generally small size and the second endoscope's limited ability to maneuver in the inner lumen 1080d, and such visualization will be obstructed entirely with the porous plug section 1085a of the adjunct 1085 inserted into the target area 1080a. Similarly, the first endoscope 1020 will be unable to visualize (at least using visible light) the second or third surgical instruments 1030, 1035 and the second endoscope 1040, as the view of the second and third surgical instruments 1030, 1035 and the second endoscope 1040, by the first endoscope 1020 is similarly obstructed by the sidewall 1080b of the esophagus 1080. The first endoscope 1020 may, depending on its location outside the esophagus 1080, have visualization of the second surgical instrument 1030, the third surgical instrument 1035 and/or the second endoscope 1040 through the hole 1080a, but such visualization if present at all will be limited due to the hole's generally small size, and such visualization will be obstructed entirely with the porous plug section 1085a of the adjunct 1085 inserted into the target area 1080a.

In the illustrated embodiment, the third surgical instrument 1035 is used to deliver a cooperative fixating implant, such as an adhesive material, to the target area 1080a from within the lumen structure 1080 to help maintain the adjunct 1085 in place at the target area 1080a by the cooperative fixating implant. As shown in FIG. 24, the third surgical instrument 1035 includes an adhesive syringe 1035a that is configured to deliver adhesive material 1031 to an inner surface 1080e of the esophagus 1080 over and in proximity to the porous plug portion 1085a of the adjunct 1085 when inserted into the target area 1080a. The adhesive material 1031 is configured to fix the porous plug portion 1085a of the adjunct in place in the hole 1080a. In other embodiments, the cooperative fixating implant can be a suture, and the third surgical instrument 1035 can be an endoscopic suturing device (not shown) configured to apply a suture the porous plug portion 1085a of the adjunct 1085 to tie the porous plug portion 1085a in place in the hole 1080a. Additionally, while the illustrated embodiment uses the third surgical instrument 1035 to deliver a cooperative fixating implant, in other embodiments, the second surgical instrument 1030 can deliver a cooperative fixating implant such that a single surgical instrument (the second surgical instrument 1030) can grasp the adjunct 1085 and deliver the cooperative fixating implant to the target area 1080a from within the lumen structure 1080, which may simplify the procedure.

As mentioned above, the controller 1050 can be used to control movements and actuations of each of the first, second, and third surgical instruments 1010, 1030, 1035 to thereby achieve coordinated operation of the first, second, and third surgical instruments 1010, 1030, 1035 such that a common surgical purpose (e.g., the fixation of the adjunct 1085 in the surgical site 1080*a*) may be efficiently and effectively obtained. In an example use of the surgical system 1000, with reference to FIG. 22-FIG. 24, the first endoscope 1020 is inserted into first body cavity of the patient outside of the patient's lumen structure 1080, and the second endoscope 1040 is inserted into the lumen structure 1080 of the patient. The first surgical instrument 1010, having the adjunct 1085 coupled to an end effector 1010*a* thereof, is then inserted into first body cavity of the patient, and the second surgical instrument 1030 is inserted into the lumen structure of the patient. Under visualization by the endoscopes 1020, 1040, the first surgical instrument 1110 and the second surgical instrument 1030 are maneuvered close to the surgical site 1080*a* in which the adjunct 1085*a* is to be placed, such that the first surgical instrument 1010 is within the field of view of the first endoscope 1020 (but not the second endoscope 1040), and that the second surgical instrument 1030 is within the field of view of the second endoscope 1040 (but not the first endoscope 1020). In some embodiments, the first instrument 1010 and the first endoscope 1020 are positioned relative to the lumen structure 1080 before the second instrument 1030 and the second endoscope 1040 are positioned relative to the lumen structure 1080, or vice versa with the second instrument 1030 and the second endoscope 1040 being positioned relative to the lumen structure 1080 before the first instrument 1010 and the first endoscope 1020 are positioned relative to the lumen structure 1080.

The controller 1050 is configured to receive one or more images of the first surgical instrument 1010 from the first endoscope 1020, and one or more images of the second surgical instrument 1030 from the second endoscope 1040. Additionally, the location and orientation of each endoscope 1020, 1040 is tracked by the controller 1050 of the system 1000 using electromagnetic (EM) tracked tips of each endoscope 1020, 1040 through magnetic field detection to determine locations and orientations of each endoscope 1020, 1040 in a global coordinate system of the system 1000, which is known by the controller 1050 in communication with each of the endoscopes 1020, 1040 and each of the surgical instruments 1010, 1030. While EM tracked tips are provided in the illustrated embodiment, alternative and/or additional tracking means can be used, such as fiber bragg grating, virtual tags, fiducial markers, use of probes, identification of known anatomy, various 3D scanning techniques such as using structured light, various sensors and/or imaging systems discussed above, etc. Additional details regarding various embodiments of tracking surgical instruments are provided in, for example, previously mentioned U.S. App. No. 63/249,980 entitled "Cooperative Access" filed on Sep. 29, 2021.

Thus, based on received images from the first and second endoscopes 1020, 1040 of the first and second surgical instruments 1010, 1030 and the tracked locations and orientations of the first and second endoscopes 1020, 1040, the controller 1050 is configured to determine locations and orientations of the first and second instruments 1010, 1030. As the controller 1050 monitors movement of the first and second surgical instruments 1010, 1030, the first surgical instrument 1010 maneuvers the adjunct 1085 to the surgical site 1080*a*, and the second surgical instrument 1030 grasps and assists in placement of the adjunct 1085 from within the esophagus 1080, as needed. Once the controller 1050 confirms placement of the adjunct 1085 based on visualization by the endoscopes 1020, 1040, the second surgical instrument 1030 is withdrawn from the esophagus 1080, and the third surgical instrument 1035 is maneuvered to the surgical site 1080*a* at a position within the esophagus 1080 and applies the cooperative fixating implant (such as adhesive material 1031) to the adjunct 1085 and surrounding regions of the inner surface 1080*e* of the esophagus 1080 to fix the adjunct 1085 in place at the surgical site 1080*a*. There are thus only two instruments, either the first and second surgical instruments 1010, 1030 or the first and third surgical instruments 1010, 1035, in use at a time during deployment of the adjunct 1085. Furthermore, in some embodiments, coordinated operation of two or more of the first, second, and third surgical instruments 1010, 1030, 1035 occurs at least in part simultaneously, such as when positioning the adjunct 1085 and/or deploying the cooperative fixating implant to ensure proper placement of the adjunct 1085.

While the illustrated embodiment in FIG. 22-FIG. 24 provides for repair of the surgical site 1080*a* in the patient's esophagus 1080, a variety of different procedures are possible in different embodiments similarly involving cooperative interaction of at least the instruments 1010, 1030 from both intraluminal and extraluminal sides of a target treatment site for successful deployment of various different intraluminal or extraluminal implants that are introduced either intraluminally or extraluminally, such as when deploying various implants around an esophageal sphincter of the patient to treat gastroesophageal reflux disease.

Figure 24A:
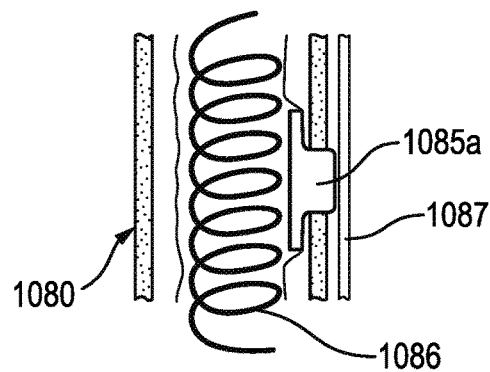
FIG. 24A shows the system of FIG. 23 after the implant has been applied to the surgical site, and several different embodiments of repair implants are disposed at the surgical site.

Furthermore, in some embodiments, other repair mechanisms can be used to assist in repairing the target area 1080*a* in addition to or instead of the adjunct 1085. For example, FIG. 24A illustrates one embodiment of an esophageal stent 1086 that is placed endoscopically in the esophagus 1080 by the second surgical instrument 1030 to minimize force loads placed on the surgical site 1080*a* during healing, and one embodiment of a laparoscopic wrap 1087 is applied laparoscopically at the surgical site 1080*a*, such as by the first instrument 1010, to provide increased support during healing. The laparoscopic wrap 1087 is not the adhesive wrap section 1085*b* of the adjunct 1085, discussed above, but the laparoscopic wrap 1087 can be made of similar materials and can be bioabsorbable.

In some embodiments, surgical instruments in two isolated body cavities can be controlled by a controller (e.g., a controller of a surgical hub, a robotic surgical system, or other computer system) such that the surgical instruments can cooperatively interact with opposed surfaces of a common tissue or organ between two body cavities. Furthermore, the controller can impose interrelated limits on various actuations, such as interrelated force or range of motion threshold limits, incorporated into each surgical instrument such that the surgical instruments can cooperatively operate to achieve a common surgical purpose without maneuvering in such a way that could unintentionally damage tissue.

Figure 25:
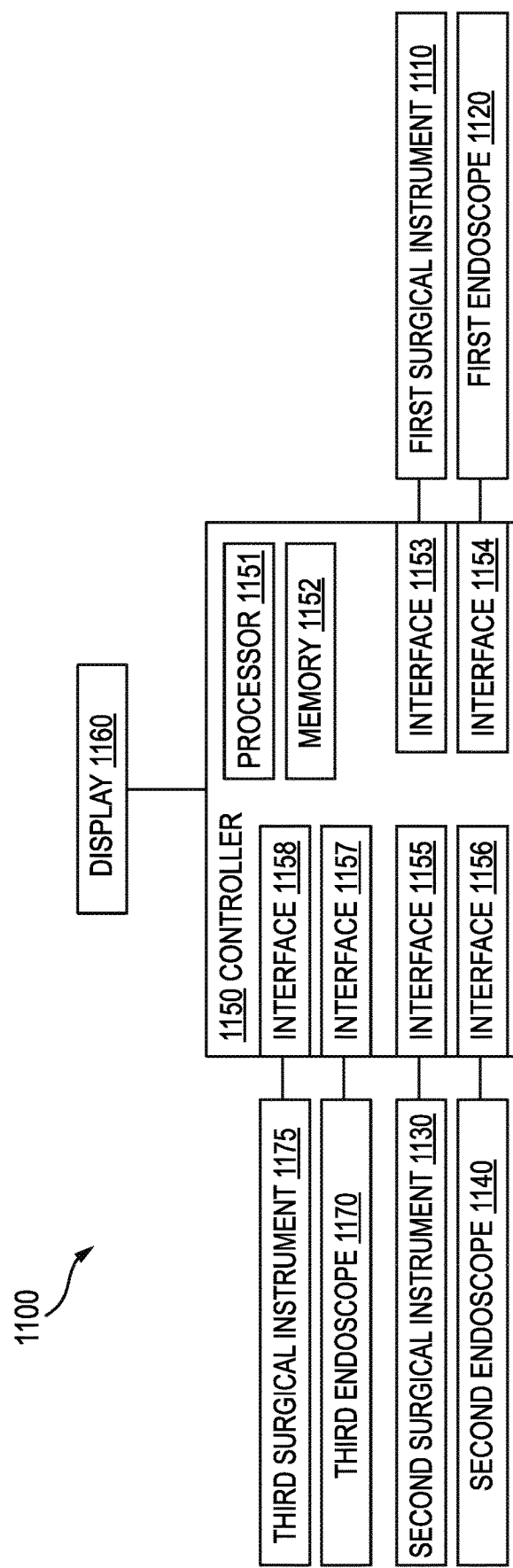
FIG. 25 is a schematic diagram of an exemplary surgical system that can provide for common field of view by augmenting multiple positions from the tracking of sensors placed on endoscopes placed in a surgical field.

FIG. 25 shows one exemplary surgical system 1100 that can be utilized to provide a common field of view by augmenting multiple positions from the tracking of sensors placed on endoscopes placed in a surgical field. Each of the below-described components of system 1100 is generally configured and used similar to like-named elements in the system 1000 described above.

The system 1100 includes a first surgical instrument 1110 configured to be inserted into a first body cavity, a first endoscope 1120 configured to be inserted into the first body cavity and to visualize the first surgical instrument 1110 when inserted into the first body cavity, a second surgical instrument 1130 configured to be inserted into a second body cavity, a second endoscope 1140 configured to be inserted into the second body cavity and to visualize the second surgical instrument 1130, and a third surgical instrument 1175 configured to be inserted into one of the first and second body cavities and to manipulate tissue. The system 1110 also includes first, second, and third surgical instrument interfaces 1153, 1155, 1158, and first and second endoscope interfaces 1154, 1156. The first surgical instrument 1110, the first endoscope 1120, the second surgical instrument 1130, the second endoscope 1140, and the third surgical instrument 1175 are in operable communication with a controller 1150 of the system 1100 that is configured to control the operation of the first, second, and third surgical instruments, as explained in further detail below. As illustrated in FIG. 25, the system 1100 also includes a third endoscope 1170 that is configured to be inserted into a third body cavity different from each of the first body cavity and the second body cavity and to visualize the third body cavity. As shown, the third endoscope 1170 is coupled to the controller 1150 via a third endoscope interface 1157 generally configured and used similar to the first endoscope interface 1154 and the second endoscope interface 1156. The Similar to the system 1000 described above, the system 1100 also includes a display 1160 that is operably coupled to the controller 1150 and configured to graphically depict images acquired by one or more of the first endoscope 1120, the second endoscope 1140, and the third endoscope 1170 and received by the controller 1150 via the respective interfaces 1154, 1156, 1157.

FIG. 26 shows one embodiment of providing a common field of view by augmenting multiple points of view into the common field of view via the use of sensors on a plurality of endoscopes located in a surgical field. As shown in FIG. 26, the first surgical instrument 1110 is a grasper configured to be inserted through a rib access Cl into a first body cavity, which is a thoracic cavity C in this illustrated embodiment, outside of a lumen structure of a patient, which is an esophageal orifice B in this illustrated embodiment, and to operate on tissue accessible via the thoracic cavity C. Similar to first surgical instrument 1110, the second surgical instrument 1130 and the third surgical instrument 1175 are each a laparoscopic grasper that is inserted into the abdominal cavity A and configured to manipulate the tissue accessible within a second body cavity, which is an abdominal cavity A, in this illustrated embodiment. However, other types of surgical instruments described elsewhere herein may be utilized as appropriate for the surgical field and procedure.

As shown in FIG. 26, similar to the first and second endoscopes 1020, 1040 of the system 1000, the first, second, and third endoscopes 1120, 1140, 1170 each include a shaft 1120a, 1140a, 1170a, each include an image sensor 1120b, 1140b, 1170b, respectively, located at the distal end of their respective shafts, and are each configured to acquire images. The first image sensor 1120b, due to the positioning of the first endoscope 1120 in the thoracic cavity C, is configured to acquire images of the first surgical instrument 1110 and the tissue structures that are accessible via the thoracic cavity C and to provide data characterizing the acquired images to the controller 1150 for further analysis as described below. The second endoscope 1140 is configured to be inserted into the abdominal cavity A such that the second image sensor 1140b can acquire images of the tissue accessible via the abdominal cavity A as well as of the second and/or third surgical instruments 1130, 1175 also inserted into the abdominal cavity A, which is separated from the thoracic cavity C by the patient's diaphragm 1190. The third endoscope 1170 is configured to be inserted into the esophageal orifice B to acquire images of the inner portions of the esophageal orifice B and other nearby tissue, such as the stomach 1195.

The first endoscope 1120, the second endoscope 1140, and the third endoscope 1170 each include a locator device disposed on the shaft 1120a, 1140a, 1170a of each endoscope 1120, 1140, 1170 that is configured to facilitate the augmentation of the views provided by each image sensor 1120b, 1140b, 1170b. For example, the first endoscope 1120 includes a first endoscope magnet 1120c coupled to the first shaft 1120a, the third endoscope 1170 includes a third endoscope magnet 1170c coupled to the third shaft 1170a, and the second endoscope 1140 includes a magnetic sensor 1140c coupled to the second shaft 1140a and configured to magnetically sense positions of the first endoscope magnet 1120c and the third endoscope magnet 1170c relative to the second endoscope 1140. The positions of the first and third endoscope magnets 1120c, 1170c, as sensed by the magnetic sensor 1140c, are used by the controller 1150 to triangulate coordinates for feature(s) in the images acquired by each endoscope 1120, 1140, 1170 and thereby compile an augmented composite image as explained in further detail below.

The controller 1150 determines a relative location of each of the first, second, and third endoscopes 1120, 1140, 1170, and the controller 1150 generates an augmented composite image based on the image data acquired by the image sensors 1120b, 1140b, 1170c of each of the endoscopes 1120, 1140, 1170 and on magnetic sensor data characterizing the relative positions of each of the first, second, and third endoscopes 1120, 1140, 1170 from the magnetic sensor 1140c of the second endoscope 1140. For example, using the determined relative location, the controller 1150 is configured to combine one or more elements of the image data into the augmented composite image and provide the augmented composite image to the display 1160 for viewing by a user. FIG. 27A shows one example view of image data acquired by the second endoscope 1140 that characterizes tissue in the abdominal cavity A. As shown in FIG. 27A, the field of view of the second endoscope 1140 includes the second surgical instrument 1130, the third surgical instrument 1175, and the stomach 1195. FIG. 27B shows one example view of the image data acquired by the third endoscope 1170 located inside the esophageal orifice B. Because the third endoscope 1170 is located inside the esophageal orifice B, it cannot visualize the other endoscopes 1120, 1140 or the surgical instruments 1110, 1130, 1175. FIG. 27C shows one example view of image data acquired by the first endoscope 1120 characterizing an image of tissue in the thoracic cavity C. As shown in FIG. 27C, the field of view of the endoscope 1120 includes the first surgical instrument 1110 and the exterior surface of the esophageal orifice B.

The controller 1150 combines one or more components of the image data acquired by the first, second, and third endoscopes 1120, 1140, 1170 as shown in FIG. 27A-FIG. 27C to form an augmented composite image shown in FIG. 27D. Different acquired images would result in a different augmented composite image. As shown, the augmented composite image includes a three-dimensional representation of the structures and/or instruments located within the field of view of each of the first, second, and third endoscopes 1120, 1140, 1170. Accordingly, the augmented composite image provides a common field of view for multiple surgical instruments approaching a surgical site from separate, non-continuous body cavities. In this way, a user can have enhanced visibility of a surgical site in a procedure in which multiple surgical instruments (such as the first, second, and third surgical instruments 1110, 1130, 1175) must approach the surgical site from varying separate and non-continuous body cavities and must work cooperatively to achieve a common surgical purpose. Additional details regarding various embodiments of augmented composite images are provided in, for example, previously mentioned U.S. App. No. 63/249,980 entitled "Cooperative Access" filed on Sep. 29, 2021.

In some embodiments, when surgical instruments (such as any one of the above-described surgical instruments configured to manipulate tissue) are placed in two isolated body cavities, and the surgical instruments are operated on opposed surfaces of a common region of tissue (e.g., target tissue or a common tissue wall, such as a diaphragm separating a thoracic body cavity and a abdominal body cavity) to achieve a common surgical purpose, interrelated limits on the movement of one or more actuators of the surgical instruments can be determined based on the determined locations of the surgical instruments to help avoid damaging tissue at the common region of tissue. For example, with reference to the embodiment of FIG. 26, the first surgical instrument 1110, having been inserted into the thoracic body cavity C, is configured to operate on a first surface of the common tissue region, and the second surgical instrument 1130, having been inserted into the abdominal body cavity A and separated from the first surgical instrument by the diaphragm 1195, is configured to operate on an opposed second surface of the common tissue region. Using images captured of the first and second surgical instruments 1110, 1140 by the first and second endoscopes 1120, 1140, respectively, the controller 1150 determines the location of the first surgical instrument 1110 and the second surgical instrument 1130. The controller 1150 is configured to establish a set of interrelated force or range of motion threshold limits for each of the surgical instruments 1110, 1130 acting on the common region of tissue. The established threshold limits characterize a maximum amount of force or range of motion that can be applied in any given direction relative to the common region of tissue. In some embodiments, the common region of tissue is at least partially anchored to adjacent anatomical structures such that a proportionate amount of the cooperative forces are transmitted into tissue connections to the adjacent anatomical structures. As such, the interrelated force or range of motion threshold limits for each of the surgical instruments 1110, 1130 provide for a maximum level of force imparted on the common region of tissue and the adjacent anatomical structures together by each of the surgical instruments 1110, 1130, thereby mitigating the risk of inadvertent injury to the common region of tissue and the adjacent anatomical structures resulting from force overloading on those structures by the surgical instruments 1110, 1130 and helping to protect areas of tissue and other anatomical structures (e.g., organs, vessels, etc.) that are in proximity to the common region of tissue. While the threshold limits discussed above are maximum or total amounts that can be applied to the common region of tissue, in other embodiments, interrelated force or range of motion threshold limits can be established for one of the surgical instruments 1110, 1130 relative to the other of the surgical instruments 1110, 1130, which may allow for greater flexibility in establishing the interrelated force or range of motion threshold limits as a total amount applied to the common region of tissue or as an amount of force or range of motion applied by one of the surgical instruments 1110, 1130 that is relative or based on an amount applied by the other surgical instrument 1110, 1130.

During a surgical procedure utilizing the interrelated force or range of motion threshold limits, the controller 1150 is configured to coordinate treatment of the common region of tissue by the first and second surgical instruments 1110, 1130 based on the interrelated force or range of motion. For example, the controller 1150 determines locations of the first and second surgical instruments 1110, 1130 based on images of the first and second surgical instruments 1110, 1130 that are acquired by the first and second endoscopes 1120, 1140, respectively, and determines whether the interrelated force or range of motion threshold limits are being exceeded based on the determined locations of the first and/or surgical instruments 1110, 1130 relative to each other and/or the common region of tissue. If the threshold limits are exceeded, the controller 1150 can take one or more actions, such as place a limit on movements or actuation instructions for the first and/or second surgical instruments 1110, 1130 so that motions of the first and second surgical instruments 1110, 1130 together do not exceed threshold limits for the first and second surgical instruments 1110, 1130 as a pair, can provide an alert (visual, audible, and/or tactile) indicating that the threshold limits have been exceeded (such as on the display 1160), etc.

Figure 28:
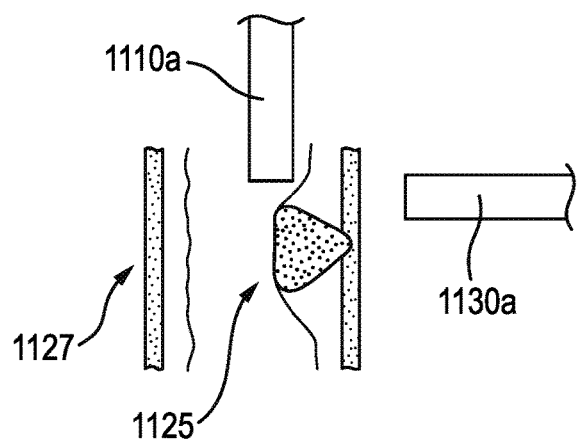
FIG. 28 is an illustrative view of an example embodiment of a system for performing tumor dissection.

Instruments accessing a common tissue region of interest along two different trajectories can work cooperatively in some embodiments to achieve cooperatively antagonistic or complementary forces or motions on a common tissue region of interest (e.g., target tissue or a common tissue wall separating the surgical instruments, such as tissue between two body cavities that are isolated from one another), relative to each other, to achieve a common surgical purpose on the common tissue region of interest. For example, in one surgical procedure involving dissecting a tumor through laparoscopic and endoscopic cooperation, the first and second instruments 1110, 1130 used in the system 1100 can be surgical instruments 1110*a*, 1130*a* illustrated in FIG. 28, such as grasper(s) and/or dissector(s). The first endoscope 1120 is inserted endoscopically into a hollow organ 1127 within a patient, such as an esophagus, and the first surgical instrument 1110*a* is then inserted into the hollow organ 1127 and is configured at such a location to operate on a first surface of a common tissue region containing a tumor 1125. The second endoscope 1140 is deployed laparoscopically outside of the hollow organ 1127, and the second surgical instrument 1130*a* is then deployed laparoscopically and is configured at such a location to operate on an opposed second surface of the common tissue region. During use, the second surgical instrument 1130*a* provides at least one of tissue deflection, retraction, or movement of the common tissue region such that the first surgical instrument 1110*a* has increased access to the common tissue region to dissect the tumor 1125.

In some embodiments, if the first surgical instrument 1110*a* cannot adequately access the tumor 1125 even after tissue deflection, retraction, or movement by the second surgical instrument 1130*a*, the second surgical instrument 1130*a* injects fluid laparoscopically, and the first endoscope 1120 provides visual feedback from within the hollow organ 1127. For instance, the second surgical instrument 1120*a* can inject a saline solution laparoscopically into a sub-mucosal space under the tumor 1125 to lift the tumor 1125 away from a serosal tissue layer to provide increased access to the tumor 1125 for the first surgical instrument 1110*a* for dissection. In other embodiments, the first surgical instrument 1110*a* injects fluid endoscopically when a location of the tumor 1125 cannot initially be determined laparoscopically, and the fluid that is injected can contain one or more additives in some embodiments, such as methylene blue, fluorescing dyes, iron based additives, ionic silver, barium, calcium solution, iodine isotopes, etc., to help in identifying the location of the tumor 1125 laparoscopically. In still other examples, to further increase access to the tumor 1125, after injection of the fluid laparoscopically or endoscopically, a submucosal space created by the injection is entered by a flexible scope or catheter with a balloon that is inflated to increase distension of the tumor 1125 without requiring further fluid introduction to avoid any disruption from leaking fluid. Furthermore, instead of the first or second surgical instruments 1110a, 1130a injecting fluid, other embodiments can use a laparoscopic suction instrument to position a laparoscopic side of the tumor 1125 to provide increased stability and repositioning, as needed, while the first instrument 1110a dissects the tumor 1125. In some suction embodiments, the laparoscopic suction instrument creates a concave shape to pull adventitia away from the tumor 1125 to provide counter traction while the first surgical instrument 1110a grasps and dissects the tumor 1125. Using suction instead of fluid injection allows for both repositioning of the tumor 1125 and avoids any complications from leaking fluid.

Figure 29:
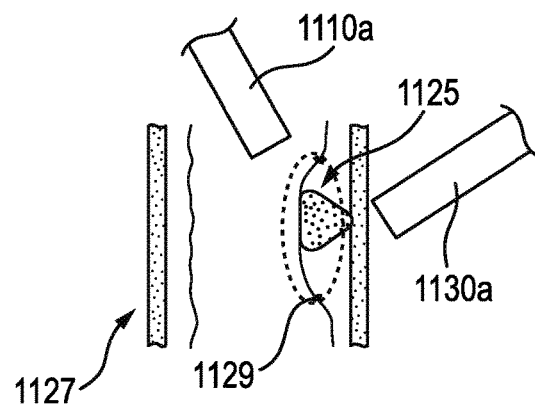
FIG. 29 is an illustrative view of the system for performing tumor dissection of FIG. 28.
Figure 30:
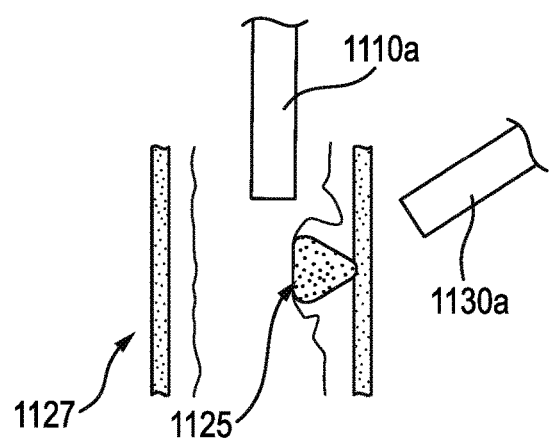
FIG. 30 is an illustrative view of the system for performing tumor dissection of FIG. 28.
Figure 31:
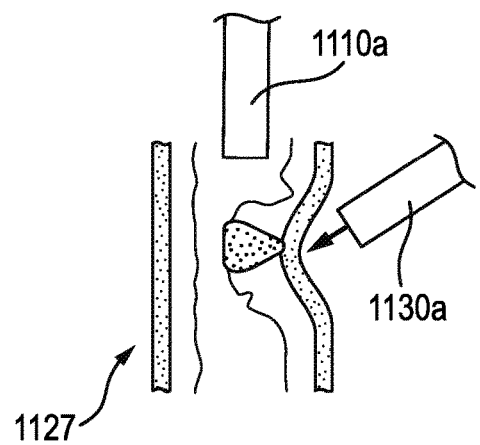
FIG. 31 is an illustrative view of the system for performing tumor dissection of FIG. 28.

In some embodiments, it is beneficial to endoscopically ablate a perimeter 1129 of tissue around the tumor 1125 to establish a desired margin of tissue for removal to further isolate the tumor 1125 for dissection, as illustrated by a broken circle around the tumor 1125 in FIG. 29, FIG. 30, and FIG. 31. In this illustrated embodiment, the first surgical instrument 1110a first ablates tissue around the tumor 1125 to create the perimeter 1129, as shown in FIG. 29, and fluid is introduced to the perimeter 1129 during ablation, as needed, to maintain tissue temperature below a predetermined threshold to avoid charring. The tumor 1125 can then be further separated for dissection using the same approaches discussed above. For example, fluid can be injected laparoscopically by the second instrument 1130a or endoscopically by the first instrument 1110a, as illustrated in FIG. 30, and/or suction can be applied laparoscopically by the second instrument 1130a, as illustrated in FIG. 31. Various embodiments of ablation devices and methods of ablating tissue are further described in, for example, previously mentioned U.S. Pat. App No. 63/249,658 entitled "Surgical Devices, Systems, And Methods For Control Of One Visualization With Another" filed on Sep. 29, 2021.

Furthermore, while the first endoscope 1120 provides visual feedback from within the hollow organ 1127 in some embodiments, it can be beneficial for the second endoscope 1140 to provide visualization of tissue interaction from the laparoscopic side in some embodiments to help direct dissection by the first surgical instrument 1110a on the endoscopic side and to identify any tumor infiltration onto tissue walls of the laparoscopic side. If the tumor 1125 is visible laparoscopically, the tumor 1125 will have most likely spread through a full thickness of the tissue wall into the serosal layer. To help confirm that the tumor 1125 has spread, the user can use a variety of different approaches known in the art, such as monochromatic blue laser light technology, confocal laser endomicroscopy, and/or fluorescing technologies, to help ensure that the user is able to identify and visualize all of the tumor 1125 and to reduce a risk of mistakenly leaving some portion of the tumor 1125 in the tissue. Any portion of the tumor 1125 visible laparoscopically provides an exterior margin of tissue for removal to help a user remove all of the tumor 1125. In some embodiments, to assist in removing the tumor 1125 when a portion of it is visible from the laparoscopic side, the tumor 1125 is marked or traced from the endoscopic side, such as through use of laser pointing, touch and computer vision tagging, etc., with anticipated margins that are registered in the global coordinate system of the system 1000. The identified margins are then mapped on the laparoscopic side, such as through use of structured light 3D surface mapping, and/or are augmented onto a view of the surgical site through the augmented composite images approaches discussed above to assist the user in entirely removing the tumor 1125. When the tumor 1125 is visible laparoscopically, the user may need to use laparoscopic dissection to remove some or all of the tumor 1125. While a laparoscopic dissection can provide easier access to tumors in some situations, it can also create a hole in the hollow organ that may require sealing to promote healing, in which case sealing can be performed, such as sealing illustrated in FIG. 23 and FIG. 24 in which the adjunct 1085 seals a hole 1080a.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety for all purposes.

What is claimed is:

1. A system, comprising:
   a first surgical instrument configured to be inserted into a first body cavity of a patient, the first body cavity located outside of a lumen structure of the patient, the first surgical instrument configured to deliver an adjunct to a target area located at the lumen structure;
   a second surgical instrument configured to be inserted into the lumen structure and to deliver a cooperative fixating implant to the surgical site from within the lumen structure such that the cooperative fixating implant helps maintain the adjunct in place at the target area;
   a first endoscope having a first image sensor configured to acquire a first image of the first surgical instrument within the first body cavity and positioned such that the second surgical instrument is not within a field of view of the first image sensor;
   a second endoscope having a second image sensor configured to acquire a second image of the second surgical instrument within the lumen structure and positioned such that the first surgical instrument is not within a field of view of the second image sensor; and
   a controller configured to receive the first and second images, to determine a first location of the first surgical instrument and a second location of the second surgical instrument relative to one another based on the received first and second images, and to coordinate cooperative movement of the first and second surgical instruments based on the determined first and second locations.

2. The system of claim 1, wherein the adjunct is configured to require interaction from each of the first and second surgical instruments for implantation of the adjunct.

3. The system of claim 1, wherein the adjunct is configured to require interaction from within the first body cavity located outside of the lumen structure of the patient and from within the lumen structure for implantation of the adjunct.

4. A system, comprising:
   a data processor; and
   a memory storing instructions configured to cause the data processor to perform operations comprising:
     receiving, in real time, from a first image sensor of a first endoscope, first image data characterizing a first image of a first surgical instrument disposed within a first body cavity of a patient and located outside of a lumen structure of the patient, the first surgical instrument configured to deliver an adjunct to a target area located at the lumen structure;

receiving, in real time, from a second image sensor of a second endoscope, second image data characterizing a second image of a second surgical instrument disposed within the lumen structure, the second surgical instrument configured to deliver a cooperative fixating implant to the target area from within the lumen structure such that the cooperative fixating implant helps maintain in place at the target area, the second surgical instrument being outside of a field of view of the first endoscope and the first surgical instrument being outside of a field of view of the second endoscope;

determining, based on the received first image data, a first location of the first surgical instrument;

determining, based on the received second image data, a second location of the second surgical instrument; and coordinating cooperative movement between the first and second surgical instruments based on the determined first and second locations.

5. The system of claim 4, wherein the adjunct is configured to require interaction from each of the first and second surgical instruments for implantation of the adjunct.

6. The system of claim 4, wherein the adjunct is configured to require interaction from within the first body cavity located outside of the lumen structure of the patient and from within the lumen structure for implantation of the adjunct.

7. A method, comprising:

receiving, by a controller, in real time, from a first image sensor of a first endoscope, first image data characterizing a first image of a first surgical instrument disposed within a first body cavity of a patient and located outside of a lumen structure of the patient, the first surgical instrument configured to deliver an adjunct to a target area located at the lumen structure;

receiving, by the controller, in real time, from a second image sensor of a second endoscope, second image data characterizing a second image of a second surgical instrument disposed within the lumen structure, the second surgical instrument configured to deliver a cooperative fixating implant to the target area from within the lumen structure such that the adjunct is maintained in place at the target area by the cooperative fixating implant, the second surgical instrument being outside of a field of view of the first endoscope and the first surgical instrument being outside of a field of view of the second endoscope;

determining, by the controller, based on the received first image data, a first location of the determining, by the controller, based on the received second image data, a second location of the second surgical instrument relative to the first location of the first surgical instrument; and coordinating, by the controller, cooperative movement between the first and second surgical instruments based on the determined first and second locations.

8. The method of claim 7, wherein the adjunct requires interaction from each of the first and second surgical instruments for implantation of the adjunct at the target area.

9. The method of claim 7, wherein the adjunct requires interaction from within the first body cavity located outside of the lumen structure of the patient and from within the lumen structure for implantation of the adjunct at the target area.

* * * * *